United States Patent
Kupiecki et al.

(10) Patent No.: US 7,351,247 B2
(45) Date of Patent: Apr. 1, 2008

(54) DEVICES AND METHODS FOR INTERCONNECTING BODY CONDUITS

(75) Inventors: David Kupiecki, San Francisco, CA (US); Stanley R. Conston, San Carlos, CA (US); Candice Danielle Pinson, Mountain View, CA (US); Ron K. Yamamoto, San Francisco, CA (US); Meir Moshe, El Sobrante, CA (US); Aaron Miller, San Francisco, CA (US)

(73) Assignee: Bioconnect Systems, Inc., Ambler, PA (US)

( * ) Notice: Subject to any disclaimer, the term of this patent is extended or adjusted under 35 U.S.C. 154(b) by 549 days.

(21) Appl. No.: 10/235,944

(22) Filed: Sep. 4, 2002

(65) Prior Publication Data

US 2004/0087984 A1    May 6, 2004

(51) Int. Cl.
*A61B 17/08*    (2006.01)
*A61M 29/00*    (2006.01)

(52) U.S. Cl. .................. 606/153; 606/198; 606/194

(58) Field of Classification Search .............. 606/139, 606/142, 143, 101, 108, 191, 192, 194, 198, 606/153, 154, 155; 623/1.11, 1.35; 600/204; 604/107

See application file for complete search history.

(56) References Cited

U.S. PATENT DOCUMENTS

| | | | |
|---|---|---|---|
| 2,127,903 A | 8/1938 | Bowen | |
| 3,974,835 A | 8/1976 | Hardy, Jr. | |
| 4,352,358 A | 10/1982 | Angelchik | |
| 4,667,673 A | 5/1987 | Li | |
| 4,705,040 A * | 11/1987 | Mueller et al. ............. | 606/108 |
| 4,787,386 A | 11/1988 | Walsh et al. | |
| 5,141,516 A | 8/1992 | Detweiler | |
| 5,453,090 A * | 9/1995 | Martinez et al. ........... | 623/1.11 |
| 5,456,714 A | 10/1995 | Owen | |
| 5,503,635 A | 4/1996 | Sauer et al. | |
| 5,586,987 A | 12/1996 | Fahy | |
| 5,634,936 A | 6/1997 | Linden et al. | |
| 5,669,924 A * | 9/1997 | Shaknovich ............... | 623/1.11 |
| 5,676,670 A | 10/1997 | Kim | |
| 5,683,451 A * | 11/1997 | Lenker et al. ............. | 623/1.11 |
| 5,716,325 A * | 2/1998 | Bonutti ...................... | 600/204 |
| 5,830,222 A | 11/1998 | Makower | |
| 5,853,422 A | 12/1998 | Huebsch et al. | |
| 5,868,761 A | 2/1999 | Nicholas et al. | |
| 5,868,763 A | 2/1999 | Spence et al. | |

(Continued)

FOREIGN PATENT DOCUMENTS

JP    02003220065    8/2003

(Continued)

*Primary Examiner*—Julian W. Woo
(74) *Attorney, Agent, or Firm*—Fay Kaplun & Marcin, LLP

(57) ABSTRACT

The present invention provides devices and associated methods for delivering side-to-side and end-to-side anastomotic connectors to join any two (or more) vessels together such that fluid communication is established between the lumens of the two or more joined vessels. The systems of the present invention employ one or more deployment mechanisms over which the anastomotic connector is positioned for delivery and subsequently deployment within a vessel. The deployment mechanisms may be inflatable balloons or expandable baskets or a combination thereof or the like, which, when inflated and/or expanded, cause one or more portions of the anastomotic connector to deploy.

13 Claims, 33 Drawing Sheets

U.S. PATENT DOCUMENTS

| | | | |
|---|---|---|---|
| 5,868,777 A * | 2/1999 | Lam | 606/194 |
| 5,893,886 A | 4/1999 | Zegdi et al. | |
| 5,976,178 A | 11/1999 | Goldsteen et al. | |
| 6,017,352 A | 1/2000 | Nash et al. | |
| 6,030,395 A | 2/2000 | Nash et al. | |
| 6,036,702 A | 3/2000 | Bachinski et al. | |
| 6,036,705 A | 3/2000 | Nash et al. | |
| 6,056,762 A | 5/2000 | Nash et al. | |
| 6,063,114 A | 5/2000 | Nash et al. | |
| 6,068,638 A | 5/2000 | Makower | |
| 6,113,612 A | 9/2000 | Swanson et al. | |
| 6,152,945 A | 11/2000 | Bachinski et al. | |
| 6,176,864 B1 | 1/2001 | Chapman | |
| 6,190,353 B1 | 2/2001 | Makower et al. | |
| 6,190,397 B1 | 2/2001 | Spence et al. | |
| 6,193,734 B1 | 2/2001 | Bolduc et al. | |
| 6,206,913 B1 | 3/2001 | Yencho et al. | |
| 6,214,022 B1 | 4/2001 | Taylor et al. | |
| 6,217,585 B1 | 4/2001 | Houser et al. | |
| 6,231,587 B1 | 5/2001 | Makower | |
| 6,241,741 B1 | 6/2001 | Duhaylongsod et al. | |
| 6,283,983 B1 | 9/2001 | Makower et al. | |
| 6,302,905 B1 | 10/2001 | Goldsteen et al. | |
| 6,350,280 B1 | 2/2002 | Nash et al. | |
| 6,371,965 B2 | 4/2002 | Gifford, III et al. | |
| 6,402,767 B1 | 6/2002 | Nash et al. | |
| 6,409,739 B1 | 6/2002 | Nobles et al. | |
| 6,419,681 B1 | 7/2002 | Vargas et al. | |
| 6,428,550 B1 | 8/2002 | Vargas et al. | |
| 6,440,163 B1 | 8/2002 | Swanson et al. | |
| 6,443,965 B1 | 9/2002 | Gifford, III et al. | |
| 6,458,140 B2 * | 10/2002 | Akin et al. | 606/153 |
| 6,461,320 B1 | 10/2002 | Yencho et al. | |
| 6,485,496 B1 * | 11/2002 | Suyker et al. | 606/153 |
| 6,497,710 B2 | 12/2002 | Yencho et al. | |
| 6,508,824 B1 | 1/2003 | Flaherty et al. | |
| 6,517,558 B2 | 2/2003 | Gittings et al. | |
| 6,537,287 B1 | 3/2003 | Yencho et al. | |
| 6,537,288 B2 | 3/2003 | Vargas et al. | |
| 6,565,581 B1 | 5/2003 | Spence et al. | |
| 6,585,762 B1 | 7/2003 | Stanish | |
| 6,616,675 B1 | 9/2003 | Evard et al. | |
| 6,620,129 B2 * | 9/2003 | Stecker et al. | 604/107 |
| 6,626,920 B2 | 9/2003 | Whayne | |
| 6,652,543 B2 | 11/2003 | Spence et al. | |
| 6,655,386 B1 | 12/2003 | Makower et al. | |
| 6,699,257 B2 | 3/2004 | Gifford, III et al. | |
| 6,709,441 B2 | 3/2004 | Bolduc et al. | |
| 6,719,781 B1 | 4/2004 | Kim | |
| 6,726,697 B2 | 4/2004 | Nicholas et al. | |
| 6,736,825 B2 | 5/2004 | Blatter et al. | |
| 6,740,101 B2 | 5/2004 | Houser et al. | |
| 6,776,785 B1 | 8/2004 | Yencho et al. | |
| 6,786,914 B1 | 9/2004 | Vargas et al. | |
| 6,790,229 B1 | 9/2004 | Berreklouw | |
| 6,913,607 B2 | 7/2005 | Ainsworth et al. | |
| 6,916,327 B2 | 7/2005 | Northrup, III et al. | |
| 6,926,724 B1 | 8/2005 | Chu | |
| 6,962,596 B2 | 11/2005 | Bolduc et al. | |
| 6,972,023 B2 | 12/2005 | Whayne et al. | |
| 7,008,436 B2 | 3/2006 | Barath | |
| 7,018,388 B2 | 3/2006 | Yencho et al. | |
| 7,025,773 B2 | 4/2006 | Gittings et al. | |
| 7,029,482 B1 | 4/2006 | Vargas et al. | |
| 7,041,110 B2 | 5/2006 | Yencho et al. | |
| 7,063,712 B2 | 6/2006 | Vargas et al. | |
| 7,128,749 B1 * | 10/2006 | Vargas et al. | 606/153 |
| 7,160,311 B2 | 1/2007 | Blatter et al. | |
| 7,172,608 B2 | 2/2007 | Vargas et al. | |
| 7,175,637 B2 | 2/2007 | Vargas et al. | |
| 2001/0047165 A1 | 11/2001 | Makower et al. | |
| 2002/0022853 A1 | 2/2002 | Swanson et al. | |
| 2002/0029079 A1 | 3/2002 | Kim et al. | |
| 2002/0091398 A1 | 7/2002 | Galdonik et al. | |
| 2003/0212418 A1 | 11/2003 | Yencho et al. | |
| 2003/0229365 A1 | 12/2003 | Whayne et al. | |
| 2003/0236542 A1 | 12/2003 | Makower | |
| 2004/0073238 A1 | 4/2004 | Makower | |
| 2004/0073282 A1 | 4/2004 | Stanish | |
| 2004/0088042 A1 | 5/2004 | Kim et al. | |
| 2004/0097991 A1 | 5/2004 | Vargas et al. | |
| 2004/0102796 A1 | 5/2004 | Hill et al. | |
| 2004/0122318 A1 | 6/2004 | Flaherty et al. | |
| 2004/0132225 A1 | 7/2004 | Makower | |
| 2004/0158143 A1 | 8/2004 | Flaherty et al. | |
| 2004/0249400 A1 | 12/2004 | Vargas et al. | |
| 2005/0043751 A1 | 2/2005 | Phan et al. | |
| 2005/0043752 A1 | 2/2005 | Phan et al. | |
| 2005/0149073 A1 | 7/2005 | Arani et al. | |
| 2006/0064119 A9 | 3/2006 | Tilson et al. | |
| 2006/0241342 A1 | 10/2006 | Macaulay et al. | |

FOREIGN PATENT DOCUMENTS

| | | |
|---|---|---|
| WO | WO 98/19629 | 5/1998 |
| WO | WO 98/19635 | 5/1998 |
| WO | WO 98/52474 | 11/1998 |
| WO | WO 99/11180 | 3/1999 |
| WO | WO 00/27310 | 5/2000 |
| WO | WO 00/27313 | 5/2000 |
| WO | WO 00/53104 | 9/2000 |
| WO | WO 01/39672 | 6/2001 |

* cited by examiner

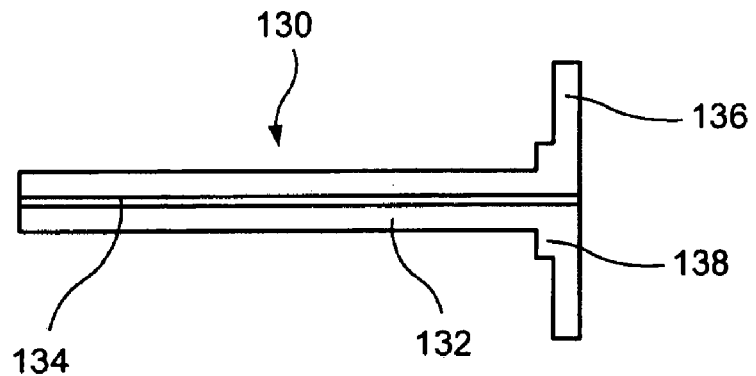
F I G. 4C
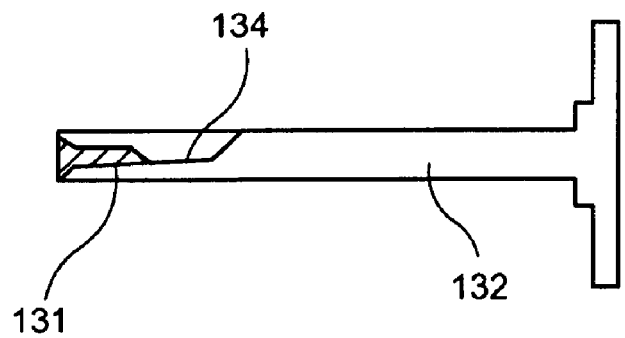
F I G. 4D

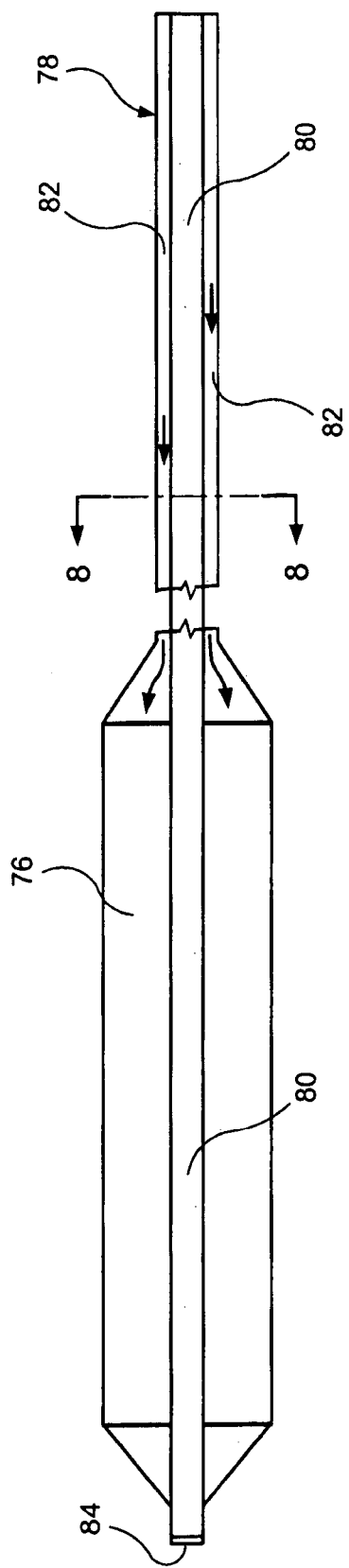
FIG. 5A
FIG. 5C
FIG. 5B

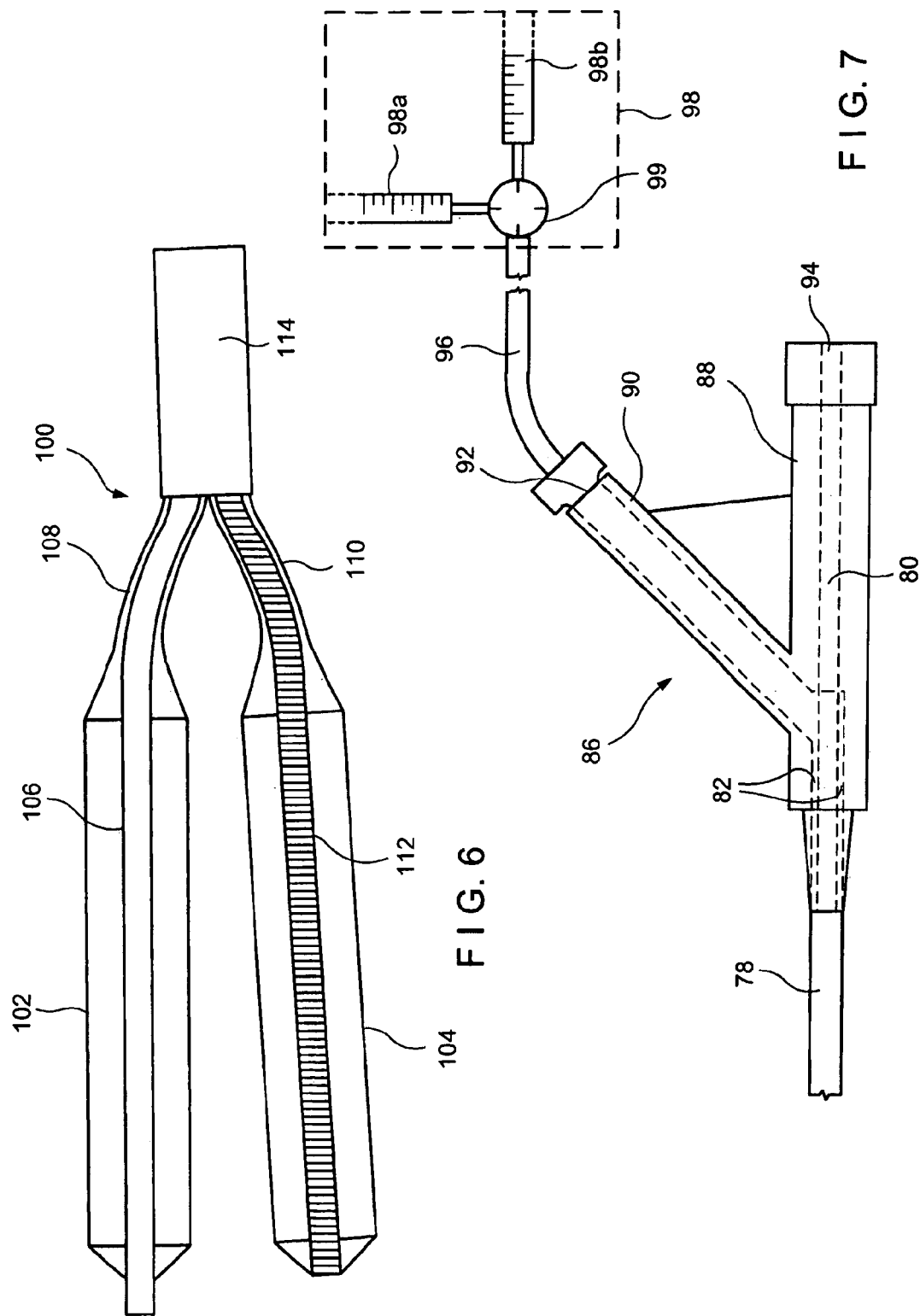

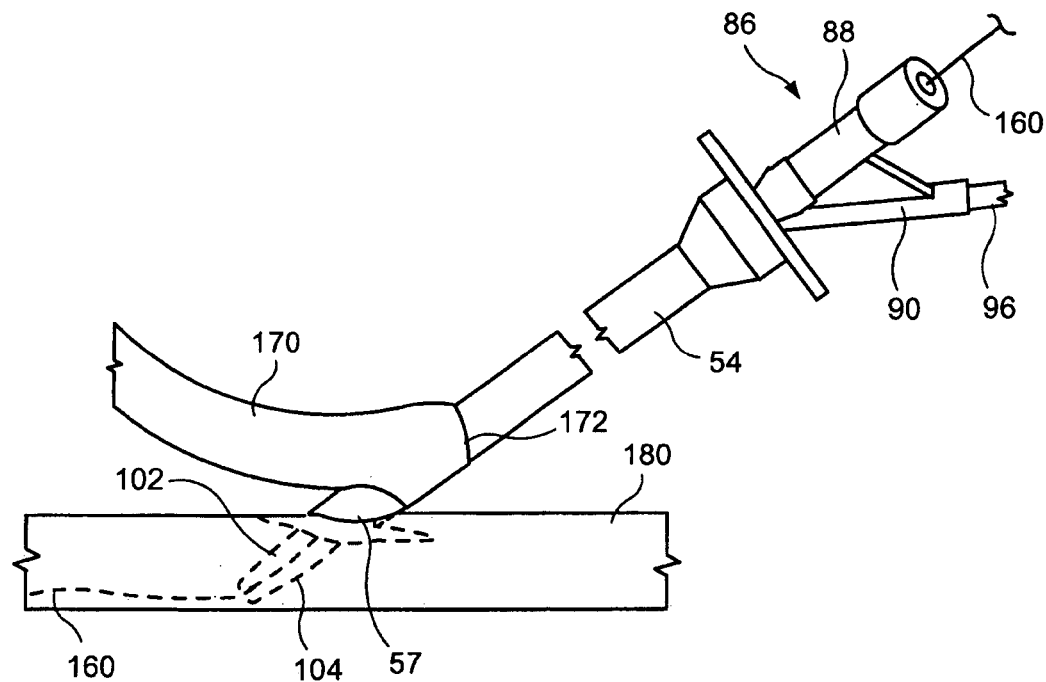
F I G. 8F
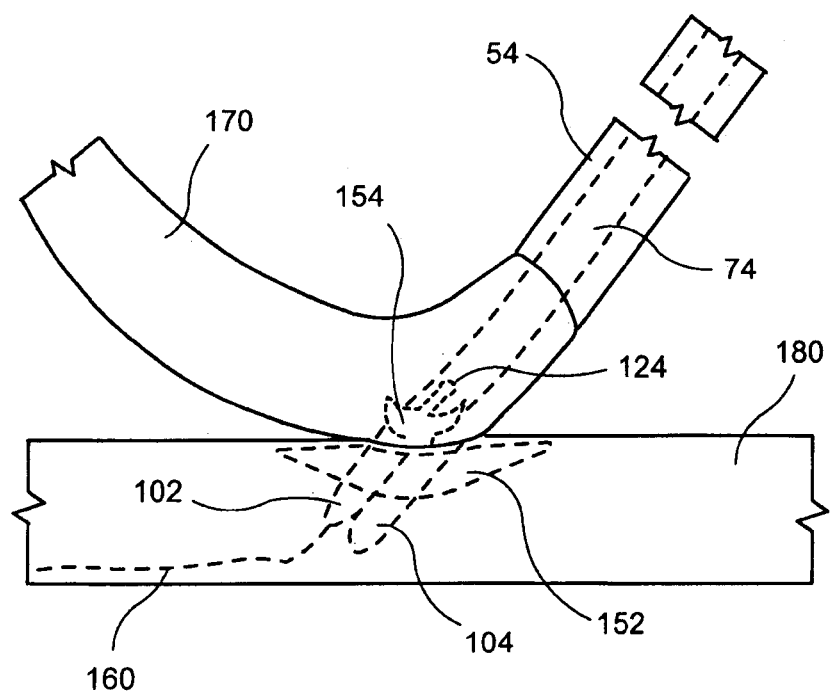
F I G. 8G

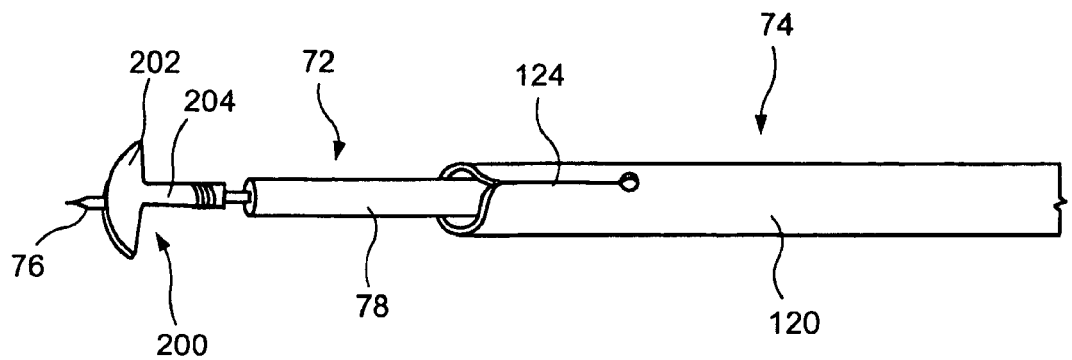
F I G. 9A
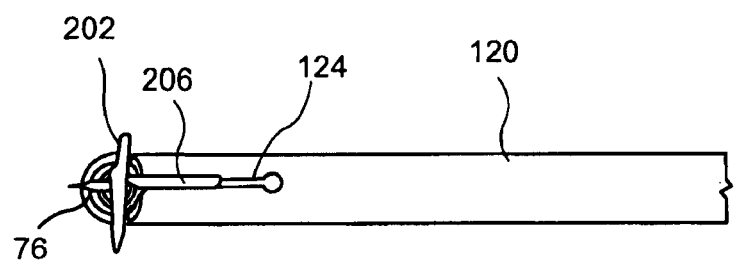
F I G. 9B
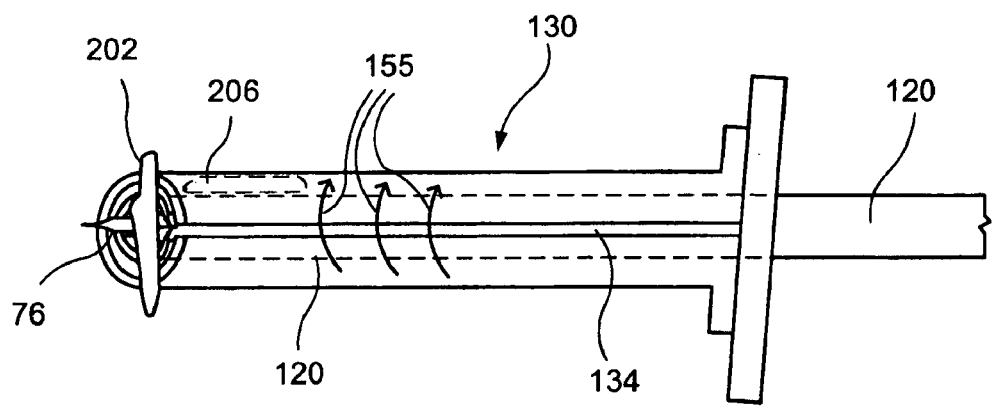
F I G. 9C

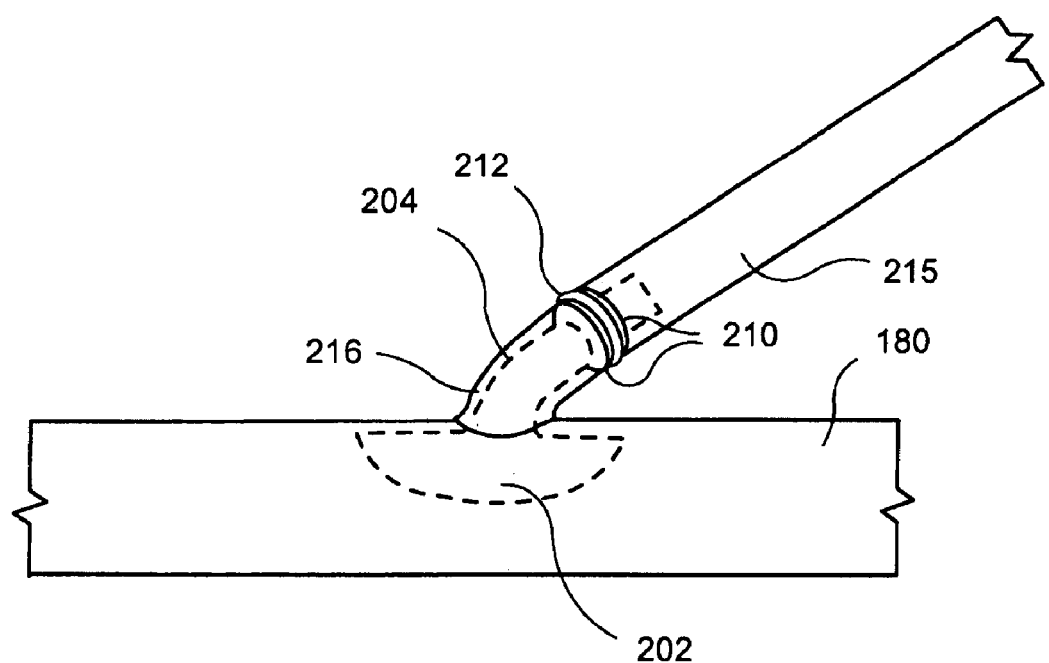
F I G. 9H

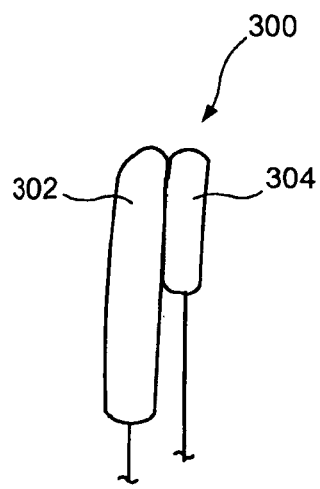
F I G. 10A
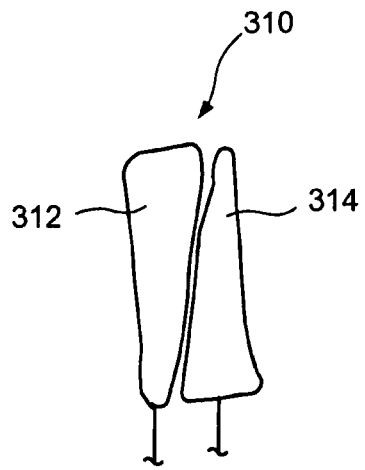
F I G. 10B
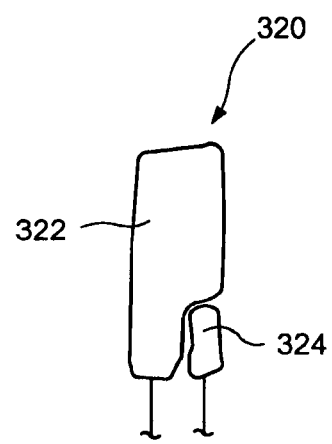
F I G. 10C
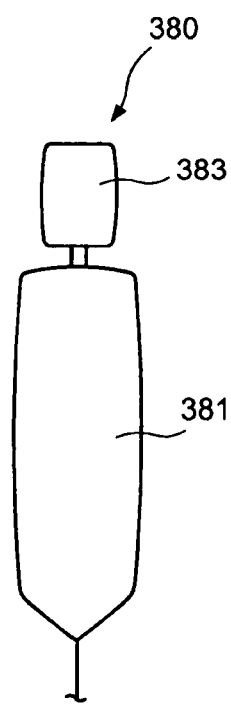
F I G. 10D
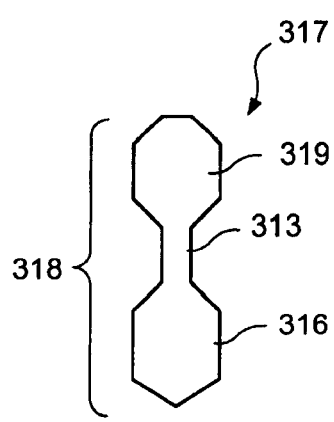
F I G. 10E
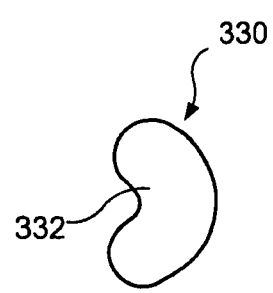
F I G. 10F
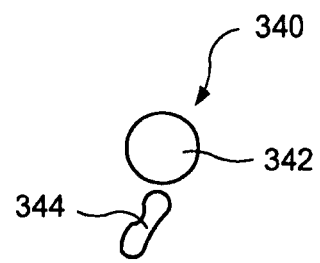
F I G. 10G

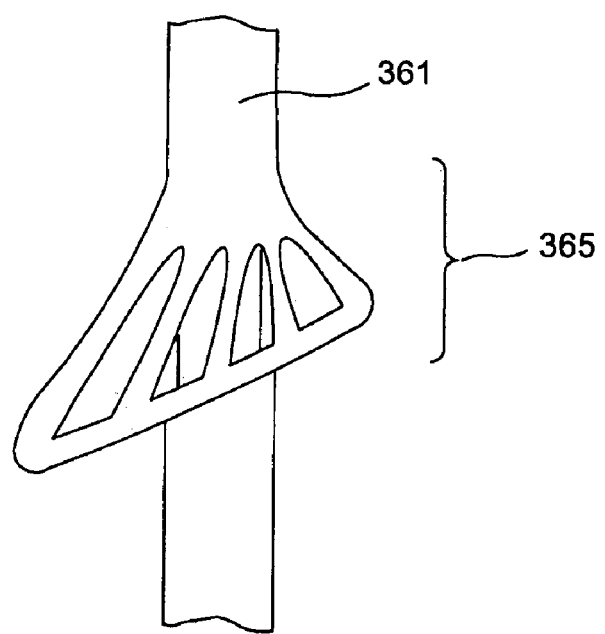
F I G. 13

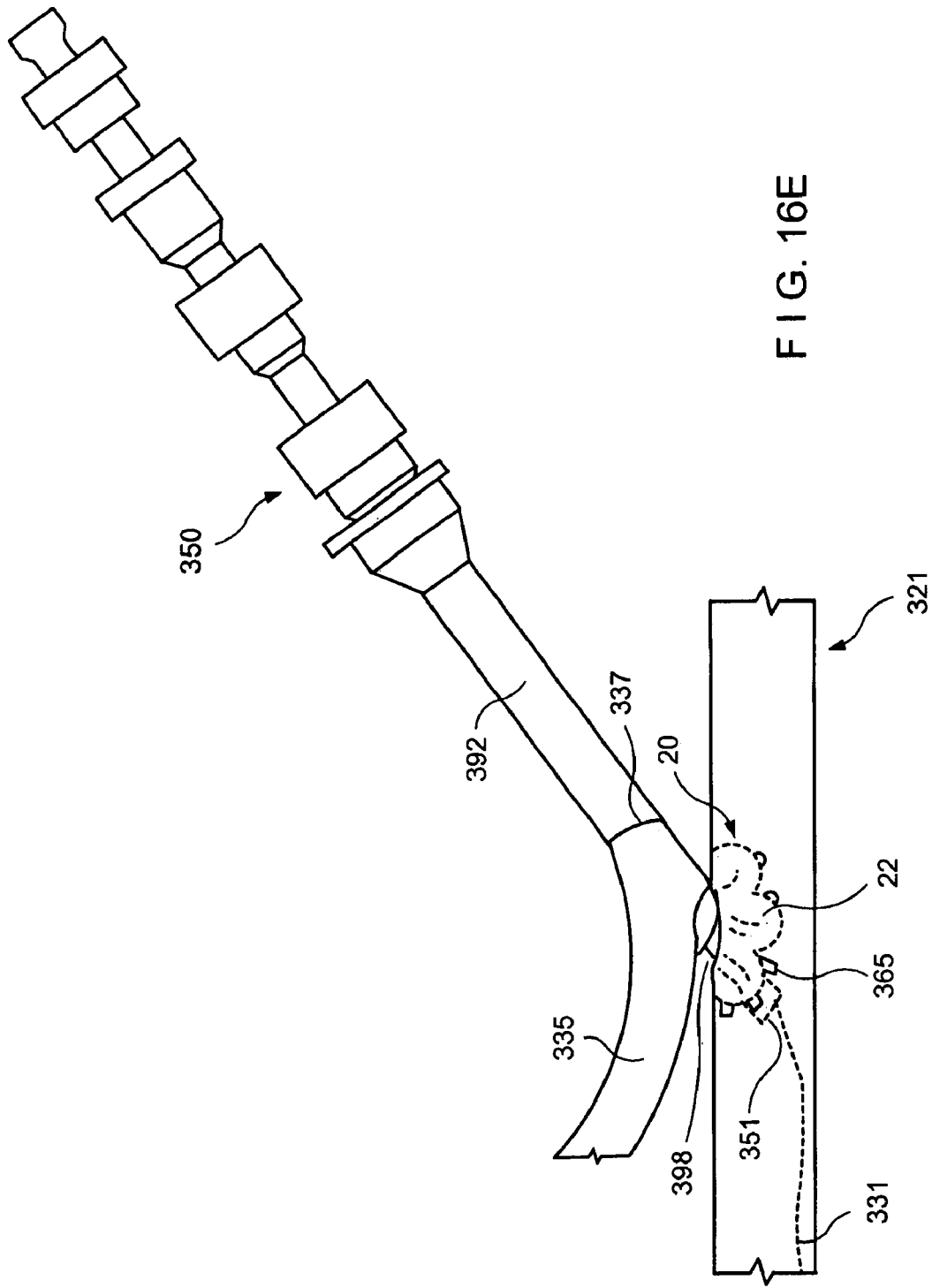

DEVICES AND METHODS FOR INTERCONNECTING BODY CONDUITS

TECHNICAL FIELD

The present invention is generally related to interconnecting body conduits. More particularly, the present invention is related to devices and methods for delivering and implanting devices for interconnecting body conduits such as blood vessels.

BACKGROUND OF THE INVENTION

The human body has numerous conduits such as blood vessels carrying fluid to essential tissues and areas for circulation or excretion. When conduits become damaged, severed or wholly occluded due to physiological problems or diseases, certain sections must be bypassed to allow for the free and continuous flow of fluids. Anastomosis is performed for the purpose of connecting different conduits together to optimize or redirect flow around a damaged or occluded portion of a conduit.

In the context of the peripheral vascular and/or the cardiovascular system, atherosclerosis, a common vascular disease, can cause partial blockage or complete occlusion of an arterial vessel, resulting in restricted blood flow and therefore compromised perfusion to the tissue served by the blood flow. In the case of an occluded or partially occluded coronary vessel, for example, an area of the heart's myocardium would be compromised, which can lead to a myocardial infarction, or other ischemic heart syndrome such as congestive heart failure. In the case of peripheral vascular atherosclerotic disease, occluded vessels lead to ischemic syndromes such as threatened limbs, stroke and other morbidities. In many cases, such a blockage or restriction in the blood flow leading to the heart or peripheral vessels can be treated by a surgical procedure known as an artery bypass graft procedure.

A bypass procedure involves the establishment of an alternate blood supply path to bypass a diseased section of a diseased or compromised artery. In the bypass procedure, the surgeon typically dissects one end of a source or "pedicled" artery (such as the internal mammary artery in the case of coronary artery bypass), or harvests a free vessel segment (typically the saphenous vein in the leg), to use as a graft conduit to bypass the obstruction in the affected artery to restore normal blood flow. The graft vessel is connected to the obstructed vessel by means of an anastomosis procedure wherein an opening in the graft vessel is sutured to the obstructed vessel at an arteriotomy site made within the obstructed vessel. A side-to-side anastomosis procedure involves the attachment of two vessels at incised locations (e.g., arteriotomies) within a side wall of each of the vessels. An end-to-side anastomosis procedure involves the attachment of two vessels at an incised location within a side wall of one of the vessels and at the transected end of the other vessel.

Other applications in which anastomosis is employed include the creation of an arterial to venous fistula for the purpose of either creating a dialysis access site, or, as an alternative means of creating arterial revascularization by "arterializing" a vein through creation of a conduit past the occlusive disease. The latter is often employed in treating peripheral vascular disease but is used in coronary applications as well.

The patency of the anastomosis is crucial to a successful bypass, both by acute and long-term evaluation. Patency may be compromised by technical, biomechanical or pathophysiological means. Among the technical and biomechanical causes for compromised patency (also termed restenosis) are poorly achieved anastomoses, whether induced by poor placement, trauma at the anastomosis site or biological responses to the anastomosis itself. Improperly anastomosed vessels may lead to leakage, create thrombus and/or lead to further stenosis at the communication site, possibly requiring re-operation and further increasing the risk of stroke. As such, forming the anastomosis is the most critical procedure in bypass surgery, requiring precision and accuracy on the part of the surgeon.

The current gold standard for forming the anastomosis is by means of suturing openings (natural or artificial) in the vessels together. Surgeons must delicately sew the vessels together being careful not to suture too tightly so as to tear the delicate tissue, thereby injuring the vessel which may then result in poor patency of the anastomosis. On the other hand, surgeons sometimes inadvertently suture too loosely or do not properly place the sutures so as to provide continuous seal around the arteriotomy site, resulting in leakage of fluid from the anastomosis. In addition to creating a surgical field in which it is difficult to see, leakage of fluid from the anastomosis can cause serious drops in blood pressure, acute or chronic. The loss of blood may cause other deleterious effects on the patient's hemodynamics that may even endanger the patient's life. In addition to the inherent inconsistencies in suture tightness, placement and stitch size and the lack of reproducibility, suturing an anastomosis can be very time consuming.

Advances in anastomotic instruments have been devised in the attempt to provide greater reproducibility of a precise anastomosis and to reduce the time that is required to complete an anastomosis and the necessary size of the surgical field. Many of these new instruments are stapling devices which deploy one or more staples at the anastomotic site in a single-motion action. While stapling techniques have been found to be successful in gastrointestinal procedures, due to the large size and durability of the vessels, it is less adequate for use in vascular anastomosis where the vessels are much smaller.

The manufacturing of stapling instruments small enough to be useful for anastomosing smaller vessels, such as coronary arteries, is very difficult and expensive. As stapling instruments are typically made of at least some rigid and fixed components, a stapler of one size will not necessarily work with multiple sizes of vessels. This requires a surgeon to have on hand at least several stapling instruments of varying sizes. This may significantly raise the cost of the equipment and ultimately the cost of the procedure.

Stapling instruments and staples which are adapted to conform to the smaller sized vessels are difficult to maneuver and, thus, a great deal of time, precision, and fine movement is necessary to successfully approximate the vessel tissue. Often stapling or similar coupling devices require the eversion of the vessel walls to provide intima-to-intima contact between the anastomosed vessels. Everting may not always be practical especially for smaller arteries because of the likelihood of tearing when everted. Another factor which may lead to damage or laceration of the vessel and/or leakage at the anastomosis site is the variability of the force that a surgeon may use to fire a stapling instrument causing the possible over- or under-stapling of a vessel. Still other factors include the unintended inversion of the vessel edges and the spacing between staple points. Rectifying a poorly stapled anastomosis is itself a complicated, time-consuming process which can further damage a vessel.

The tension and/or compression forces exerted on the vessel walls as a result of suturing and stapling can result in damage to the vessel wall, even to the extent of causing tissue necrosis. Damage to the intima of a vessel is particularly problematic as it may inhibit the natural bonding process that occurs between the anastomosed vessels and which is necessary for sufficient patency. Furthermore, damaged vessel walls are likely to have protuberances that, when exposed to the blood stream, could obstruct blood flow or may produce turbulence which can lead to formation of thrombus, stenosis and possible occlusion of the artery.

As cardiac surgery is moving into less invasive procedures, surgical access is being reduced, forcing surgeons to work in constantly smaller surgical fields. These procedures are made more difficult due to the multiple characteristics that are unique to each anastomosis and to each patient. For example, the arteries' internal diameter dimensions are difficult to predict and the inside walls are often covered with deposits of stenotic plaque which creates the risk of dislodging plaque into the patient's blood stream during the anastomosis procedure. The resulting emboli in turn create a greater risk of stroke for the patient. The dislodgement of plaque is most likely to occur when the vessel wall undergoes trauma such as the puncturing, compression and tension exerted on the vessel by suturing and stapling. The vessel walls can also be friable and easy to tear, and are often covered with layers of fat and/or are deeply seated in the myocardium, adding to the difficulty of effectively and safely performing conventional anastomotic procedures.

Many of the drawbacks of the above mentioned anastomotic connectors and techniques have been obviated by recent technological advancements. In particular, novel anastomotic connectors have been developed which avoid compression, tensioning and puncturing of the vessel tissue. Examples of such anastomotic connectors are disclosed in U.S. Pat. Nos. 6,165,185 and 6,251,116, copending U.S. patent application Ser. No. 10/235,948, entitled "Devices and Methods for Interconnecting Conduits and Closing Openings in Tissue", attorney docket no. VASC009 to Akin, et al., filed on even date herewith; and in U.S. Patent Application Publication No. US-2001-0044631-A1, which are herein incorporated by reference. These devices include at least one flexible member in the form of a sheet, membrane or flange which is adapted to conform to and seal with an inner surface or circumference of a vessel into which it is delivered. The flexible member is adapted to utilize only the internal vessel pressure, e.g., blood pressure, exerted thereon to form a substantially fluid-tight seal with the inner surface of the conduit whereby substances within the vessel are prevented from leaking from the artificial opening under normal physiological conditions. As such, these devices obviate the need to compress, puncture or place tension on the vessel tissue and reduce many of the risks associated with prior anastomotic and closure devices. Another advantage of these flexible devices is that they can be made from materials which are biodegradable or bioresorable, such as degradable hydrogels, polymers, protein cell matrices, plant or carbohydrate derivatives (sugars), and the like.

Unlike staples, clips, sutures and the like which often require the surgeon to employ many components for their delivery and implantation in the body, the flexible flanges or membranes may be implanted manually by a surgeon. As such, the use of cumbersome and complicated instrumentation necessary for implanting the devices is avoided. However, the ongoing desire to reduce the size of the surgical opening necessitates the use of minimally invasive delivery devices and techniques, and minimizes the attractiveness of manual implantation of the anastomotic connectors.

Thus, it is desirable to provide minimally invasive devices and techniques for the delivery and implantation of these advanced anastomotic connectors which reduce the access space necessary for performing an anastomosis compared to conventional techniques. It would be additionally beneficial and desirable if such instrumentation was easy to use, minimized the procedure time, minimized the risk of improper alignment between the conduits, and minimized the risk of leakage, tearing and damage at the anastomosis site. It is additionally desirable to provide such delivery devices in which a single configuration may be employed with a variety of configurations of anastomotic connectors, including both side-to-side and end-to-end devices. Further, it would be highly advantageous if such delivery devices were usable for both proximal and distal anastomosis applications, e.g., a graft vessel to the aorta and a graft vessel to a native vessel at a location downstream of the stenotic lesion within the native vessel, respectively.

These and other objects, advantages, and features of the invention will become apparent to those persons skilled in the art upon reading the details of the methods and systems of the present invention which are more fully described below.

SUMMARY OF THE INVENTION

The present invention provides devices and associated methods for implanting or delivering devices within vessels, lumens, ducts or other tubular organs rapidly, safely and in a minimally invasive manner. These devices and methods are particularly helpful in surgical procedures involving the anastomosis of small vessels or the like within a limited surgical access field. A single configuration of the delivery or implantation device of the present invention may be employed with a variety of embodiments of anastomotic connectors.

The present invention is useful for delivering side-to-side and end-to-side anastomotic connectors to join any two (or more) vessels together such that fluid communication is established between the lumens of the two or more joined vessels, where representative types of vessels include, but are not limited to, vascular vessels and other vessels of the body, where one of the vessels may be a synthetic vessel or graft vessel from a donor, e.g., autograft or allograft. The present invention is particularly useful for joining vessels in coronary artery bypass graft procedures (CABG), in peripheral vascular bypass graft procedures, such as femoropopiteal (Fem-Pop) bypasses, and to form arterial-venous fistulas.

The systems of the present invention employ one or more deployment mechanisms over which the anastomotic connector is positioned. The deployment mechanisms may be inflatable balloons or expandable baskets or a combination thereof or the like, which, when inflated and expand, cause one or more portions of the anastomotic connector to deploy. The deployment mechanisms may be activated and deactivated as need to optimally deploy and position the connector.

Certain methods of the present invention involve the use of the subject systems to deliver anastomotic connectors to interconnect vessels. One such method involves the delivery of an anastomosis connector having at least one flexible flange and a tubular flow channel.

Other features, objects, aspects and advantages of the invention will become apparent to those skilled in the art upon reading this disclosure in combination with the accompanying figures.

BRIEF DESCRIPTION OF THE FIGURES

To facilitate understanding, the same reference numerals have been used (where practical) to designate similar elements that are common to the Figures. Some such numbering has, however, been omitted for the sake of drawing clarity.

FIGS. 4A-4D illustrate exemplary embodiments of the various components of an anastomotic connector delivery device of the present invention having at least one inflatable member.

FIGS. 5A and 5B illustrate an exemplary embodiment of an anastomotic connector engagement member of the delivery device of FIGS. 4A-4C. FIG. 5C illustrates an exemplary embodiment of an alternative anastomotic connector engagement member that does not include a guidewire lumen.

FIG. 6 illustrates another exemplary embodiment of an engagement member usable with the delivery devices of the present invention.

FIG. 7 illustrates the proximal end of an engagement member of the present invention operatively connected to an inflation mechanism.

FIGS. 8A-8H illustrate various steps of a method of the present invention of forming a side-to-side anastomotic connection using the subject inflatable deployment member devices and systems.

FIGS. 9A-9H illustrate various steps of a method of the present invention of forming an end-to-side anastomotic connection using the subject inflatable deployment member devices and systems.

FIGS. 10A-10G illustrate various exemplary embodiments of inflation mechanisms of the present invention.

FIG. 13 is a plan view of an exemplary embodiment of an alternative embodiment of the expandable member in accordance with the present invention in an expanded configuration.

FIGS. 16A-16G illustrate various steps of a method of the present invention of forming a side-to-side anastomotic connection using the subject expandable deployment member devices and systems.

DETAILED DESCRIPTION OF THE PREFERRED EMBODIMENTS

Figure 1:
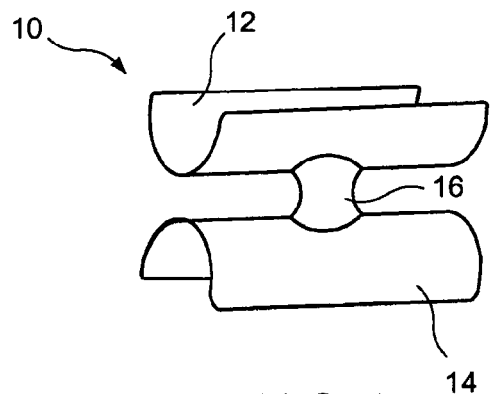
FIG. 1 is a perspective view of a side-to-side anastomotic connector which is implantable using the delivery devices of the present invention.

Before the present invention is described in such detail, it is to be understood that this invention is not limited to particular variations set forth herein as various changes or modifications may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

In further describing the subject invention, the anastomotic connector devices which may be used with the present invention are described first. Next, a description of the subject delivery devices and systems is provided followed by a description of the methods of using them. Finally, a review of the kits of the present invention which include the subject delivery systems and devices for performing the subject methods is provided.

In the following description, the present invention as used in anastomotic applications will be described in the context of joining two vessels wherein at least one of the vessels is the target vessel to be bypassed such as a coronary or peripheral vessel. The other vessel is a graft vessel which may be pedicled or segmented from its native location. However, such exemplary application is not intended to be limiting and those skilled in the art will appreciate that the subject devices, systems and methods are useful for the joining of other types of conduits and structures and may be used to join any numbers of vessels or other conduits and structures, i.e., may be used to join greater than two vessels or other conduits and structures.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Anastomotic Connectors

Figure 2A:
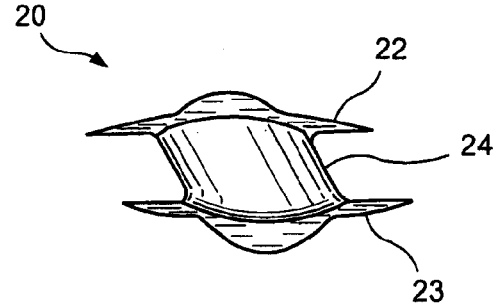
FIG. 2A is a side perspective view of another side-to-side anastomotic connector which is implantable using the delivery devices of the present invention.
Figure 2B:
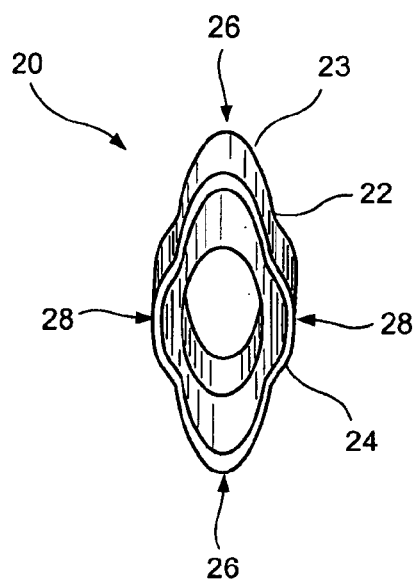
FIG. 2B is a top perspective view of the anastomotic connector device of FIG. 2A.
Figure 3:
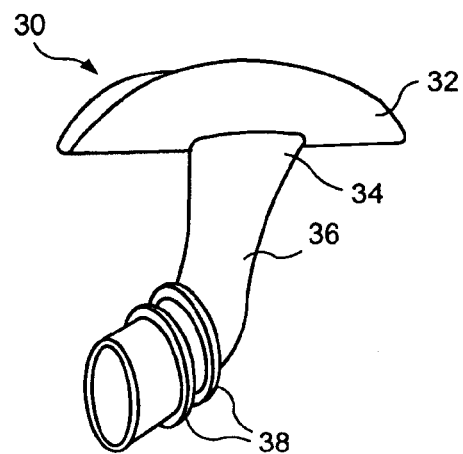
FIG. 3 is a perspective view of an end-to-side anastomotic connector which is implantable using the delivery devices of the present invention.

FIGS. 1-3 illustrate various embodiments of the anastomotic connectors generally described above which are suitable for use with the present invention. Such devices are described in detail in U.S. Pat. Nos. 6,165,185 and 6,251,116; and in copending U.S. patent application Ser. No. 10/235,948, entitled "Devices and Methods for Interconnecting Conduits and Closing Openings in Tissue", attorney docket no. VASC009 to Akin, et al., filed on even date herewith. While the subject invention is especially useful for delivering the anastomotic connectors disclosed in these patents, it will be obvious to those skilled in the art that the subject devices and methods herein described may be employed with variations of these anastomotic connectors. As such, reference to specific embodiments of anastomotic connectors is solely for purposes of describing the subject invention and is not in any way intended to limit the scope or the function of the subject invention.

While reference can be made to the above-referenced patents for a detailed description of anastomotic connectors usable with the present invention, a brief description is herein provided for purposes of convenience. The delivery devices of the present invention may be used with both side-to-side and end-to-side anastomotic connectors and procedures. A side-to-side anastomosis procedure involves the attachment of two vessels at incised locations (e.g., arteriotomies) within a side wall of each of the vessels. An end-to-side anastomosis procedure involves the attachment of two vessels at an incised location within a side wall of one of the vessels and at the transected end of the other vessel.

Common to the anastomotic connectors of the present invention are two members which are in fluid communication with each other. Each device comprises at least one flexible member in the form of a sheet, membrane or flange. The devices configured for forming a side-to-side anastomotic connection include a second flexible membrane wherein a flow opening or channel resides between the members such that they are in fluid communication. Those connectors configured for forming an end-to-side anastomotic connection have a second member having a tubular configuration wherein the lumen of the tubular member extends from a flow opening in the flexible member.

In either configuration, the flexible members are adapted to conform to and seal with an inner surface or circumference of a vessel into which it is delivered. Furthermore, the flexible member is adapted to utilize the internal vessel pressure exerted thereon to form a substantially fluid-tight seal with the inner surface of the conduit whereby substances within the vessel are prevented from leaking from the artificial opening under normal physiological conditions. More particularly, the flexible member has first and second surfaces. The first or lumen-facing surface is adapted to utilize the internal conduit pressure exerted thereon to form a substantially fluid-tight seal between the second or vesselcontacting surface and an inner wall or circumference of the vessel. Thus, upon deployment of the flexible member into a vessel, the member conforms to the interior walls of the vessel to provide a sealing contact and sufficient physical stability to the device to prevent displacement from the vessel. Moreover, the substantially fluid-tight seal is formed without compressing, tensioning or puncturing the vessel wall.

The flexible members are constrictable (such as by bending or folding) from an original state to a size sufficient to fit through the artificial opening and are expandable from a constrictable state to be securely and permanently self-retained within the vessel upon implantation. The flexible members have relatively thin walls, thus minimally interfering with fluid flow within the interconnected vessels. The intravascular pressure against the underside of the flexible member secures the member against the inside vessel wall thereby preventing leakage from the anastomosis site. Additionally, the configuration of the flexible members is such that it provides an element of passive force when deployed within the vessel so as to pull the two vessels together for better sealing and healing of the vessel walls.

In certain embodiments the flanges have constant diameters about their circumference (e.g., circular) or the same length and width dimensions (e.g., square). In other embodiments, the flanges have varying diameters (e.g., elliptical, oval) or lengths and widths (e.g., rectangular), wherein the flanges have a major axis, i.e., a longer axis, and a minor axis, i.e., a shorter axis. In any embodiment, the flexible membranes are sufficiently flexible and compliant to be folded from an original state about any axis defined by the membranes, as well as to be folded about an axis which is defined by the flow channel, which may be substantially perpendicular to the surface of the flange or at angle. Such flexibility facilitates implantation of the anastomotic connectors with the devices of the present invention.

Upon release of the membranes from a constricted or folded condition, each membrane subsequently conforms to the interior walls of a conduit to provide a sealing contact along the contact surface of the membrane. Once deployed within the conduits, the sealing contact and stiffness properties of the flanges provide sufficient physical stability to the device to prevent displacement from the respective vessels.

The flexible flanges may have a variety of different configurations, shapes, thickness(es), surface areas, lengths and widths (or diameters). Useful configurations include, but are not limited to, partial cylinders or generally planar configurations having circular elliptical, stared, petaled or rectangular shapes, or combinations of these configurations.

Each flange or membrane includes an opening through its thickness which provides a pathway through which fluid can be transported between anastomosed conduits. More specifically, the flow opening provides a location of permanent connection between the two members of the anastomosis device, whether a side-to-side or an end-to-side device, and thus, establishes fluid communication between the vessels connected by the implanted device.

Generally, the size and shape of the flexible members are dependent on the size (i.e., the circumference or diameter) and shape of the bodily lumen into which it is to be used. For example, larger segments may be preferable when performing a proximal anastomosis to an aorta, or when anastomosing peripheral (e.g., in the leg) or abdominal vessels while smaller segments are more appropriate for coronary arteries and veins. Also, the length or width (or diameter) dimensions or both, may be dictated by the length of the incision or arteriotomy within the lumen or vessel into which the segment is to be placed.

The anastomotic connectors may be made of biodegradable or bioresorbable materials or non-resorbable materials. Suitable bioresorabable materials include but are not limited to degradable hydrogels, polymers such as lactides/glycolides or PHAs; protein cell matrices, plant, carbohydrate derivatives (sugars), and the like. Suitable non-resorbable materials include but are not limited to polymers and elastomers such as silicones, fluoropolymers, polyolephins or polyurethanes might also be used. In addition, the anastomotic connectors may be fabricated from composites of two or more different types of materials, etc, e.g., the device may be fabricated from a blood impermeable membrane attached to a structural article or scaffold. In addition to being adequately biocompatible, the material(s) have appropriate mechanical properties for facilitating insertion, retention and sealing of the members within the vessels. Additionally, the anastomotic connectors may be made of any suitable autologous, allo- and xeno-graft biomaterials.

Referring now to the Figures, specific embodiments of anastomotic connectors are illustrated which are usable with the present invention. Side-to-side anastomotic connector 10 of FIG. 1 includes both a first portion or flexible member, membrane or flange 12 and a second portion or flexible member, membrane or flange 14 connected by a flow channel 16 which extends between the two flanges to provide fluid communication between the vessels into which flanges 12 and 14 are inserted. In this embodiment, each flange 12, 14 has a rectangular contact surface which, when in a constricted condition along the longitudinal axis of the flange, has a semi-cylindrical configuration. In all embodiments, the two flanges may have the same size and/or shape or may have different sizes and/or shapes and the flow channel may be positioned normal to or non-normal to, (i.e., at an angle with) the flanges.

The dimensions of the flanges may vary, for example for devices suitable for use in CABG anastomosis procedures, the contact surface of the first and second segments has a surface area that is generally in the range from at least about 40 mm$^2$, usually at least about 70 mm$^2$ and more usually at least about 90 mm$^2$, and usually no greater than about 450 mm$^2$ (such as for use in the aorta or other large lumen). The thickness of the first and second segments is generally in the range from about 100 to 500 microns and preferably in the range from about 200 to 400 microns. The width typically ranges from about 15% to about 100% of the target conduit, usually from about 25% to about 85% and more usually from about 50% to about 75% in those embodiments that are not configured as complete cylinders. Exemplary width and length (or diameter) dimensions for these surface area ranges are generally from about 5 mm to about 15 mm for the width and from about 8 mm to about 30 mm for the length. And more usually from about 7 mm to about 9 mm for the width and from about 13 mm to about 15 mm for the length, depending on the exact size of the target vessel to be anastomosed.

FIG. 2A illustrates a perspective side view of another side-to-side anastomotic connector 20 having a first portion or flange 22 having a petal configuration and a second portion or flange 23 having a petal configuration. Flanges 22 and 23 are connected by a flow channel 24 which extends between the two flanges to provide fluid communication between the vessels into which flanges 22 and 23 are inserted. The cross-sectional diameter of the flow channel is chosen with respect to the particular anastomosis procedure at hand and, as such, will vary. Typically, the cross-sectional diameter of flow opening 24 is at least about 1 mm, and usually ranges from about 1.0 mm to about 10 mm or more, more usually from about 1.75 mm to about 8.0 mm and more usually from about 2.25 mm to about 7.25 mm, where such dimensions are exemplary only and are in no way intended to limit the scope of the invention. For example, in certain embodiments, flow openings having a cross-sectional diameter less than about 1 mm may be employed. As mentioned above, the first and second flanges may be of the same shape and/or have the same dimensions, or may have different shapes and/or dimensions.

Side-to-side or end-to-end distances of the flanges designated by arrows 26 and 28, shown in the top perspective view of anastomotic connector device 20 in FIG. 2B, may be the same or differ from each other. Typically, the width of each flange ranges from about 25% to about 85%, more usually from about 50% to about 75%, of the circumference of the vessel into which the particular flange is deployed. In certain embodiments, the flanges may have a major axis, such as defined by arrows 26, and a minor axis, such as defined by arrows 28. The distance across the major axis may range from about 8 mm to about 30 mm, and more typically range from about 13 mm to about 15 mm. The distance across the minor axis may range from about 5 mm to about 15 mm, and more typically range from about 7 mm to about 9 mm. The flanges are bendable or foldable about either axis, and thus, device 500 may be delivered in a folded or bent or compressed configuration such as by folding or bending about one or both axes, as required by the surgical application.

FIG. 3 illustrates an end-to-side anastomotic connector 30 having a first portion, membrane or flange member 32 having an oval shape and a second portion or tubular member 36 joined together at a flow opening, defined externally by juncture 34, analogous to that found in the side-to-side devices described above. The flange member 32 of the end-to-side device has the same or similar properties and advantages as described above with respect to the flange members of the side-to-side device. Flange 32 is shown as a partial cylinder having an elliptically shaped contact surface, however any suitably shaped flange member may be employed.

Tubular member 36 may be normal to, or positioned at an angle relative to, the surface of flange member 32. Tubular member 36 is designed to fit inside of the transected end of a graft vessel that is to be joined to the side of a host vessel. The length of tubular member 36 typically ranges from about 10 mm to about 20 mm. The outer diameter of tubular member 36 has a dimension that approximates the inner diameter of the graft vessel to be attached, and therefore is typically in the range from about 2 mm to about 6 mm, and more typically from about 3 mm to about 5 mm. Optionally, tubular member 36 has a vessel securement means 38 for further securing tubular member 36 within a graft vessel. As shown here, vessel securement means 38 is in the form of two parallel rings surrounding the circumference of tubular member and appropriately positioned vis-a-vis the host vessel, another component of the securement means such as a cuff or ring (not shown) may be temporarily or permanently positioned about the graft vessel and within the spacing formed by the parallel rings.

The above-referenced anastomosis devices are advantageously compressible, bendable or foldable from an original state in order to be delivered through a small hole or incision in the target vessels. However, the physical properties of the materials used in such devices may require that the devices are packaged/stored in an unconstrained or unstressed, i.e., original, configuration, and then loaded into a delivery system in the operating theater to minimize the occurrence of permanent deformation or plastic deformation of the devices. Discussion of device loading and deployment will follow a description of the subject delivery devices.

Delivery Devices and Systems of the Present Invention

As summarized above, the subject invention provides anastomotic delivery devices and systems. In general, the devices and systems include an anastomotic connector delivery and deployment assembly that includes at least one deployment member for flange deployment, fluid channel expansion and stabilization of an anastomotic connector at a target site. The deployment member of the subject invention may take the form of an inflatable member or an expandable member, described in greater detail below. Delivery and deployment assemblies of the present invention may include one or more inflatable deployment members, one or more expandable deployment members or may include one or more inflatable deployment members and one or more expansion deployment members.

In further describing the subject devices and systems, delivery and deployment devices and systems that include one or more inflatable deployment members are described first, followed by a description of methods of using the same. Next, delivery and deployment devices and systems that include one or more expandable deployment members, and methods of using the same are described. Finally, delivery and deployment devices and systems that include at least one inflatable deployment member and at least one expandable deployment member are described, followed by a description of kits for use in practicing the subject methods.

Inflatable Deployment Member Delivery Devices and Systems

Referring now to FIGS. 4A, 4B, 4C and 4D, the components of an anastomosis system that includes at least one inflatable deployment member according to the present invention are shown. In general, such anastomosis system includes a vessel access assembly 50, shown in FIG. 4A, an anastomotic connector delivery and deployment assembly 70, shown in FIG. 4B and an anastomotic connector loading cuff 130, shown in FIGS. 4C and 4D, configured to be used with the anastomotic connector delivery and deployment assembly 70. Vessel access assembly 50 is used to gain access to a target site in the body and, when access is established, to guide anastomotic connector delivery and deployment assembly 70 to the target site. Prior to delivery of an anastomotic connector to the target site, the anastomotic connector is operatively loaded on delivery and deployment assembly 70 by means of loading cuff 130. Each of these system components is now described in detail.

Vessel Access Assembly

Figure 4A:
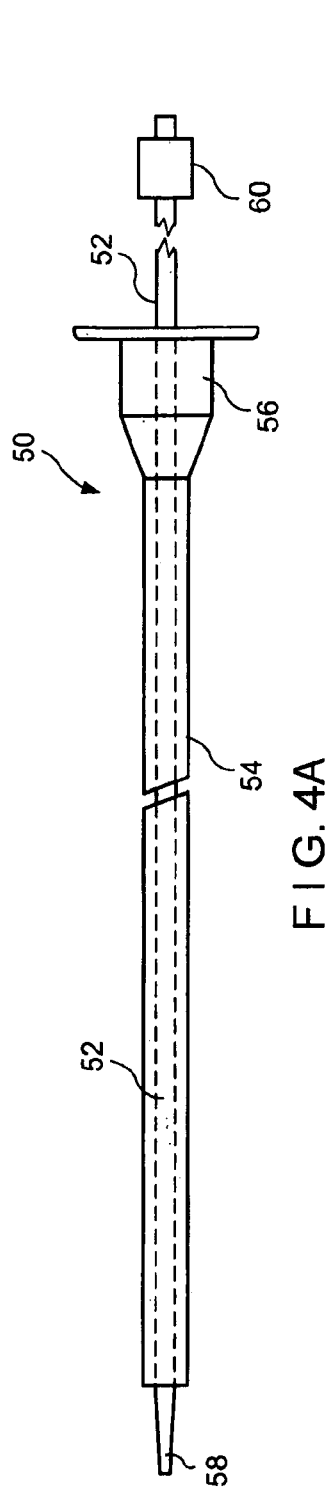

Vessel access assembly 50, as shown in FIG. 4A, includes an introducer or dilator member 52 slideably disposed and translatable within the lumen of a sheath 54. As shown, dilator 52 typically includes a tapered end portion 58 at its distal end and a hub 60 at its proximal end. Distal end 58 of dilator 52 may be relatively flexible but is sufficiently rigid to facilitate dilatation of the incision or arteriotomy site within which the anastomotic connector is to be delivered. Dilator 52 also includes a guidewire or guide catheter lumen (not shown) that extends the length of the dilator, from hub or luer 60 through distal end portion 58.

Dilator 52 has an overall length which is greater than that of sheath 54 such that the tapered distal end portion 58 of dilator 52 can be extended beyond the distal end of sheath 54 when disposed within sheath 54. Their respective lengths and other dimensions will depend on the application at hand, i.e., whether the delivery procedure is performed through a conventional surgical incision, a small port or percutaneously (a catheter-based approach), etc. Generally, however, their respective lengths range from about 5 cm to about 75 cm, and more typically from about 15 cm to about 35 cm for dilator 52; and from about 5 cm to about 60 cm, and more typically from about 10 cm to about 30 cm for sheath 54. The diameter of the dilator typically ranges from about 1.5 mm to about 6 mm, and more typically ranges from about 2 mm to about 4 mm. The sheath has an internal diameter that is generally slightly greater than the outer diameter of the dilator or is otherwise sufficiently sized to accommodate a dilator disposed therein and other components of the subject system as will be described below. The outer diameter of the sheath generally ranges from about 0.2 mm to about 1 mm greater than the diameter of the dilator. Such lengths are exemplary only and are in no way intended to limit the scope of the invention.

Anastomotic Connector Delivery and Deployment Assembly

Anastomotic connector delivery and deployment assembly 70 of the present invention includes an anastomotic connector engagement member 72 and an anastomotic connector retaining member 74 wherein engagement member 72 is translatable within the lumen of retaining member 74.

Engagement member 72 has an anastomotic connector deployment mechanism having at least one inflatable deployment member or balloon 76 positioned at distal end of a shaft 78. The inflatable member(s) are capable of flange deployment, anastomotic connector fluid channel expansion and anastomotic connector stabilization at a target site as will be described in greater detail below. Positioned at the proximal end of shaft 78 is Y-luer fitting 86 having a primary portion 88 and a side arm 90, both defining at least one lumen therein in fluid communication with corresponding lumens within shaft 78.

Shaft 78 is configured to facilitate placement and positioning, i.e., maneuvering, of the inflatable member(s) 76 to and at the target site. Accordingly, shaft 78 is of appropriate stiffness and flexibility to accomplish this task. In many instances, shaft 78 may be of variable stiffness such that a portion, e.g., the proximal portion, thereof may be relatively stiff or rigid with respect to one or more other portions, e.g., the distal portion 85, which may be less stiff or rigid, even flexible, and which may be capable of providing strain relief to shaft 78. To provide flexibility and strain relief, distal portion 85 may be made of a flexible material, such as a soft, rubbery polymer. As such, portions of shaft 78 may be made of different materials, have different dimensions, etc., with respect to one another, to achieve a variable or decreasing stiffness or strain relief along the shaft 78. Suitable materials for shaft 78 (excluding any strain relief portion) include, but are not limited to, titanium, stainless steel, polyamide, polyimide, polycarbonate, PEEK, PET, fluorinated polymers, and the like.

The dimensions of shaft 78 are not important to the subject invention and are usually selected as a function of the target site within the body, the dimensions of the anastomotic connector employed, the dimensions of the other system components, and the like. Typical dimensions for shaft 78 are as follows and are provided for exemplary purposes only and are in no way intended to limit the scope of the invention. The overall length of shaft 78 from inflatable member 76 to luer fitting 86 may be in the range from about 10 cm to about 75 cm or more, usually from about 20 cm to about 60 cm and more usually from about 20 cm to about 50 cm. The inner diameter typically ranges from about 0.010 inches to about 0.060 inches, and is usually from about 0.018 inches to about 0.050 inches. In certain embodiments, there is an optional taper of the outside diameter such that the shaft decreases in outer diameter from the proximal to the distal end.

FIG. 5A shows an enlarged view of the distal end of engagement member 72 including inflatable member 76. In this particular embodiment, shaft 78 provides two lumens, a first lumen 80 for accommodating a guiding device such as a guidewire or guide catheter (herein referred to as a guidewire lumen for sake of convenience only) and a second lumen 82 for supplying an inflation medium for inflating and deflating inflatable member 76. FIG. 5B shows a cross-sectional view taken along lines B-B of Fig., and, as best shown in FIG. 5B, guidewire lumen 80 is centrally positioned relative to shaft 78 and inflatable member 76, and inflation lumen 82 is concentric about guidewire lumen 80. Both lumens extend through the entire length of deployment member 70. Guidewire lumen 80 extends distally within inflation member 76 to a distal end port 84 and extends proximally to within the lumen of the primary portion 88 of Luer 86 and terminates at guidewire port 92. At least the portion of guidewire lumen 80 extending through inflatable member 76 is formed by flexible shaft portion 85 which provides some structure to inflation member 76. Inflation lumen 82 extends distally to within, and is in fluid communication with, the interior of inflatable member 76. Lumen 82 extends proximally to within the lumen of side arm 90 and terminates at an inflation port 92. In certain embodiments, the guidewire lumen may be omitted, as shown in FIG. 5C, such that a solid core may be provided in place thereof.

Alternatively, one or both lumens 80 and 82 may be positioned laterally with respect to each other within shaft 78. Still yet, one or more of the lumens may be situated along the length of the periphery or exterior of engagement member 72. With respect to guidewire lumen 80, such a configuration is commonly referred to as a rapid exchange configuration. Such configurations for the "rapid exchange" of guidewires are well known in the art and will not be described herein. In other words, the lumens need not be concentrically aligned with respect to each other and may be adjacent or otherwise off-set with respect to each other. It will be understood that, while the subject invention will be described herein with respect to a guidewire lumen 80 that extends within the entire length of engagement member 72, the subject devices may be modified to include alternative guidewire/guide catheter lumen configurations, such as the rapid exchange configuration, where such modifications require no more than routine experimentation.

FIG. 6 illustrates another embodiment of an anastomotic connector engagement member 100 of the present invention having a dual-balloon or dual inflatable member configuration such that two inflatable deployment members are present. In this particular embodiment, inflatable deployment members 102 and 104 are positionable side-by-side along their lengths and may be substantially parallel with each other or may define an acute angle therebetween; however other dual inflatable member arrangements are contemplated as well as will be described below. Inflatable member 102 has a configuration which is similar to or the same as inflatable member 76 of FIG. 5A, having a guidewire lumen 106 and concentric inflation lumen 108. Inflatable member 104 provides an inflation lumen 110 similar to inflation lumen 108 about a lumen 112, however, lumen 112 is non-functional and may even be a solid core to provide stability to inflatable member 104. Inflatable members 102 and 104 are held together at their proximal ends within a shaft or hypotube 114.

Each inflatable member 102, 104 may be inflated/deflated independently of the other using individual inflation/deflation ports (not shown) or the inflatable members may be inflated/deflated simultaneously through a single inflation port. Accordingly, the inflatable members 102 and 104 may extend from a single inflation lumen or each may extend from a respective inflation lumen. The two inflatable members may have the same dimensions, shape, etc., or may have different dimensions and/or shapes, etc.

The inflatable members of the present invention, whether in a singular, dual, triplet, etc., configuration, have a size, shape and dimensions which are suitable for accommodating an anastomotic connector operatively loaded thereon, i.e., the inflatable member(s) is axially positioned through the fluid channel of an anastomotic connector used therewith. As such, the size, shape and dimensions of the inflatable member(s) will vary according to a variety of factors including, but not limited to, the particular dimensions of the anastomotic connector device employed and/or particular dimensions of the conduits to be joined, etc. Exemplary suitable shapes of the inflatable members include, but are not limited to, cylindrical, round, oval, bean-shaped, conical-tipped, square-tipped, FIG.-8, barbell or dog bone-shaped (i.e., having proximal and distal protrusions), and the like, or may be of an irregular or complex shape.

Thus, an aspect of the present invention is the optimal constricting, compressing or folding of the anastomotic connectors, or portions thereof, from an original state to a compresses state and the subsequent optimal expansion, deployment or unfolding of the anastomotic connector or portions thereof. In other words, the connector is provided in an original configuration, from which it is then compressed into a non-original or compressed configuration for delivery to a target site. The connector is then deployed at the target site where it substantially returns to its original configuration from the compressed configuration to provide an anastomotic connection.

Used in any number, the one or more inflatable members of the present invention are configured so as to provide or assist in the optimal expansion, deployment or unfolding of a constricted, compressed or folded anastomotic connector including "seating" or urging the flanges of the connector up against the inner wall of the conduit in which they are deployed, taking into consideration the size and anatomy of the vessel or tissue lumen into which or outside which the connector is to be deployed or implanted. More specifically, the one or more inflatable members of the present invention serve to deploy the flanges of the anastomotic connector, expand or open the fluid channel or stoma of an anastomotic connector and stabilize the connector in a target vessel, for example during removal of the delivery assembly components (e.g., sheath 54 and/or retaining member 74) from the body after connector implantation. In certain embodiments, the expansion of the fluid channel causes the flange(s) to optimally deploy.

When more than one inflatable member is employed, the inflatable members employed may have configurations which differ from each other in size, and/or volume capacity, and/or shape and/or material. Additionally, the inflatable members may be positioned relative to each other, e.g., side-by-side, vertically juxtaposed, end-to-end, intertwined, etc. so as to optimally deploy a constrained connector. Discussed in greater detail below, the inflatable members may be made of compliant, semi-compliant or non-compliant material. When made of a compliant material, the size of the inflatable member is adjustable. When made of a non-compliant material, each inflatable member may be specifically contoured to optimally engage with an adjacent inflatable member and/or with the connector in which it is positioned. In certain embodiments, the inflatable members may be fabricated from different materials, e.g., one or more inflatable member may be made of a compliant material and one or more inflatable member may be made of a non-compliant or semi-compliant material.

FIGS. 10A-10F illustrate additional examples of various configurations of inflation mechanisms of the present invention having more than one inflatable member. The embodiments shown herein are described having two inflatable deployment members, however more or fewer inflatable deployment members are contemplated by the subject invention, e.g., more than two inflatable members such as three, four or even more than four such as five or more inflatable members may be employed. FIG. 10A shows inflation mechanism 300 having first and second inflatable members 302 and 304, respectively, wherein the members have the same shapes, i.e., cylindrical, but have different sizes and volume capacities. FIG. 10B shows another inflation mechanism 310 having side-by-side inflatable members 312 and 314. The inflatable members have the same shape, i.e., trapezoidal, and size, but are aligned head-to-toe with respect to each other. FIG. 10C illustrates another inflation mechanism 320 having a pair of inflatable members 322 and 324 having shapes and sizes different from each other. FIG. 10D illustrates another exemplary inflation mechanism 380 having two inflatable members 381 and 383 serially positioned (i.e., positioned substantially in tandem or substantially end-to-end) with respect to one another. In the embodiment shown in FIG. 10D, inflatable members 381 and 383 are shown having substantially the same or similar size, shape and volume capacities; however the two may differ in size and/or shape and/or volumetric capacities.

FIG. 10E shows an alternative embodiment of a subject inflation mechanism 317 having a single inflatable member 318 having a dog bone or barbell shape such that it includes distal protrusion 319, mid portion 313 and proximal portion 316. The distal and proximal portions may be the same shape and/or size and/or have the same volume capacities or may differ in shape and/or size and/or volume capacities.

In all embodiments, the inflatable members may have individual, respective inflation/deflation ports and/or guidewire lumens, or a single inflation/deflation port and/or guidewire lumen may be used for both inflatable deployment members.

FIG. 10F shows a transverse cross section taken through an inflation mechanism 330 having a single inflatable member 332 having a kidney bean shape. Such a configuration may be well suited where the flanges of the connector device to be deployed are relatively large or long. When operatively loaded within the delivery and deployment assembly of the present invention, the connector flanges would fold or wind around the deployment member. Inflatable member 332, when in a deflated condition, may be wound along with (while inside of) the flanges. The kidney bean shape of the inflatable member 332 facilitates this collective winding and the subsequent unwinding or unfolding of the flanges when the inflatable member 332 is inflated. Additionally, the action of inflating the inflatable members easily "unkinks" or unfolds, i.e., expands, the constrained fluid channel or stoma of the connector device to provide a completely expanded or open fluid channel that does not have a kink, bend or fold therein.

FIG. 10G illustrates a transverse cross-section taken through another dual-member inflation mechanism 340 having inflatable members 342 and 344. The collective configuration of the inflatable members when inflated, also provides a profile similar to that of single, kidney bean-shaped inflation member 332 of FIG. 10F, and thus provides similar functional properties to facilitate the optimal folding and unfolding of an anastomotic connector.

In general, the length of a single inflatable member and/or the combined length of two or more inflatable members (e.g., if present in an off-set or serial configuration) is usually at least as long as the length of the fluid channel of the anastomotic connector employed, and typically the length is longer than that of the fluid channel of the anastomotic connector employed so as to provide an outward force to the flexible member(s) of the anastomotic connector upon deployment in a vessel, as well as to provide stability to the anastomotic connector during the implantation process.

In an inflated state, at least a portion of an inflatable member or members (where the more than one members are tangentially positioned with respect to each other, i.e., side-by-side) has an outer diameter or transverse dimension at least as great as the diameter of the fluid channel of the anastomotic connector.

Accordingly, the length of a single exemplary inflatable member may range from about 3 mm to about 30 mm, usually from about 6 mm to about 20 mm and more usually from about 8 mm to about 15 mm, and at least a portion of an exemplary inflatable member or members has an outer diameter in an inflated state that typically ranges from about 2.5 mm to about 11 mm, usually from about 3 mm to about 8.5 mm. For example, in those embodiments having two inflatable members serially (i.e., substantially in tandem or substantially end-to-end) positioned relative to each other, the length of the distal inflatable member may range from about 2 mm or 3 mm to about 20 mm and the outer diameter of the distal inflatable member may range from about 2 mm to about 10 mm, usually from 2 mm to about 8 mm. The length of the proximal inflatable member may range from about 3 mm to about 30 mm, usually from about 6 mm to about 20 mm and the outer diameter of the proximal inflatable member usually ranges from about 2.5 mm to about 11 mm, usually from about 3 mm to about 8.5 mm. The dimensions described above are exemplary and are in no way intended to limit the scope of the invention.

The inflatable members of the subject invention may be formed of suitable non-compliant, semi-compliant (hybrid compliant) or complaint material(s), depending on the particular procedure at hand, where suitable materials include, but are not limited to, polymeric materials such as elastomers, polyethylene, polycarbonate, nylons, PET, nylon copolymer, polyamide, polyisoprene, silicone rubber, latex, polyurethane, and the like may be used. Of interest is the use of high durometer urethane or Pebax®. One or more optional radio-opaque marker (not shown) may be present on inflatable member 76 to facilitate visualization of the inflatable member and placement thereof. For example, one marker may be positioned at the distal end of the inflatable member and another marker may be positioned at the proximal end of the inflatable member. The one or more markers may be in the form of bands, coils or other radio-opaque markers or markings known in the art. Markers of this type are typically made of materials such as platinum, gold, etc., and various related alloys, and other suitable radio-opaque materials such as barium sulfate, bismuth trioxide, bismuth carbonate, powdered tungsten, powdered tantalum or the like.

Referring now to FIG. 7, at the proximal end of anastomotic connector engagement member shaft 78 is Y-luer fitting 86 having guidewire port 94 in communication with guidewire lumen 80 which is capable of accommodating a guidewire. Side arm 90 of fitting 86 provides an inflation/deflation port 92 in fluid communication with inflatable member 76 via inflation lumen 82. Extending from inflation/deflation port 92 is inflation/deflation line or tube 96 which is in communication with an inflation system 98 which provides a source of air, saline, or other appropriate medium for inflating the one or more inflatable members of the subject device. Inflation system 98 may have any suitable configuration such as syringe pair 98a, 98b and a three-way stopcock 99. Initially, syringe 98a contains the inflation medium while syringe 98b is empty. When stopcock 99 is adjusted such that it creates an open pathway to syringe 98a and a closed pathway to syringe 98b, syringe 98a is depressed, causing the inflation medium to enter into Luer fitting 86 through port 92 and into inflation lumen 82. To deflate the inflatable member, stopcock 99 is adjusted to close the pathway to syringe 98a and to open the pathway to syringe 98b. Drawing back on the handle of syringe 98b creates a negative pressure wherein the inflation medium is drawn out of the inflation member and into syringe 98b. Both syringes may be gradually depressed and withdrawn so as to selectively adjust the volume of the inflation medium within the inflatable member(s) and thereby selectively inflate/deflate the inflation member(s).

Figure 4B:
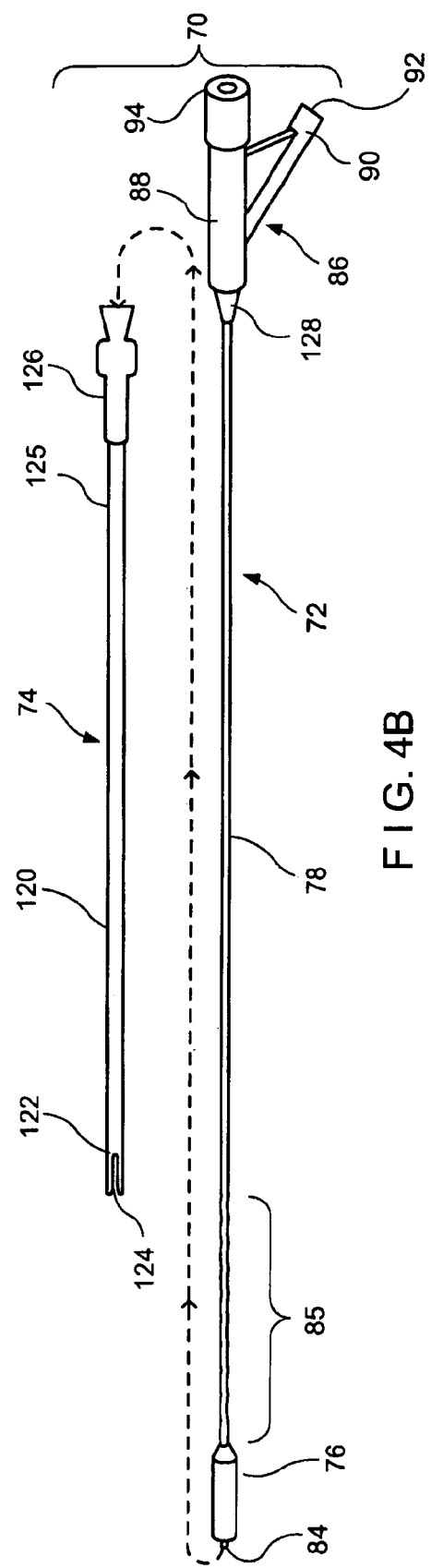

As mentioned above, anastomotic connector engagement member 72 is configured to be slideably engaged and translatable within connector retaining or holding member 74 (see FIG. 4B). Retaining member 74 includes a tube 120 having a distal end 122 and a proximal end 125 having a hub 126. Hub 26 and the lumen of tube 120 are configured to accommodate anastomotic connector engagement member 72 coaxially therein. A feature of retaining member 74 is the presence of anastomotic connector grasping slit, notch or slot 124 positioned at distal end 122. Alternatively, more than one slit may be provided. For example, two slits may be provided diametrically opposed from each other. Slit 124 extends from the distal opening of tube 120 a short along the length of tube 120. Slit 124 is dimensioned to retain an anastomotic connector device therein by grasping and holding a portion of the anastomotic connector between the edges of the slit. The length of slit 124 is not important to the subject invention, so long as it is able to operatively hold an anastomotic connector therein. Typically, slit 74 ranges in length from about 1 mm to about 10 mm, usually from about 3 mm to about 7 mm, where such dimensions are exemplary only and are in no way intended to limit the scope of the invention. In embodiments with more than one slit, the slits may have different lengths to accommodate connectors of different sizes.

The dimensions of retaining or holding member 74 are typically chosen with respect to the dimensions of other components of the system, the location of the anastomosis, the size of the anastomotic connector employed, etc. The total length of tube 120 from hub 126 to the distal tip is such that it is less than the length of shaft 78 of engagement member 72 so that when engagement member 72 is disposed within retaining member 74 and hub 125 is positioned to abut luer fixture 86, a distal portion of deployment element 60 protrudes from the distal end of tube 120. The inner diameter of retaining member 74 is dimensioned to snugly accommodate engagement member 72 therein. The outer diameter of retaining member 74 is such that retaining member 74 is capable of being slideably disposed and translatable within a loading cuff 130, illustrated in FIGS. 4C and 4D.

Holding member 74 may be fabricated from a variety of materials, where the materials are generally flexible materials such that when positioned over the inflatable member(s) in an inflated condition, the area of tubing 120 around about slit 124 is capable of being flexed or biased outward, away from the inflatable member(s) to allow expansion and deployment of an anastomotic connector retained by retaining member 74. Suitable materials for use in fabricating retaining member 70 include, but are not limited to titanium, stainless steel, polyamide, polyimide, polycarbonate, PEEK, PET, fluorinated polymers, and the like.

Loading Cuff

As shown in FIG. 4C and as briefly mentioned above, the subject system also includes a loading cuff 130. Loading cuff 130 includes a sleeve 132. In this particular embodiment, loading cuff 130 includes a split 134 along the entire length of tube 132, however, a split may not be present along the entire length of the tube, e.g., the split may begin at the distal end and terminate prior to the proximal end or may be omitted all together. In the embodiment shown in FIG. 4C, split 134 terminates prior to the proximal end of the tube. FIG. 4D shows an alternative embodiment of loading cuff 130 having a cut-out 131 at the distal end thereof for accommodating a portion of an anastomotic connector and more specifically the portion of a connector that this held by the slit of the retaining member. The cut out assists in optimally compressing or folding an anastomotic connector for delivery to a target site. In all embodiments, provided at a proximal end portion of sleeve 132 is a sheath stop 138 and gripping element 136, herein shown configured as finger grips, where such will typically be ergonomically designed for comfort and ease of use. Sleeve 132 has a diameter less than the diameter of hub 126 of retaining member 74 such that sheath stop 136 is caused to abut hub 126 when contacted therewith. The split sleeve configuration of loading cuff 130 allows it to be easily and readily peeled away from holding member 74. However, the loading cuff may be removed from the holding member 74

The dimensions of loading cuff 130 will vary depending on the dimensions of other components of the system, the location of the anastomosis, the size of the anastomotic connector employed, etc. The total length of loading cuff 130, from finger grips 136 to the distal tip is such that it is typically less than the length of holding member 74.

Loading cuff 130 may be fabricated from a variety of materials. Suitable materials for use in fabricating loading cuff 130 include, but are not limited to titanium, stainless steel, polyamide, polyimide, polycarbonate, PEEK, PET, fluorinated polymers, and the like.

The subject anastomosis system may further include viewing means (not shown), such as an endoscope, associated with it to facilitate visualization by the physician of the working space. Such is particularly helpful if performing the procedure through a thoracotomy, mini-thoracotomy, mini-sternotomy or through an access port formed in the patient's chest.

Methods of Using the Subject Inflatable Deployment Member Devices and Systems

The methods of the present invention involve forming an anastomosis between two or more conduits or vessel lumens. Specifically, the methods involve connecting a graft vessel to at least one target vessel, where the target vessel is typically located within the body. Suitable applications of the subject anastomotic methods include coronary artery bypass grafting, peripheral artery bypass grafting, the formation of arteriovenous fistulae, and the like. The subject methods employ active deployment of an anastomotic connector to accomplish an anastomotic connection between conduits such as vessel lumens. That is, an anastomotic connector is provided in an original configuration, operatively compressed from the original configuration, delivered to and positioned at the target site, expanded so that it substantially returns to its original configuration and stabilized using the devices of the subject system.

The graft vessel may be a pedicled vessel requiring only distal attachment to the target vessel or may be a segmented vessel which requires both proximal and distal attachment. The subject devices and methods may be used to perform both proximal and distal anastomosis of the same graft vessel wherein the proximal procedure and the distal procedure may be performed in any order. For example, a segmented graft vessel may be anastomosed proximally to a blood supply vessel, such as the aorta, using either a side-to-side or an end-to-side connector device. The same vessel may then be anastomosed distally to the target vessel using either type of anastomotic connector device as well.

The subject methods may be employed in an open surgical approach in which the physician directly visualizes the surgical field or in a less invasive approach wherein the physician must use an endoscope or the like to visualize the surgical field. Such less invasive methods may be performed through a small incision or port, or intravascularly wherein the subject delivery devices are configured as catheters.

The subject methods for forming a side-to-side anastomosis and an end-to-side anastomosis using the subject inflatable deployment member devices and systems are now described separately.

Side-to-Side Anastomosis

FIGS. 8A-8H illustrate the steps for delivering and implanting a side-to-side anastomotic connector to join a graft vessel with a target vessel. For purposes of illustrating an example of a side-to-side anastomotic method of the present invention, the anastomotic connector of FIG. 2 and the dual-balloon inflatable expansion mechanism of FIG. 6 are used; however, such example is not intended to be limiting as any suitable connector configuration and number of inflatable members, within the scope of the accompanying claims, may be used to carry out the subject methods.

Figure 8A:
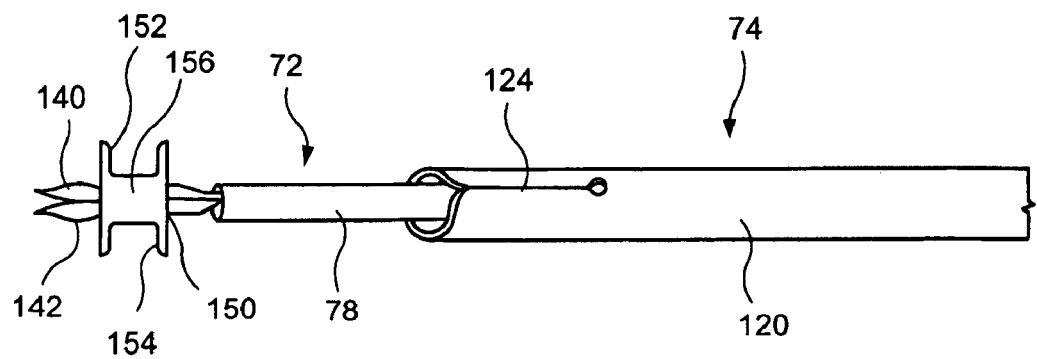
Figure 8B:
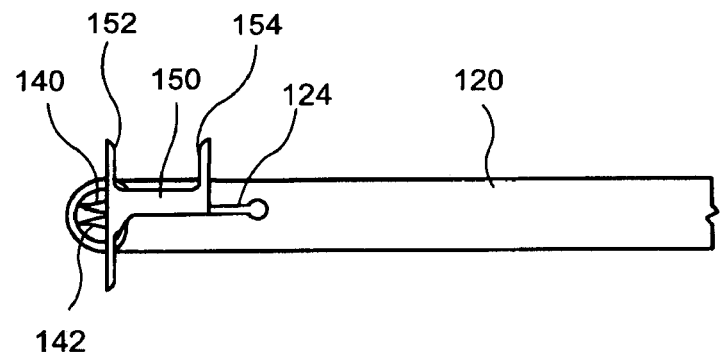

Prior to delivering an anastomotic connector to the target site, the connector must first be properly loaded onto anastomotic connector delivery and deployment assembly 70. As shown in FIG. 8A, a delivery system is provided that includes anastomotic connector engagement member 72 having side-by-side inflatable members 140 and 142, shown in a deflated state, and which is slideably translatable within holding member 74. An anastomotic connector device 150 in an original configuration, i.e., not compressed, having distal flange member 152 and proximal flange member 154, is slid over deflated inflatable members 140 and 142 such that inflatable members 140 and 142 are positioned through fluid channel 156 of connector 150. Anastomotic connector device 150 is translated proximally over the distal end of engagement member 72 and is caused, typically manually, to enter into slit 124 of retaining member 74. Connector 150 is pushed into slit 124 until distal flange 152 abuts or is relatively in close proximity to the distal edge of retaining member 74. As such, connector 150 is securely grasped or held in slit 124 with a portion contained within tube 120 of holding member 74 and another portion extending radially outside of tube 120. Once anastomotic connector device 150 is held securely in slit 124, holding member 74 and connector device 150 are translated distally over the shaft 78 of engagement member 72 so as to be positioned over deflated inflatable members 140 and 142, i.e., fluid channel 156 of anastomotic device 150 is positioned over the deflated inflatable members, as shown in FIG. 8B.

Figure 8C:
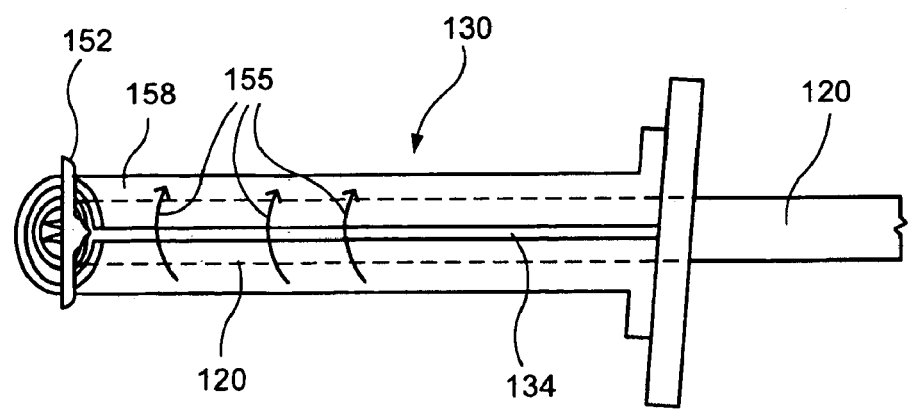

Next, as shown in FIG. 8C, the deployment assembly and retained connector 150 are inserted into the proximal end of loading cuff 130 (in certain embodiments, loading cuff 130 may be positioned over retaining member 74 prior to positioning anastomotic connector device 150 over the deflated inflatable members) and translated distally therein until the distal tip of the loading cuff 130 is aligned with the distal tip of retaining member 74, such that distal flange 152 of connector 150 continues to remain exposed. As such, the portion of the anastomotic connector device 150 extending from slit 124 is now covered by loading cuff 130. As mentioned above, cuff 130 may include a cut-out at the distal end thereof which is dimensioned to accommodate a portion of an anastomotic connector. In such instances, the cut-out of the loading cuff is positioned over the portion of the connector held in slit 124 of the retaining member to facilitate the folding and compressing of the connector into an optimally compressed state for deployment, as described below.

In either case, to compress or fold the connector into an optimum configuration for delivery and deployment from the original configuration, loading cuff 130 is held steady in a fixed position and retaining member 74 is rotated within loading cuff 130. This rotation motion, illustrated by arrows 155, results in the outwardly extending portion 158 of anastomotic connector device 150 being sandwiched between tube 120 and loading cuff 130. Also, such portion 158 is now constrained, compressed or folded against tube 120 of retaining member 74 in an optimal position and configuration for subsequent deployment. The collectively engaged retaining member 74 and loading cuff 130 with anastomotic connector 150 operatively loaded therewith, are now ready to be loaded into vessel access sheath 54 for deployment at the target site within the body.

Either prior to, during or after the connector loading procedure described above, access is made at the target vessel. Such target vessel access may be accomplished using any convenient protocol, e.g., by a small incision, i.e., an arteriotomy, made in the target vessel or by the Seldinger technique or a modification thereof. With the Seldinger technique, a small gauge needle is introduced through the wall of the target vessel, e.g., a coronary artery, and a guidewire is introduced through the needle and delivered within the target vessel. After proper placement of the guidewire, the needle is withdrawn and the distal end of the guidewire is left in place within the target vessel.

Figure 8D:
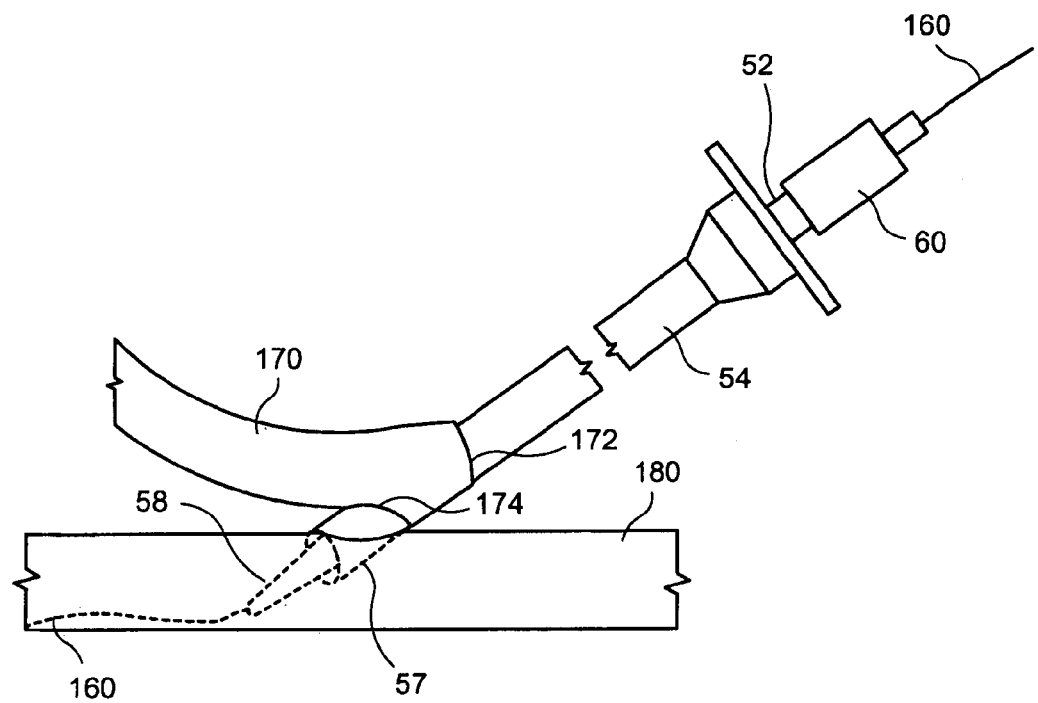

Prior to introducing the vessel access assembly 50 over the guidewire 160, a graft vessel 170 having a transected end 172 is provided. A small opening 174 is made within the side wall of graft vessel 170 close to transected end 172 with enough length there between such that the vessel can be tied off. As shown in FIG. 8D, the distal end 57 of sheath 54 is inserted into graft vessel 170 through transected end 172 and back out of graft vessel 170 through side opening 174.

Once the access site has been established and a guidewire 160 is operatively positioned at the access site, vessel access assembly 50 (dilator and sheath), with graft vessel 170 positioned over the distal end 57 of sheath 54, is then delivered over guidewire 160 to the access site within target vessel 180 such that the tapered distal end 58 of dilator 52 is caused to penetrate through and dilate the wall of target vessel 180. Dilator 52 is then proximally withdrawn from sheath 54 by slideably translating dilator 52 in a proximal direction over the guidewire. In certain embodiments, guidewire 160 may now be removed from the site, or it may be left in place. The subject invention will be further described with respect to an embodiment wherein the guidewire is left in place at the site, where such illustration is for exemplary purposes only and is not intended to limit the scope of the invention. At this point, graft vessel 170 may be positioned such that the edge of its side wall opening 174 substantially engages with or is in apposition against the edges of the opening formed within target vessel 180 or may be positioned a distance from the opening.

Figure 8E:
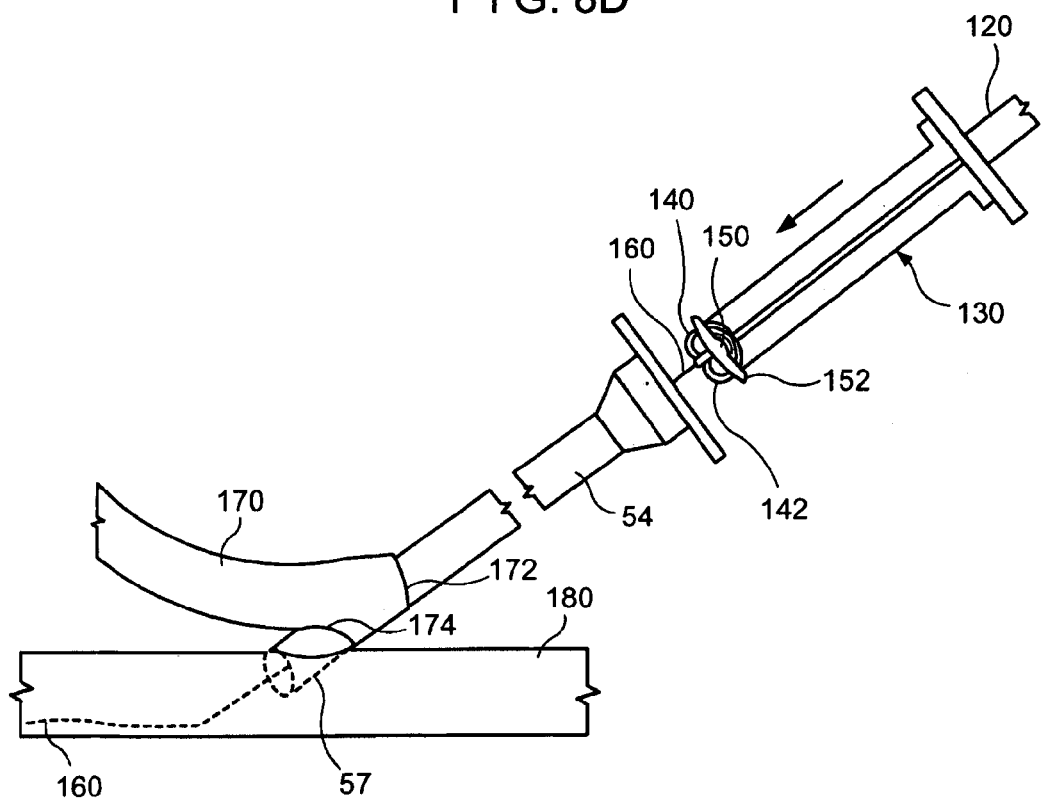

The collectively engaged anastomotic connector delivery and deployment assembly 70 and loading cuff 130 with anastomotic connector 150 operatively loaded therewith, as illustrated in FIG. 8E, are now inserted into the proximal end of sheath 54 over guidewire 160. In this manner, the distal flange maintains its compressed configuration inside the sheath. Anastomotic connector delivery and deployment assembly 70 is advanced distally such that anastomotic connector device 150 operatively loaded thereon, as described above, is moved out of loading cuff 130. The loaded connector 150 retains its optimally constrained or compressed condition as it is now retained by vessel access sheath 54. While the loading cuff sleeve 132 is caused to translate within sheath 54, its movement is stopped when stop 138 abuts the proximal end of sheath 54. Loading cuff 120 may then be completely removed by pulling on gripping element 136 (herein shown as finger grips) and causing sheath 134 of loading cuff 130 to separate along slit 134 or may be removed by using an appropriate tool such as a cutting tool or the like. In certain embodiments, loading cuff 130 may remain engaged with the system, but moved out of the way by sliding it a sufficient distance in a proximal direction.

Anastomotic connector delivery and deployment assembly 70 is further advanced distally so as to protrude a distance from the distal tip of sheath 54 in the interior of vessel 180 or the sheath may be advanced proximally. As shown in FIG. 8F, this secondary advancement places the first or distal flange member 152 of connector 150 within vessel 180 such that it substantially returns to its original configuration within the vessel. To fully deploy flange member 152 and add to distal stability, inflatable deployment members 102 and 104 are inflated by proper adjustment of inflation source 98 as described above with reference to FIG. 7. In inflated states, inflatable members 102 and 104 expand to push flange member 152 against the internal wall of the target vessel, as shown in FIG. 8F. Accordingly, inflation of balloons 102 and 104 applies a stabilizing force to connector 150 and helps to retain connector 150 in a substantially fixed position relative to the vessel and/or may assist in optimally positioning the device. In this manner, the position of distal flange member 152 is maintained upon deployment of proximal flange 154 and expansion of fluid channel 156, and removal of the components of the system from the body after connector 150 has been fully deployed.

Once distal flexible member 152 is engaged with the internal vessel wall of vessel 180 and held in that position by the stabilizing force applied by the inflated inflatable members 102 and 104, the fluid channel of the connector is expanded such that it substantially returns to its original configuration and proximal flange 154 is deployed such that it is expanded and substantially returns to its original configuration in the following manner. Sheath 54 and deployment assembly 70 are retracted proximally so that their respective distal tips are positioned adjacent the outer wall of target vessel 180, wherein the distal flange is held in a stabilized position by the inflatable members, as mentioned above. Next, graft vessel 170 is positioned such that the edge of its side wall opening 174 substantially engages with or is in apposition against the edges of the opening formed within target vessel 180. With graft vessel 170 in apposition to target vessel 180, sheath 54 is retracted proximal to slit 124 and inflatable members 102 and 104 are further inflated thereby outwardly flexing the portion of tube 120 about slit 124. As such, proximal flange member 154 and fluid channel 156 are deployed or expanded out of or away from retaining member 74, as shown in FIG. 8G, such that they assume an expanded or unconstricted or unfolded configuration, i.e., they substantially return to their original configurations. Retaining member 74 is retracted proximally out of graft vessel 170 and additional pressure is applied to inflatable members 102 and 104 to inflate further, if required. The deployment of second or proximal flange member 154 is the same as that described with respect to the deployment of the first or distal flange member 152 except that proximal flange member 154 expands against the internal wall of graft vessel 170 and the expansion of inflatable members 102 and 104 cause fluid channel 156 to fully expand or open by applying an outward force to the interior of the fluid channel. The respective openings of graft vessel 170 and target vessel 180 now encircle fluid channel 156 thereby pulling together to maintain contact between their respective edges. Preferably, the endothelial linings of the vessels are in intimal contact with each other so as to promote natural tissue bonding between them. The internal vessel pressures cause the respective flanges to seal against the adjacent vessel wall surface, thereby preventing the escape of fluid, e.g., blood, from the vessel openings.

Accordingly, a graded inflation process, i.e., inflation of the inflatable members in a series of inflation steps, may, although not always, be employed to deploy the anastomotic connector. That is, the anastomotic connector is deployed by serially inflating the inflatable member(s) such that a first inflation deploys the distal flange and, once the distal flange is deployed and stabilized, a second inflation deploys the proximal flange and expands the fluid channel. After this second inflation such that both flanges are deployed and stabilized by the inflatable member(s), a third inflation may be employed to fully inflate the inflatable member(s) if not already fully inflated and fully expand the fluid channel.

Proximal and/or distal flange deployment and expansion may be accomplished at least partially if not completely by expanding the fluid channel, where such fluid channel expansion causes one or both flanges to expand to an optimum configuration and position at the target site.

In certain embodiments, multiple inflation/deflation cycles may be employed such that at one or more instances during the delivery and deployment of an anastomotic connector, the inflation members may be deflated and re-inflated one or more times. Such multiple inflation/deflation cycles may be employed during the deployment of the distal flange and/or the expansion of the fluid channel and/or the deployment of the proximal flange. Such multiple inflations may serve, in certain situations, to further stabilize the connector device, seal the flange(s) against the internal walls of the vessels, ensure full expansion of the fluid channel and expansion of the device against tissue, and/or assist in further positioning the connector device if required.

Figure 8H:
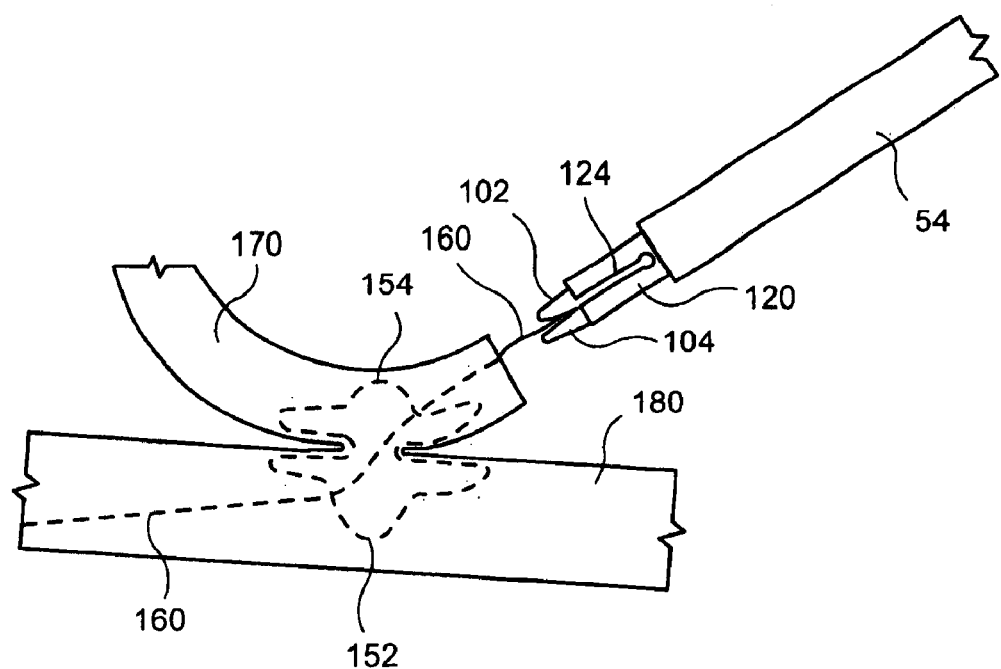

Finally, with reference to FIG. 8H, inflatable members 102 and 104 are deflated and the delivery and deployment assembly 70, including engagement member 72 and retaining member 74, and sheath 54 are retrieved over guidewire 160 followed by retrieval of guidewire 160 from within the body. Transected end 172 of graft vessel 170 must then be closed, which may be accomplished by tying it off with a suture or closing it with a clip or the like.

End-to-Side Anastomosis

FIGS. 9A-9H illustrate the steps for delivering and implanting an end-to-side anastomotic connector to join a graft vessel with a target vessel using the subject inflatable deployment devices and systems. Reference numerals that are identical to those used in connection with FIGS. 8A-8H represent the same or analogous elements or features in FIGS. 9A-9H. For purposes or illustrating an example of an end-to-side anastomotic method of the present invention, the anastomotic connector of FIG. 3 and the inflatable member of FIGS. 5A and 5B are used; however, such example is not intended to be limiting as any suitable connector and configuration of inflatable member(s), within the scope of the accompanying claims, may be used to carry out the subject methods.

Prior to delivering an anastomotic connector to the target site, the connector must first be properly loaded onto anastomotic connector delivery and deployment assembly 70. As shown in FIG. 9A, a delivery system is provided that includes anastomotic connector engagement member 72 having inflatable deployment member 76, shown in a deflated state, and which is slideably translatable within retaining member 74. An anastomotic connector device 200 in an original configuration, i.e., not compressed, having distal flange member 202 and tubular member 204 is slid over deflated inflatable member 76 which is positioned through tubular member 204. Anastomotic connector device 200 is translated proximally over the distal end of engagement member 72 and is caused, typically manually, to enter into slit 124 of retaining member 74. Tubular member 204 is pushed into slit 124 such that a portion 206 thereof extends outwards of slit 124, and until distal flange 202 abuts or is in relatively close proximity to the distal edge of retaining member 74. As such, connector 200 is securely grasped in slit 124 with a portion of tubular member 204 contained within tube 120 and another portion extending radially outside of tube 120. Once anastomotic connector device 200 is held securely in slit 124, retaining member 74 and connector device 200 are translated distally over shaft 78 of engagement member 72 so as to be positioned over deflated inflatable member 76, as shown in FIG. 9B.

Next, as shown in FIG. 9C, the deployment assembly and retained connector 200 are inserted into the proximal end of loading cuff 130 (in certain embodiments, loading cuff 130 may be positioned over retaining member 74 prior to positioning anastomotic connector device 200 over the deflated inflatable members) and translated distally therein until the distal tip of the loading cuff 130 is aligned with the distal tip of retaining member 74, such that distal flange 202 of connector 200 continues to remain exposed. As such, the portion of the anastomotic connector device 200 extending from slit 124 is now covered by loading cuff 130. As mentioned above, cuff 130 may include a cut-out at the distal end thereof which is dimensioned to accommodate a portion of an anastomotic connector. In such instances, the cut-out of the loading cuff is positioned over the portion of the connector held in slit 124 of the retaining member to facilitate the folding and compressing of the connector into an optimally compressed state for deployment, as described below.

In either case, to compress or fold the connector into an optimum configuration for delivery and deployment from the original configuration, loading cuff 130 is held steady in a fixed position, retaining member 74 is rotated within loading cuff 130. This rotation motion, illustrated by arrows 155, results in the outwardly extending portion 206 of anastomotic connector device 200 being sandwiched between tube 120 and loading cuff 130. Also, such portion 206 is now constrained, compressed or folded against tube 120 of retaining member 74 in an optimal position and configuration for subsequent deployment. The collectively engaged retaining member 74 and loading cuff 130, with anastomotic connector 200 operatively loaded therewith, are now ready to be loaded into vessel access sheath 54 for deployment at the target site within the body.

Either prior to, during or after the connector loading procedure just described, access is made at the target vessel. As discussed above with respect to the method of forming a side-to-side anastomosis connection, such may be accomplished by a small incision, i.e., an arteriotomy, made in the target vessel or by the Seldinger technique or a modification thereof.

Once the access site has been established and a guidewire 160 is operatively positioned at the access site, vessel access assembly 50 (dilator and sheath) is then delivered over guidewire 160 to the access site within target vessel 180 such that the tapered distal end 58 of dilator 52 is caused to penetrate through and dilate the wall of target vessel 180, as shown in FIG. 8D. Dilator 52 is then proximally withdrawn from sheath 54 which is left in place at the access site. . In certain embodiments, the guidewire may now be removed from the site, or it may be left in place. The subject invention will be further described with respect to an embodiment wherein the guidewire is left in place at the site, where such illustration is for exemplary purposes only and is not intended to limit the scope of the invention.

Figure 9D:
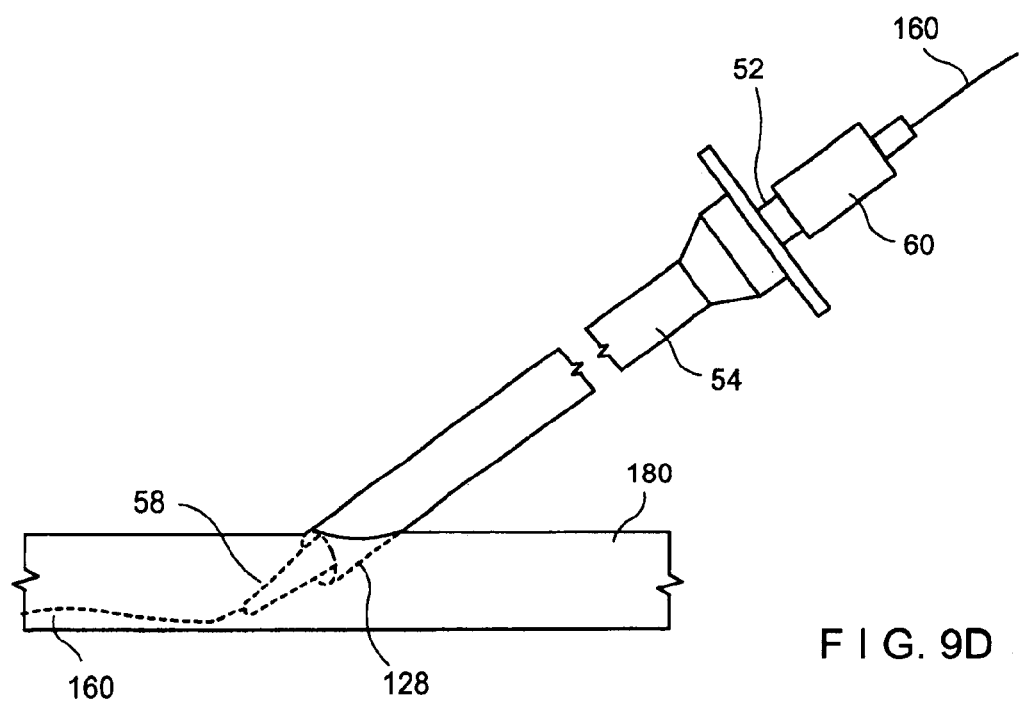
Figure 9E:
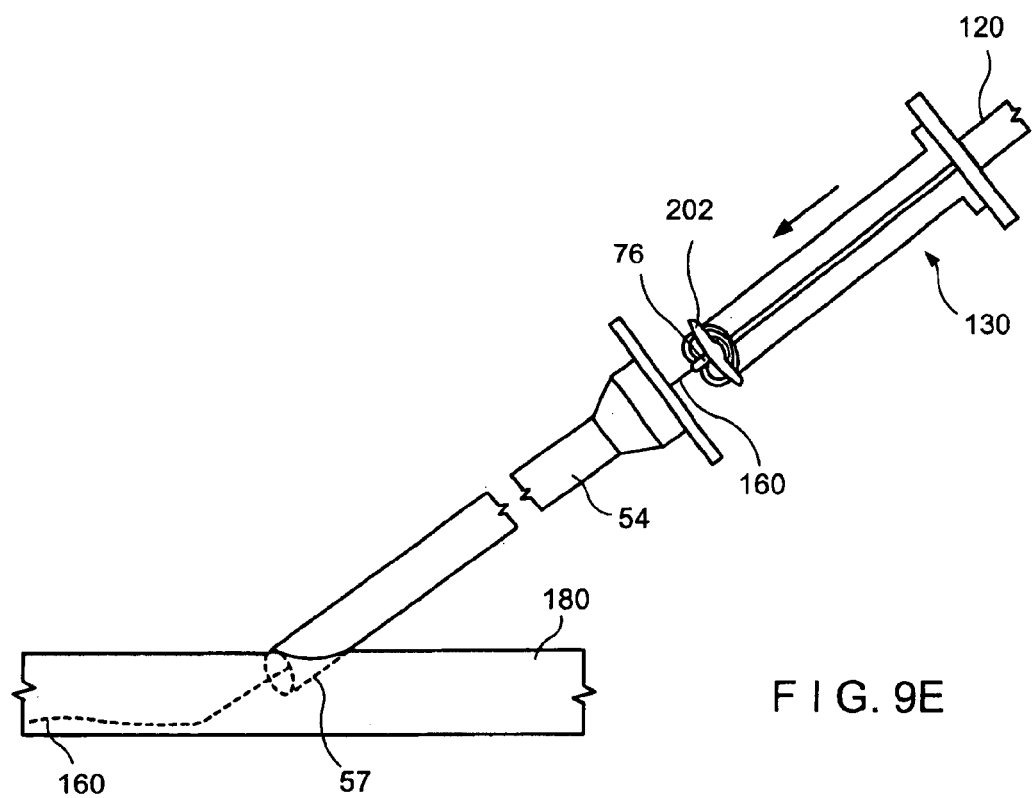

The collectively engaged anastomotic connector delivery and deployment assembly 70 and loading cuff 130 with anastomotic connector 200 operatively loaded therewith, as illustrated in FIG. 9E, are now inserted into the proximal end of sheath 54 over guidewire 160. In this manner, the flange maintains its compressed configuration inside the sheath. Anastomotic connector delivery and deployment assembly 70 is advanced distally such that anastomotic connector device 200 operatively loaded thereon, as described above, is moved out of loading cuff 130. The loaded connector 200 retains its optimally constrained or compressed condition as it is now retained by vessel access sheath 54. Loading cuff 130 may then be removed by pulling on gripping element 136 (herein shown as finger grips) and causing sheath 134 of loading cuff 130 to separate along slit 134 or may be removed by using an appropriate tool such as a cutting tool or the like. In certain embodiments, the loading cuff may remain engaged with the system, but moved out of the way by sliding it a sufficient distance in a proximal direction.

Figure 9F:
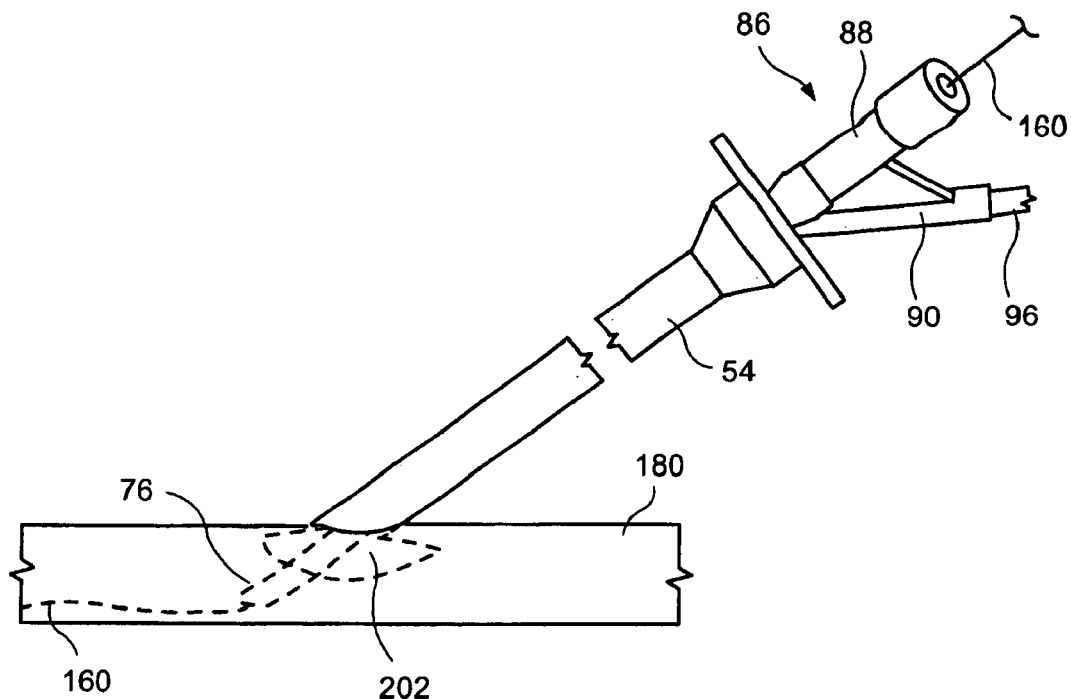

Anastomotic connector delivery and deployment assembly 70 is further advanced distally so as to protrude a distance from the distal tip of sheath 54 in the interior of vessel 180. As shown in FIG. 9F, this secondary advancement places the distal flange member 202 of connector 200 within vessel 180 such that it substantially returns to its original configuration with the vessel. To fully deploy flange member 202 and add to distal stability, inflatable member 76 is inflated by proper adjustment of inflation source 98 as described above with reference to FIG. 7. In an inflated or expanded state, inflatable member 76 expands to deploy distal flange member 202 and apply a stabilizing force to connector 200 to retain it in a substantially fixed position relative to the vessel during the remainder of the deployment procedure and/or may assist in optimally positioning the device. In this manner, the position of distal flange member 202 is maintained upon removal of the components of the system from the body after connector 200 has been fully deployed.

After the distal flange has been deployed, tubular member is deployed. As such, the distal end of sheath 54 is advanced proximally to expose outwardly extending portion 206 of anastomotic connector device 200 retained in slit 124 of tube 120. Inflatable member 76 is further inflated, thereby outwardly flexing the portion of tube 120 about slit 124. Tubular member 204 is deployed out of or away from retaining member 74 such that it assumes an unconstricted or unfolded or uncompressed configuration, i.e., it substantially returns to its original configuration, and is opened or expanded by the action of the inflatable member 76. Retaining member 74 is retracted proximally and additional pressure is applied to inflatable member 76 to inflate further, if required. Accordingly, a graded inflation process, i.e., inflation of the inflatable member in a series of inflation steps, may, although not always, be employed to fully deploy the anastomotic connector, as described above.

Flange deployment and expansion may be accomplished at least partially if not completely by expanding the tubular member, where such tubular member expansion causes the flange to expand to an optimum configuration and position at the target site.

In certain embodiments, multiple inflation/deflation cycles may be employed such that at one or more instances during the delivery and deployment of an anastomotic connector, the inflation members may be deflated and re-inflated one or more times. Such multiple inflation/deflation cycles may be employed during the deployment of the distal flange and/or the expansion of the tubular member. Such multiple inflations may serve, in certain situations, to further stabilize the connector device, seal the flange against the internal wall of the vessel, ensure full expansion of the tubular member, and/or assist in further positioning the connector device if required.

Figure 9G:
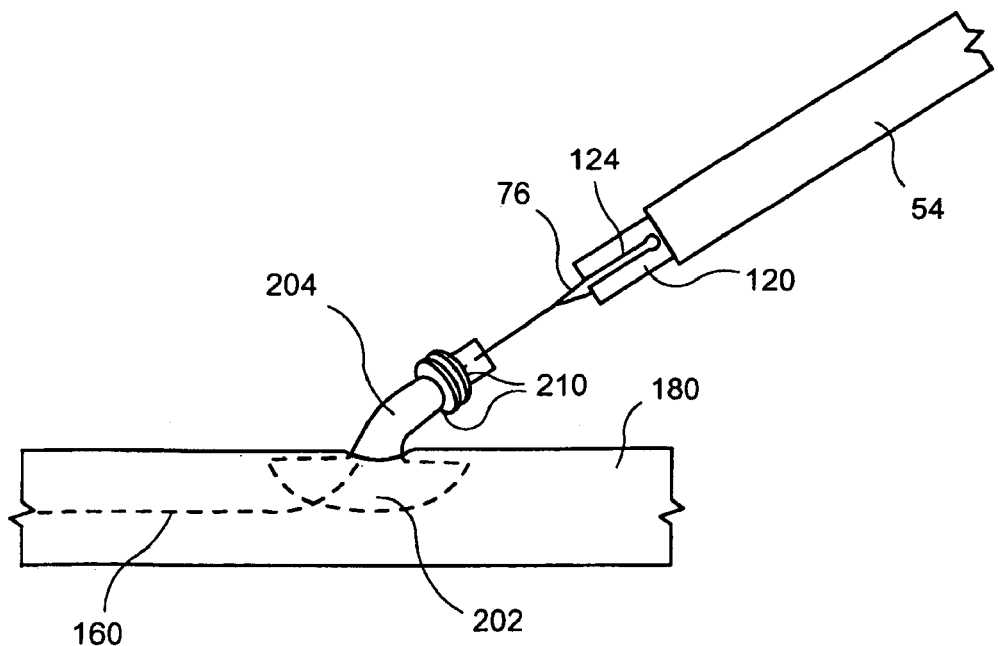

At this point, as shown in FIG. 9G, inflatable member 76 is deflated and the delivery and deployment assembly 70, including engagement member 72 and retaining member 74, and sheath 54 are retrieved over guidewire 160 followed by retrieval of guidewire 160 from within the body. The internal vessel pressure within target vessel 180 causes distal flange 202 to seal against the adjacent vessel wall surface, thereby preventing the escape of fluid, e.g., blood, from the vessel opening.

Finally, as shown in FIG. 9H, a graft vessel 215 is provided and its transected distal end 216 is slid over tubular member 204. After optimally positioning the edges of distal end 216 of the graft vessel 215 with those of target vessel 180 (preferably, the endothelial linings of the vessels are in intimal contact with each other so as to promote natural tissue bonding between them), graft vessel 215 is secured to tubular member 204 by means of parallel securement rings 210 and cooperating outer securement ring 212. Other securement means such as suture loops or the like may be used instead. The proximal end of graft vessel 215 may then be anastomosed to a source of blood, e.g., the aorta, to complete the bypass procedure.

In certain embodiments, graft vessel 215 may be provided on the outside of sheath 54 such that its transected end 216 is slid over sheath 54 (not shown). Accordingly, after the connector device has been partially or completely deployed (i.e., after flange deployment and/or after tubular member deployment) and prior to removal of sheath 54 from the body, the edges of distal end 216 of the graft vessel 215 are optimally positioned with those of target vessel 180 (preferably, the endothelial linings of the vessels are in intimal contact with each other so as to promote natural tissue bonding between them). Inflatable member 76 is deflated and the delivery and deployment assembly 70, including engagement member 72 and retaining member 74, and sheath 54 are retrieved over guidewire 160, followed by retrieval of guidewire 160 from within the body. Graft vessel 215 is secured to tubular member 204 by means of parallel securement rings 210 and cooperating outer securement ring 212, in the manner described above. Other securement means such as suture loops or the like may be used instead. The proximal end of graft vessel 215 may then be anastomosed to a source of blood, e.g., the aorta, to complete the bypass procedure.

Expandable Deployment Member Devices and Systems

As described above, the subject invention also includes anastomotic delivery and deployment devices and systems that employ at least one expandable deployment member for operatively delivering and deploying an anastomotic connector at a target site. Referring now to FIG. 11, there is illustrated an exemplary embodiment of an expandable anastomotic connector delivery and deployment assembly 350 in accordance with the present invention. The expandable anastomotic connector delivery and deployment assembly includes at least one tubular anastomotic connector engagement member that has at least one deployment member configured as an expandable member. In this particular embodiment, assembly 350 includes two engagement members: a first tubular engagement member 360 having a first expandable member 365 and a second tubular engagement member 376 having a second expandable member 382. In further describing the subject expandable deployment member devices, primarily an assembly having two or more expandable members is used for exemplary purposes only and is in no way intended to limit the scope of the invention as assemblies having any number of engagement members and/or expandable deployment members are contemplated by the subject invention, e.g., a single engagement member may be employed, two or three or more engagement members may be employed such as four or more engagement members may be employed and any number of expandable members may be employed.

Figure 11A:
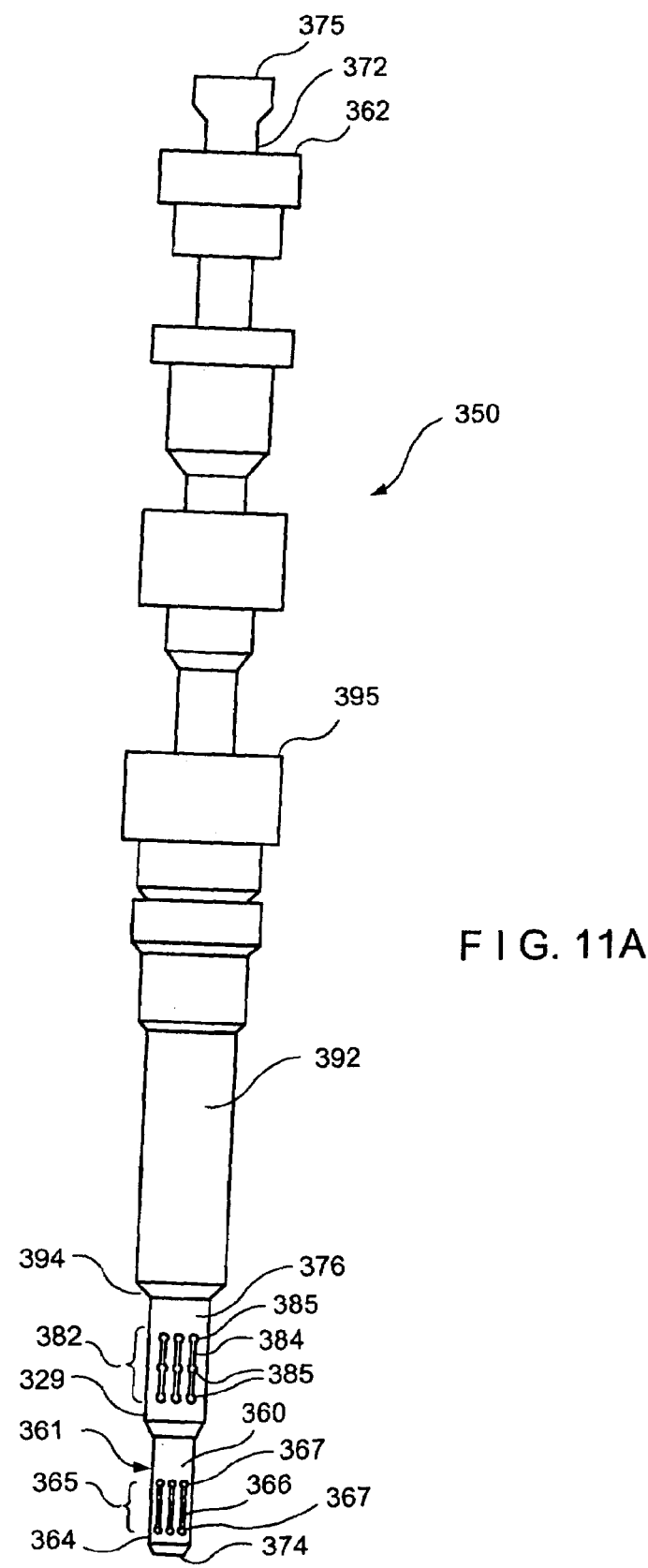
FIG. 11A is a plan view of an exemplary embodiment of an expandable delivery/deployment assembly in accordance with the present invention.
Figure 11B:
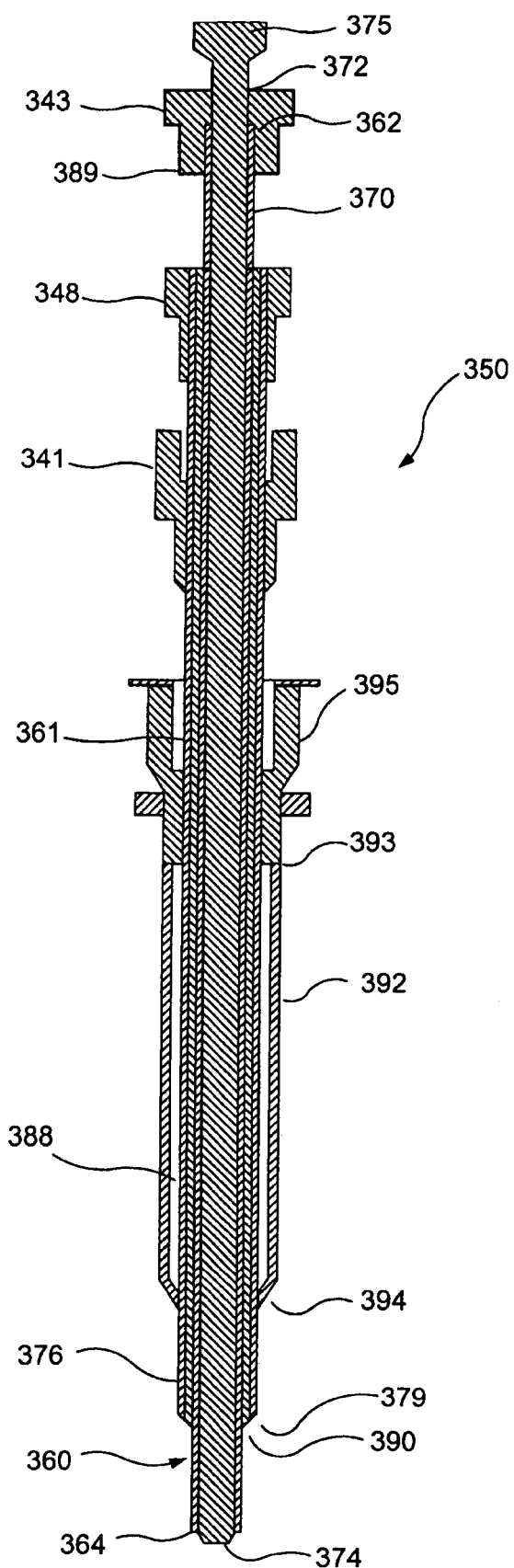
FIG. 11B is a cross-sectional view of the delivery/deployment assembly of FIG. 4.

FIGS. 11A and 11B show an exemplary embodiment of an anastomotic connector delivery and deployment assembly 350 in accordance with the present invention, wherein FIG. 11B is a cross-sectional view illustrating assembly 350 as assembled. Assembly 350 is configured to deliver and deploy an anastomotic connector such as those described above. Assembly 350 includes anastomotic connector engagement member 360 having first expandable member 365 including first actuator 370 slidably disposed therein, second engagement member 376 having second expandable member 382 including a second actuator 388 slidably disposed therein and slidably disposed about first engagement member 360, and tubular retaining member 392 slidably disposed about the second expandable member. Each of the expandable members 365 and 382 and the retaining member 392 further include at least one luer fitting or hemostasis valve assembly disposed at a proximal end or adjacent to a proximal end of each respective element and configured to provide a fluid tight seal therebetween. Assembly 350 also includes one or more sealing elements, shown here as elements 343, 348, 341, 395, such as a silicone seal or the like, for providing a substantially fluid tight seal between the components of the assembly, as will be described below. The elements described above may be disposed coaxially, though this should not be considered limiting in any manner and that it is contemplated that the elements may be disposed in any other manner, for example, side-by-side, or offset.

Anastomotic connector delivery and deployment assembly 350 may be constructed of biocompatible materials such as stainless steel, titanium, polyvinyl chloride, polyurethane, polyamide, polyimide, nylon and other similar materials. For example, the first and second actuators may be formed of polyamide while the first and second expandable members and retaining member may be formed of Hytrel. It shall be understood that the materials described herein are merely exemplary and that it is contemplated that other materials may be utilized. The one or both of the subject deployment members may be covered or coated with a covering such as a fabric and/or elastic material (not shown).

Figures 12A, 12B:
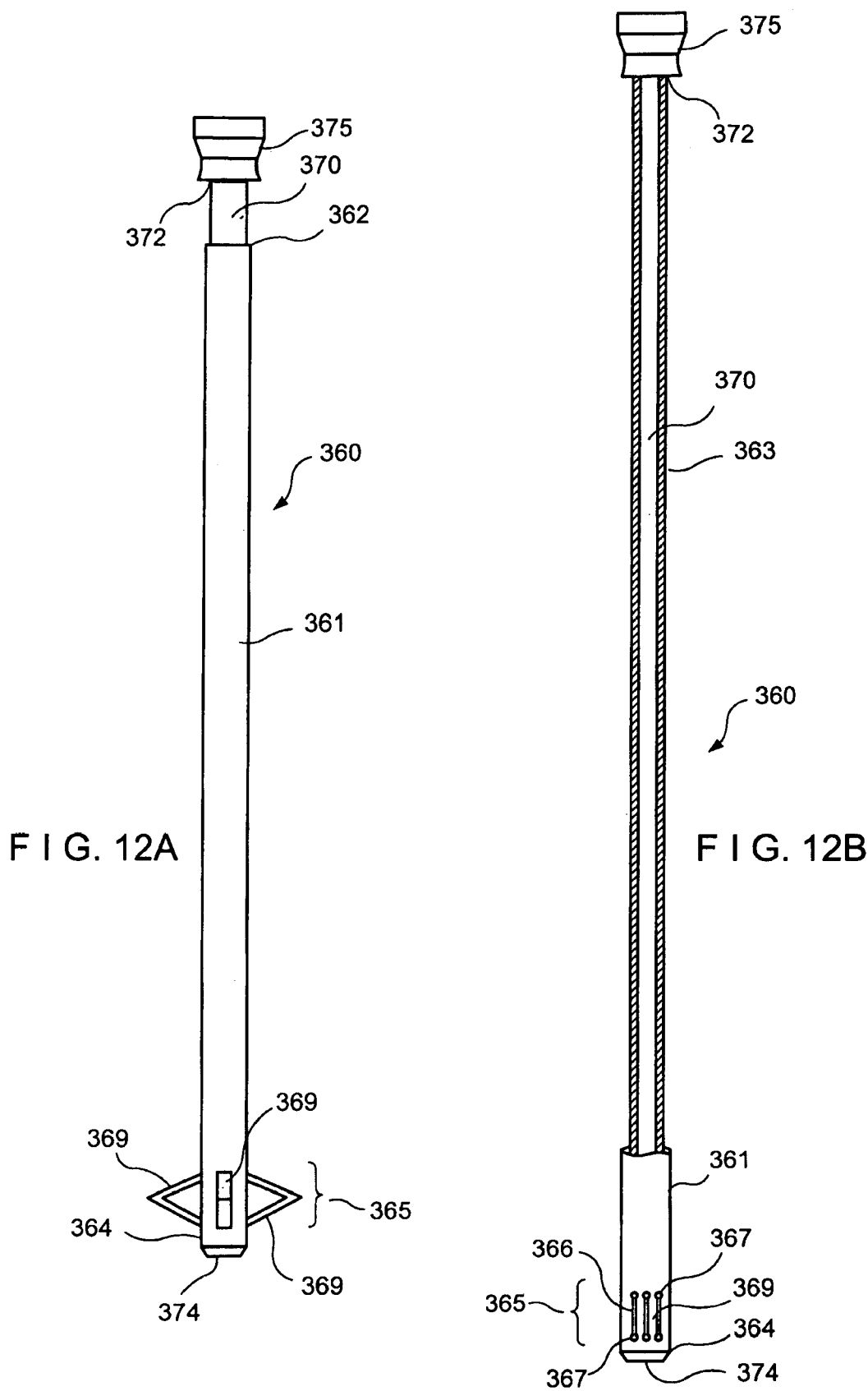
FIG. 12A is a plan view of the first engagement member in accordance with the present invention in an expanded configuration.
FIG. 12B is a partial cross-sectional view of the first engagement member in an unexpanded configuration and illustrates the first actuator.

FIGS. 12A and 12B shows an exemplary embodiment of first engagement member 360 that includes first engagement member 360 and respective actuator 370 in accordance with the present invention. As show in FIGS. 12A and 12B, engagement member 360 includes an elongated generally tubular body 361 defined by a proximal end 362 and a distal end 364 and having a lumen 363 extending therethrough, wherein first actuator 370 is disposed within the lumen of engagement member 360. First engagement member 360 further includes at least one slit 366 formed therein and disposed adjacent to the distal end 364. Slit 366 may further include apertures 367 disposed at either end thereof and anywhere in between, wherein apertures 367 define pivot/flex points of a wall segment 369 of the expandable member, thereby forming expandable member 365. Distal end 374 of actuator 370 is configured to be fixedly attached to distal end 364 of the first engagement member 360. Additionally, distal end 374 of the first actuator 370 includes a tapered/smoothed or rounded surface which forms the distal end of assembly 350. The first actuator 370 may further include a lumen disposed therein, wherein the lumen is configured to slidably receive a guidewire or guide catheter therethrough (not shown). The proximal end 372 of the first actuator further includes a knob 375 or gripping element, wherein the knob 375 allows a user to apply a force to first actuator 370, thereby expanding expandable member 365 as shown in FIG. 12A, in the form of a basket. Expandable member 365 is formed of a plurality of wall segments 369 defined by slits 366 and apertures 367. The shape of expandable member 365 may be controlled by the placement of the apertures 367 and the slits 366. Placing apertures 367 at each end of the slit 366 and within the center portion of the slit 366, bend points are defined.

As shown in FIG. 13, by altering the placement of the apertures 367, the expandable member 365 may be formed to expand having different geometries, for example, as shown, the expandable member 365 may be configured to expand at an angle relative to the elongated shaft of the first engagement member 360. By altering the shape of expandable member 365, the present invention may be designed to provide greater access to inaccessible areas. For example, if the vessel in which the anastomosis device is to be deployed is formed at an angle and a straight expandable portion will not provide sufficient capability, an offset or angled expandable portion may be utilized for placement of the anastomosis device. The function of the expandable portion will be described in greater detail below with regard to the methods of use.

Figure 14:
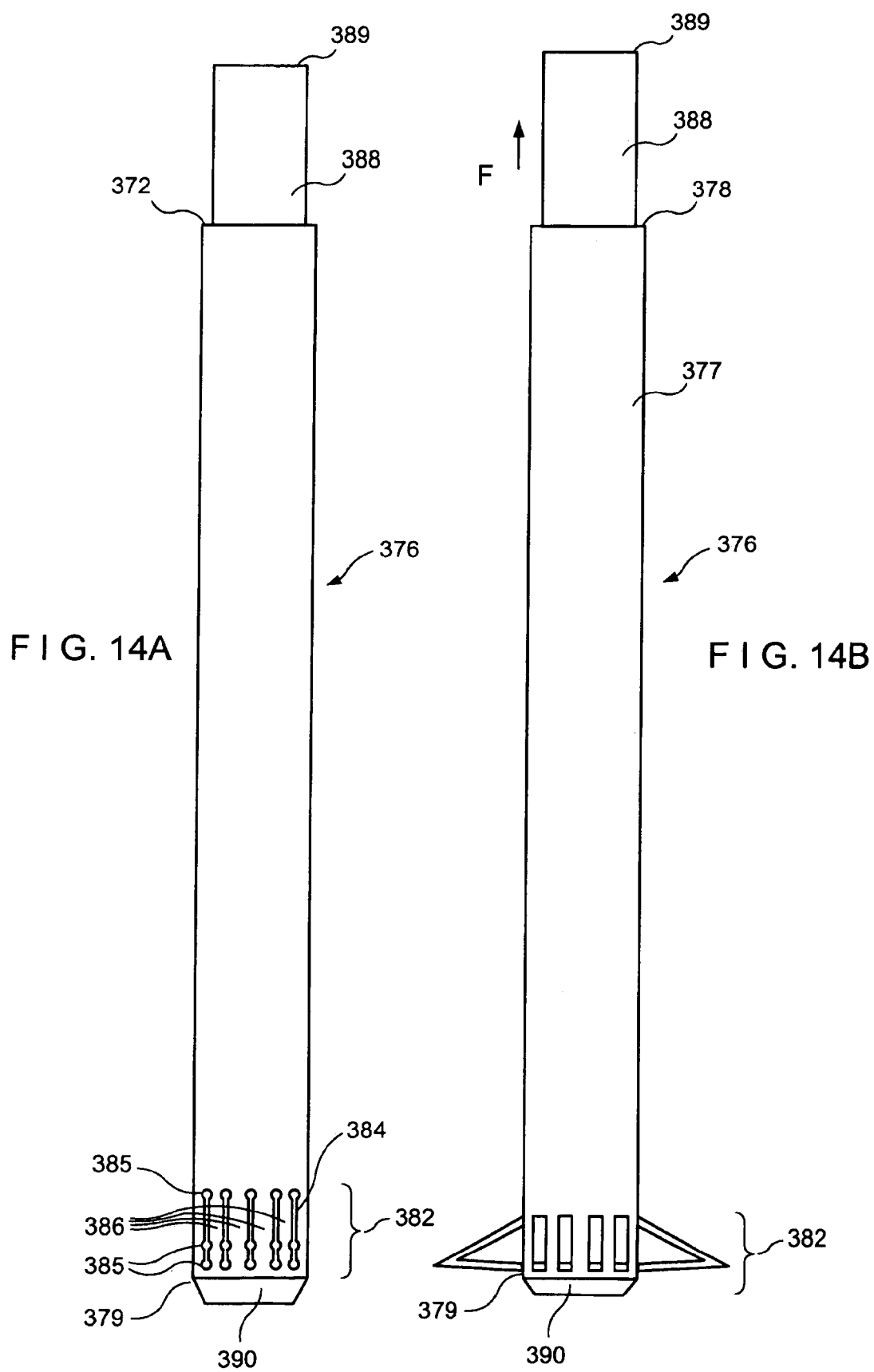
FIG. 14A is a plan view of the second engagement member in accordance with the present invention in an unexpanded configuration.
FIG. 14B is a plan view of the second engagement member in an expanded configuration.

Referring now to FIGS. 14A and 14B, there is shown an exemplary embodiment of second engagement member 376 in accordance with the present invention. As described above, second engagement member 376 is configured to be slideably disposed over first engagement member 360. Second engagement member 376 is defined by proximal end 372 and a distal end 379 and having a lumen extending therethrough. Second engagement member 376 further includes at least one slit 384 disposed within the wall of the second engagement member 376 and disposed adjacent to the distal end 379. A plurality of apertures 385 may be disposed at either end of the slit 384 and anywhere in-between thereby defining a plurality of wall segments 386. Referring to FIG. 14B there is illustrated second engagement member 376, wherein expandable member 382 is shown in an expanded position in the form of a basket. As shown, expandable member 382 is formed of a plurality of wall segments 386 defined by slits 384 and apertures 385. The shape of expandable member 382 maybe controlled by the placement of apertures 385. By placing apertures 385 at each end of slit 384 and at a position adjacent to the distal end of the slit the shape of the expanded member may be controlled. For example, as shown in FIG. 14B, placing apertures 385 adjacent to the distal end of slits 384 shapes the expandable member in the manner shown, wherein the expandable member in an expanded manner forms a laterally extending portion generally perpendicular to the wall of the second engagement member 376.

A second actuator 388 is slidably disposed within the lumen of second engagement member 376, wherein second actuator 388 further includes a lumen extending therethrough (not shown). The lumen of the second actuator 388 is configured to slidably receive the first engagement member 360 and first actuator 70 therein. The distal end 390 of second actuator 388 extends beyond the distal end 379 of the second engagement member 376, wherein distal end 390 of second actuator 388 is configured to provide a smooth surface/transition between the first engagement member 360 and the second engagement member 376. Additionally, distal end 390 of the second actuator 388 is fixedly attached to the distal end 379 of the second engagement member 376. Second engagement member 376 may be deployed by applying a force F to the proximal end 389 of the second actuator 388, wherein the distal end 379 of the second engagement member 376 is pulled on by the distal end 390 of the second actuator, wherein the slits 384 and apertures 385 allow the wall segments 386 of the second expandable member to project radially outward to form expanded portion 382 adjacent to distal end 379 of second engagement member 376. The function of the raised diameter section will be described in greater detail below with regard to the methods of use of the assembly 350 of the present invention.

Figure 15:
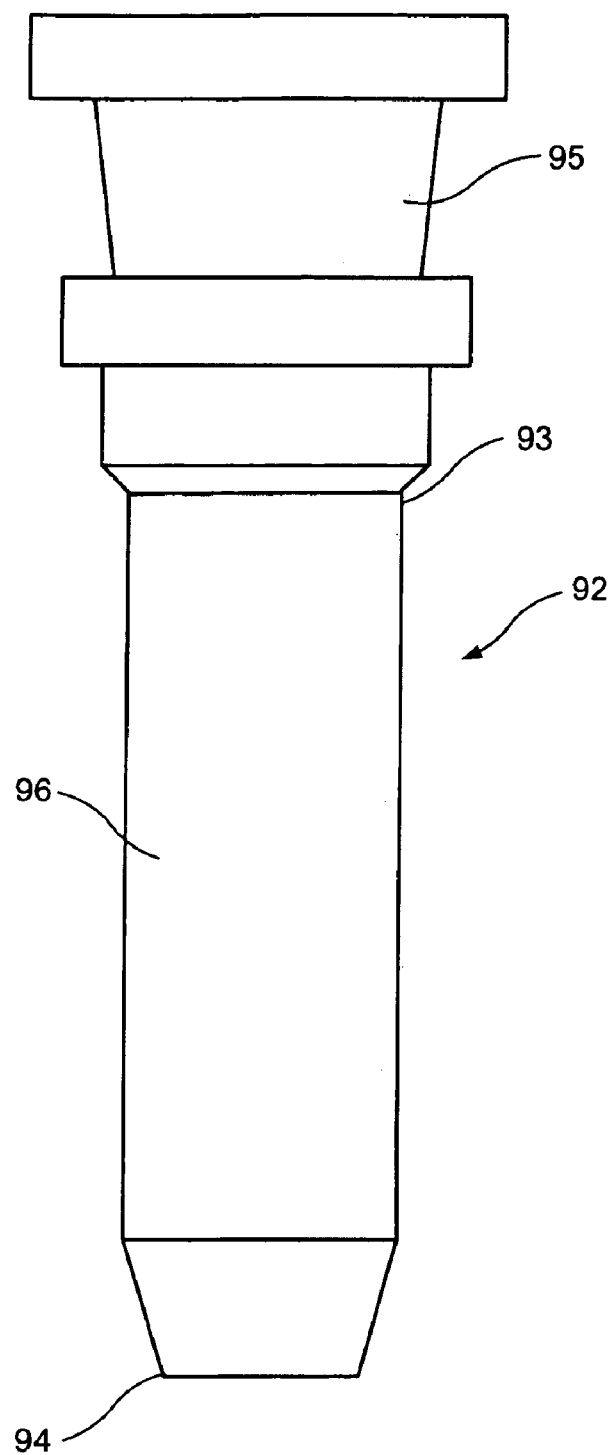
FIG. 15 is a plan view of the retaining member of the assembly of FIG. 11 in accordance with the present invention.

Referring now to FIG. 15, there is shown an exemplary embodiment of a retaining member 392 in accordance with the present invention. Retaining member 392 includes a main body 396 having a distal end 394 and a proximal end 393. Main body 396 further includes a bore (not shown) extending therethrough, wherein the bore is configured to slidably retain second engagement member 376 as shown in FIGS. 11A and 11B. Distal end 394 of retaining member 392 further includes a tapered distal portion, wherein the tapered distal portion is configured to provide a smooth transition between distal end 374 of first actuator 370 and first engagement member 360 to the outer diameter of retaining member 392. Retaining member 392 has a generally cylindrical cross-sectional profile, though other geometric cross-sectional profiles are contemplated. Additionally, retaining member 392 further includes a luer fitting including a sealing means 395 disposed therein. The luer fitting and sealing means 395 are configured to slidably receive the second engagement member 376 and provide a fluid tight seal thereabout.

It shall be understood that the expandable engagement members illustrated and described herein are merely exemplary and should not be considered limiting in any manner. It is contemplated that the subject engagement members may include more than one expandable member, wherein each expandable member may be configured to expand together or individually. Still further, it is contemplated that each expandable member may be configured having different expanded shapes.

Methods of Using the Subject Expandable Member Devices and Systems

As described above, methods of the present invention involve forming an anastomosis between two or more conduits or vessel lumens. Specifically, the subject methods involve connecting a graft vessel to at least one target vessel, where the target vessel is typically located within the body. Suitable applications of the subject anastomotic methods include coronary artery bypass grafting, peripheral artery bypass grafting, the formation of arteriovenous fistulae, and the like. The subject methods employ active deployment of an anastomotic connector to accomplish an anastomotic connection between conduits such as vessel lumens. That is, an anastomotic connector is provided and operatively compressed or constrained from its original configuration, delivered to and positioned at the target site, expanded so that it substantially returns to its original configuration and stabilized using the devices of the subject system.

The graft vessel may be a pedicled vessel requiring only distal attachment to the target vessel or may be a segmented vessel which requires both proximal and distal attachment. The subject devices and methods may be used to perform both proximal and distal anastomosis of the same graft vessel wherein the proximal procedure and the distal procedure may be performed in any order. For example, a segmented graft vessel may be anastomosed proximally to a blood supply vessel, such as the aorta, using either a side-to-side or an end-to-side connector device. The same vessel may then be anastomosed distally to the target vessel using either type of anastomotic connector device as well.

The subject methods may be employed in an open surgical approach in which the physician directly visualizes the surgical field or in a less invasive approach wherein the physician must use an endoscope or the like to visualize the surgical field. Such less invasive methods may be performed through a small incision or port, or intravascularly wherein the subject delivery devices are configured as catheters.

The subject methods for forming a side-to-side anastomosis and an end-to-side anastomosis using the subject expandable deployment delivery devices and systems are now described separately.

Side-to-Side Anastomosis

FIGS. 16A-16G illustrate the steps for delivering and implanting a side-to-side anastomotic connector to join a graft vessel with a target vessel. For purposes of illustrating an example of a side-to-side anastomotic method of the present invention using the subject expandable member devices and systems, primarily the anastomotic connector of FIGS. 2A and 2B and the delivery and deployment assembly 350 of FIGS. 11A and 11B are used; however, such example is not intended to be limiting as any suitable connector configuration and number of expandable members, within the scope of the accompanying claims, may be used to carry out the subject methods.

Figure 16A:
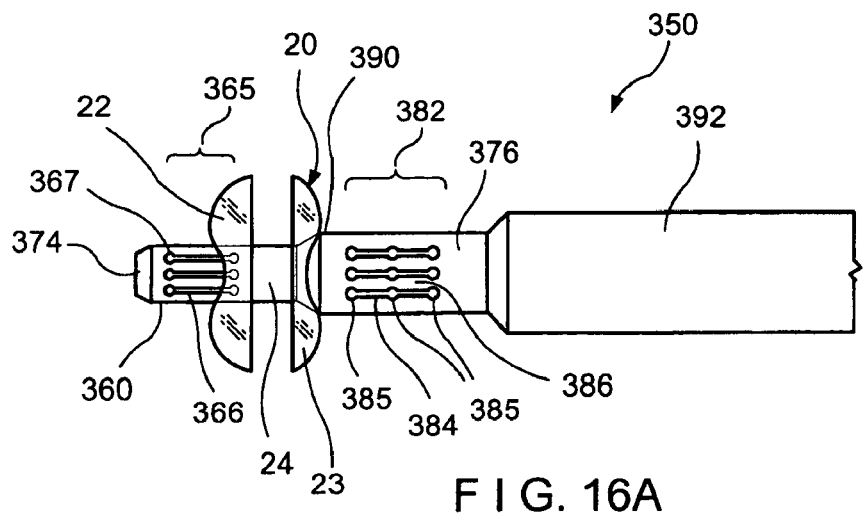

Prior to delivering an anastomotic connector to the target site, the connector must first be properly loaded onto anastomotic connector delivery and deployment assembly 350. As shown in FIG. 16A, anastomotic delivery and deployment assembly 350 is provided having expandable members 365 and 382 shown in an unexpanded or low profile state. An anastomotic connector device 20 having distal flange member 22 and proximal flange member 23 and in an original configuration is slid over unexpanded expandable members 365 and 382, such that expandable members 365 and 382 are positioned through fluid channel 24 of anastomotic connector device 20 such that anastomotic connector 20 is disposed radially about first engagement member 360 up to about distal end 390 of second actuator 388, as shown in FIG. 16A.

Figure 16B:
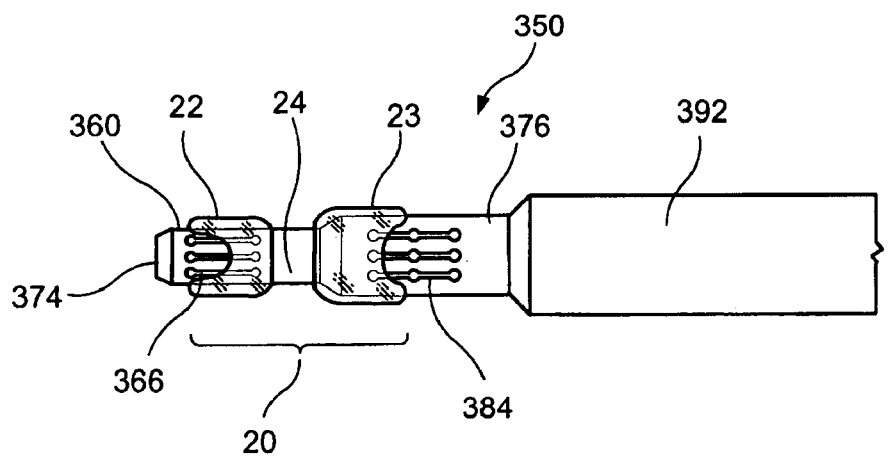

Once operatively positioned about expandable members 365 and 382, first and second flanges 22 and 23, respectively, of anastomotic connector device 20 are then folded or bent about the diameter of first engagement member 360 and second engagement member 376, as shown in FIG. 16B. Flanges 22 and 23 are configured to be folded or bent along the axis of the first and second expandable members, wherein when folded along the axis, the anastomotic device provides a low profile along the axis of the delivery device.

Figure 16C:
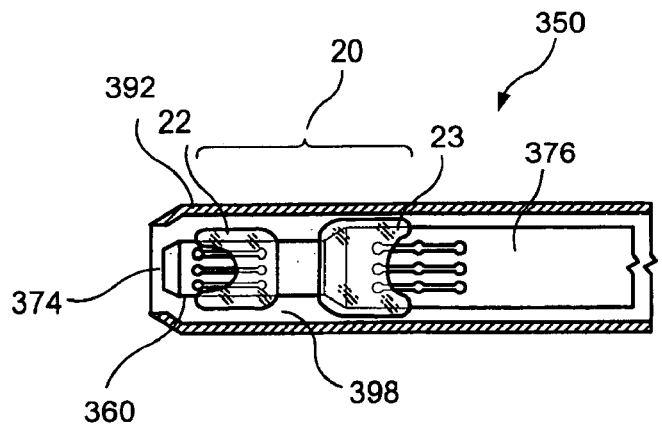

Next, retaining member 392 is translated proximally over anastomotic connector device 20 such that retaining member 392 is disposed about anastomotic device 20, as shown in the cross-sectional view of assembly 350 in FIG. 16C. Retaining member 392 thus provides a continuous coverage surface radially disposed about the diameter of the anastomotic device. Additionally as shown in FIG. 16C, the retaining member forms a cavity 398 adjacent to the distal end of the assembly, wherein anastomotic connector device 20 is configured to be retained within the cavity during delivery to a target site. The dimensions of the cavity enable the cavity to retain flanges 22 and 23 in optimally folded, bent or constrained configurations for delivery and deployment.

Either prior to, during or after the connector loading procedure described above, access is made at the target vessel. Such target vessel access may be accomplished using any convenient protocol, e.g., by a small incision, i.e., an arteriotomy, made in the target vessel or by the Seldinger technique or a modification thereof. With the Seldinger technique, a small gauge needle is introduced through the wall of the target vessel, e.g., a coronary artery, and a guidewire is introduced through the needle and delivered within the target vessel. After proper placement of the guidewire, the needle is withdrawn and the distal end of the guidewire is left in place within the target vessel.

Figure 16D:
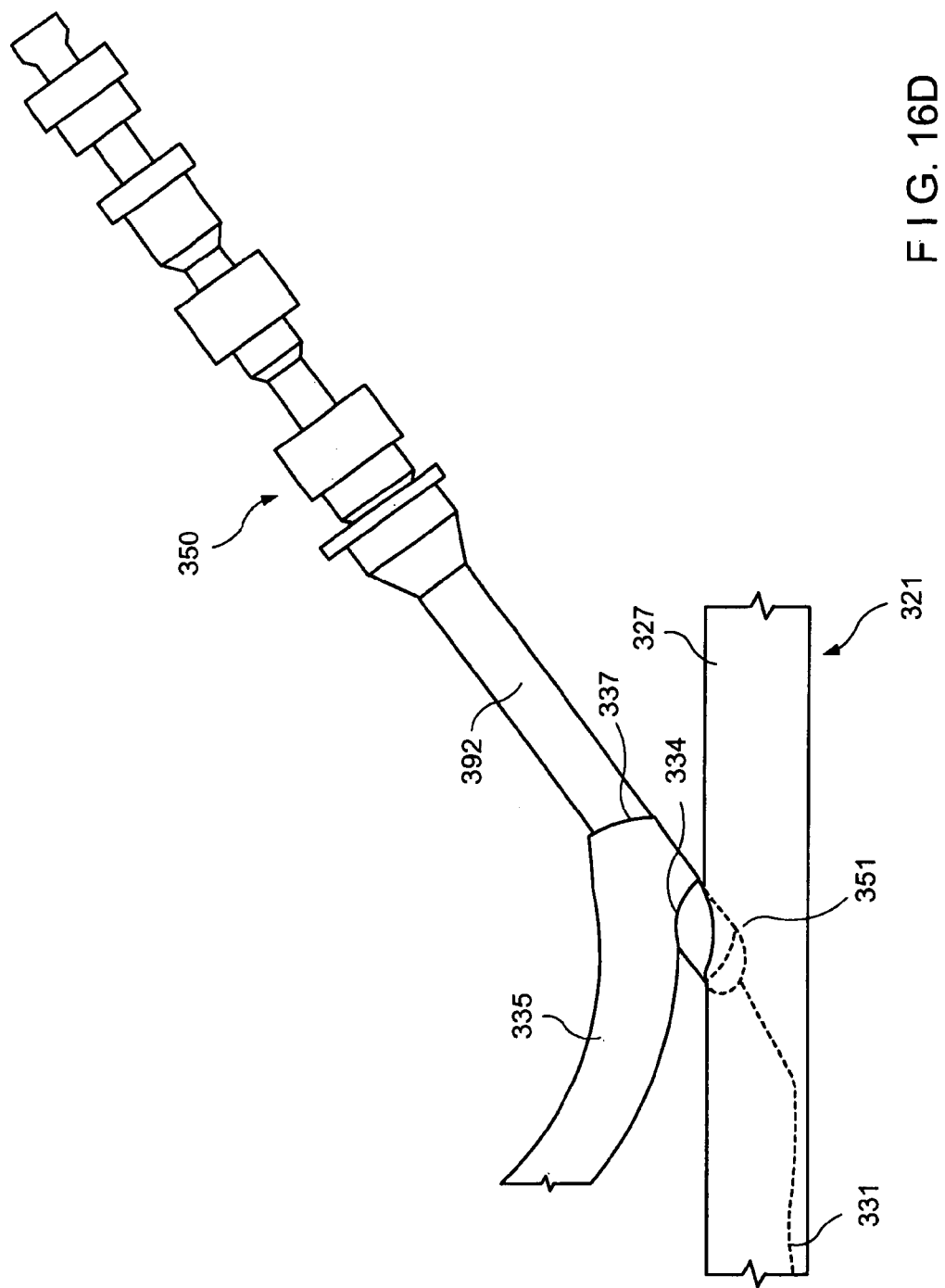

Prior to introducing assembly 350 over guidewire 331, a graft vessel 335 having a transected end 337 is provided. A small opening 339 is made within the side wall of graft vessel 335 close to transected end 337 with enough length such that the vessel may be tied off with suture or surgical clips or the like. As shown in FIG. 16D, the distal end 351 of assembly 350 is inserted through transected end 337 and back out of graft vessel 335 through side opening 339.

Once the access site has been established, a guidewire 331 is operatively positioned at the access site and a graft vessel 335 is disposed onto retaining member 392 of the assembly in the manner described above, assembly 350 is then delivered over guidewire 331 to the target vessel 321. The delivery assembly is advanced a selected distance to dispose distal end 351 of assembly 350 into lumen 327 of target vessel 120. At this point, the lumen of the assembly may be exposed to positive blood pressure within the target vessel. Thus, as shown in FIGS. 11A and 11B, each of the various components of the delivery device 350 includes a sealing means 343, 348, 341, 395, respectively, as described above, wherein the sealing means is configured to provide a fluid tight seal between the blood pressure of the target vessel and the lumens of the delivery device. It shall be understood that the sealing means may include means such as silicone seals or other types of seals that may be configured to provide a fluid tight seal.

At this point, retaining member 392 is retracted a distance proximally, thereby exposing a portion of chamber 398 such that distal flange 22 of anastomotic connector 20 loaded within chamber 398 is allowed to deploy within the target vessel such that distal flange member 22 expands from its constrained, compressed or folded state to its original state to engage the inner wall of target vessel 120, as shown in FIG. 16E, and first expandable member 365 is deployed by moving first actuator 370 proximally. As shown, first expandable member 365 is configured to deploy and stabilize distal flange member 22 of anastomotic device 20 in vessel 321 such that expandable member 365 urges or pushes distal flange member 22 up against the inner wall surface of target vessel 321 such that the expanded expandable member 365 applies a force against flange 22 of the anastomotic device 20 to fully "seat" the flange member against the inner wall of the vessel, wherein blood pressure present within the target vessel retains the flange member against the inner wall of the target vessel. In an expanded state, expandable member 365 applies a stabilizing force to the distal flange and/or the assembly and helps to retain the flange in a substantially fixed position relative to the vessel. In this manner, the position of distal flange member 22 is maintained upon deployment of proximal flange 23 and expansion of fluid channel 24, and removal of components of the system, for example upon proximally translating retaining member 392.

Figure 16F:
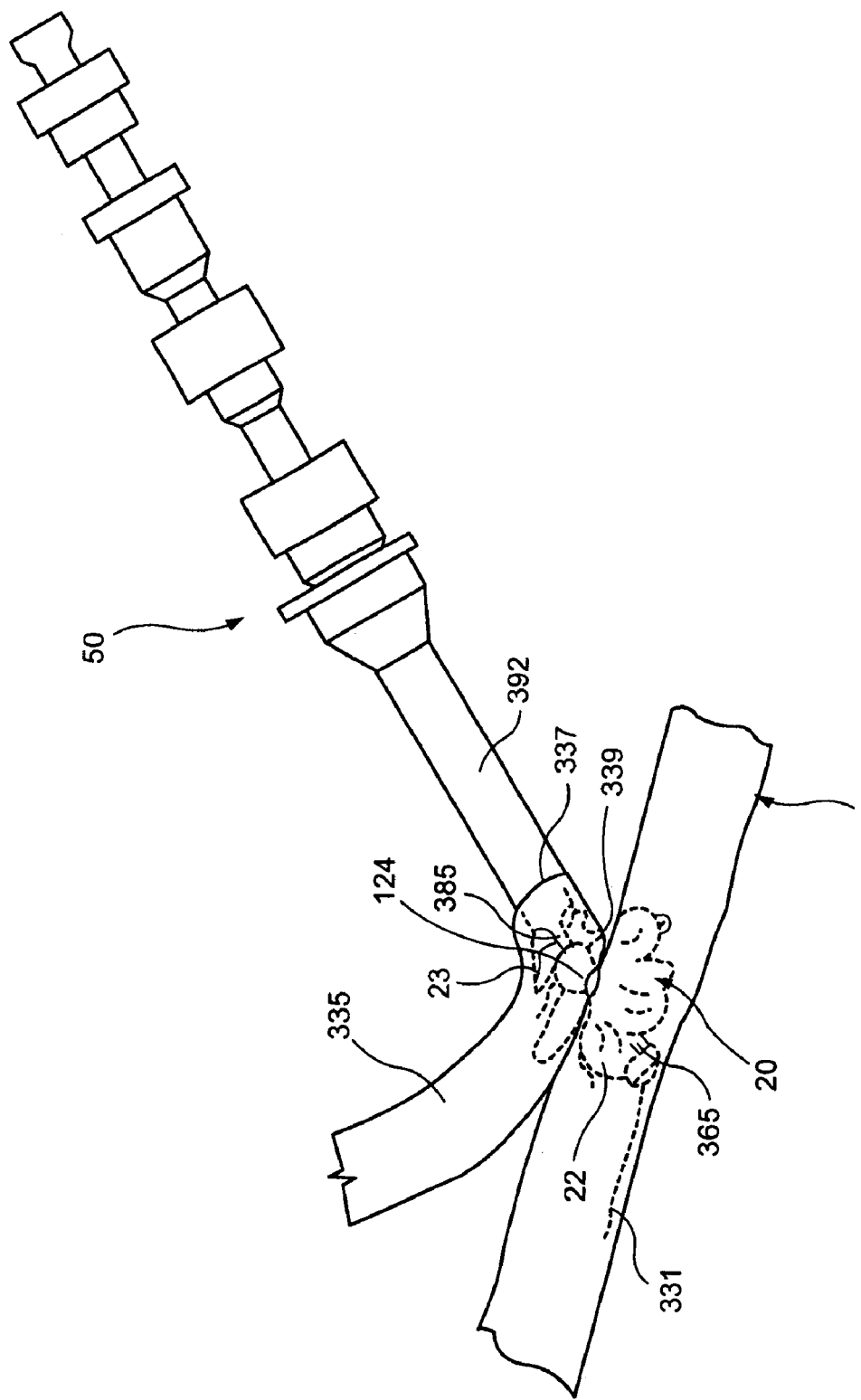

Once distal flange member 22 is engaged with the internal vessel walls of vessel 120 and held in that position by the stabilizing force applied by the expanded expandable member 365, the fluid channel of the connector is opened or expanded and proximal flange 23 is deployed in the following manner. Graft vessel 335 is advanced toward target vessel 321, this may be done by gently sliding the graft vessel along retaining member 392 of assembly 350 and opening 339 of graft vessel 335 is aligned or apposition with opening 324 formed in the target vessel 335. Retaining member 392 of assembly 350 is retracted a greater distance proximally, thereby exposing second or proximal flange member 23 and allowing deployment thereof, as shown in FIG. 16F such that proximal flange member 23 assumes an unbent, unfolded or unconstricted configuration, i.e., assumes its original state.

The deployment of proximal flange member 23 is the same as that described above with regard to the deployment of the first or distal flange member 22, except that proximal flange member 23 expands against the internal wall of graft vessel 335. Accordingly, second expandable member 382 is expanded by advancing the second actuator 388 proximally, wherein the expanded expandable member 382 applies a force against proximal flange 23 of the anastomotic device 20 to fully "seat" the proximal flange member against the inner wall of the graft vessel and stabilize the flange against the inner graft wall. The respective openings 339 and 324 of graft vessel 335 and target vessel 321 are encircled by fluid channel 24 of the anastomotic connector 20 thereby pulling together to maintain contact between their respective edges. Preferably, the endothelial linings of the vessels are in intimal contact with each other so as to promote natural tissue bonding therebetween. The internal vessel pressures cause the respective flanges to seal against the adjacent vessel wall surface, thereby preventing the escape of fluid, e.g. blood, from the vessel opening.

Accordingly, a graded expansion process, i.e., expansion of the expandable members in a series of expansion steps, may, although not always, be employed to deploy the anastomotic connector. That is, the anastomotic connector is deployed by serially expanding the expandable member(s) such that a first expansion deploys the distal flange and, once the distal flange is deployed and stabilized, a second expansion deploys the proximal flange and expands the fluid channel. After this second inflation such that both flanges are deployed and stabilized by the expandable member(s), a third expansion may be employed to fully expand the expandable member(s) if not already fully expanded and fully expand the fluid channel.

Proximal and/or distal flange deployment and expansion may be accomplished at least partially if not completely by expanding the fluid channel, where such fluid channel expansion causes one or both flanges to expand to an optimum configuration and position at the target site.

In certain embodiments, multiple expansion/relaxation (un-expansion) cycles may be employed such that at one or more instances during the delivery and deployment of an anastomotic connector, the expansion members may be relaxed or un-expanded and re-expanded one or more times. Such multiple expansion/relaxation cycles may be employed during the deployment of the distal flange and/or the expansion of the fluid channel and/or the deployment of the proximal flange. Such multiple expansions may serve, in certain situations, to further stabilize the connector device, seal the flange(s) against the internal walls of the vessels, ensure full expansion of the fluid channel, and/or assist in further positioning the connector device if required.

Figure 16G:
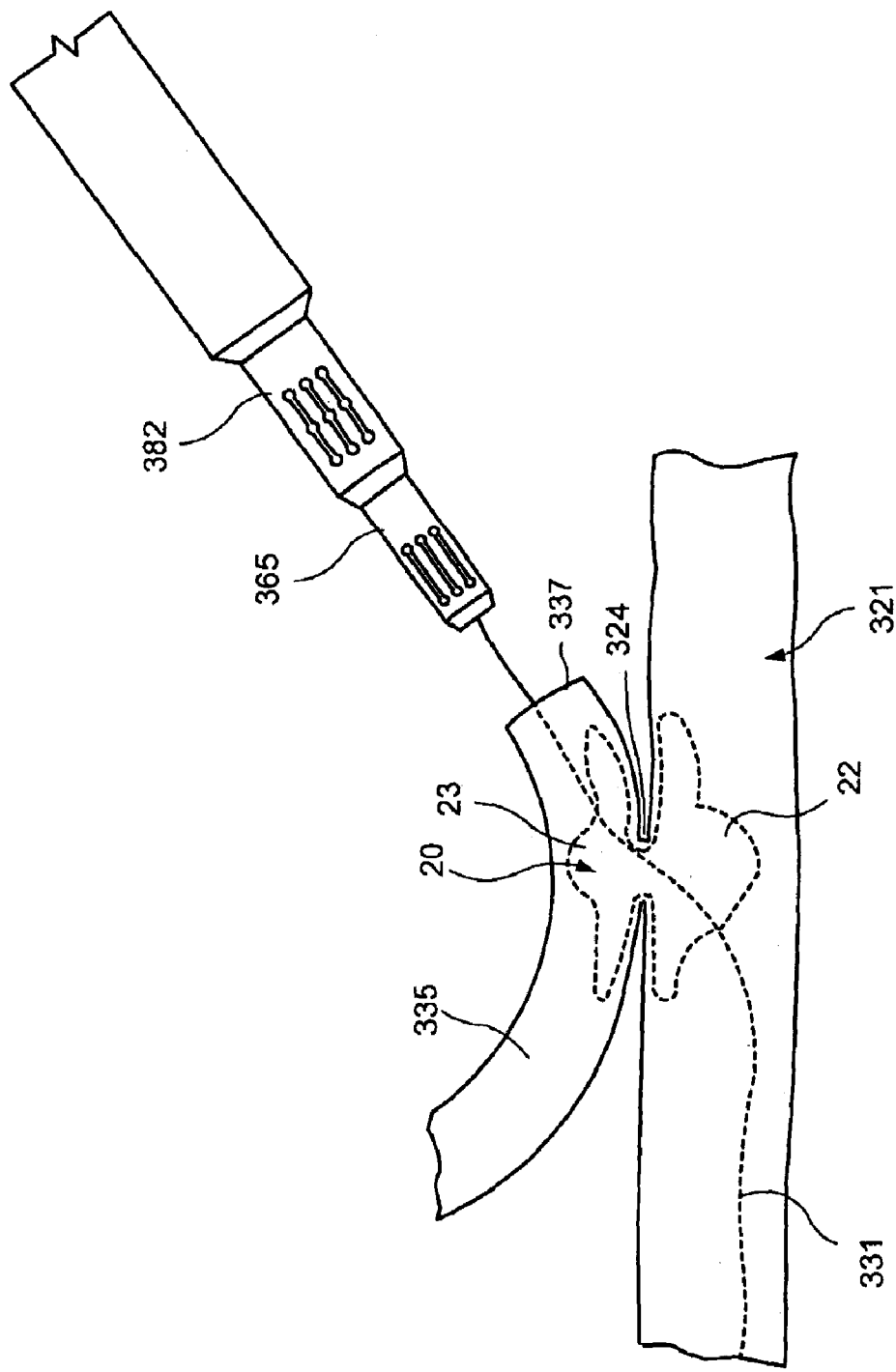

Finally, with respect to FIG. 16G, there is shown the completed side-to-side anastomosis. To remove the assembly from the body, each of the expandable members 365 and 382 of assembly 350 is collapsed from its expanded state and assembly 350 is retracted proximally over guidewire 331 and removed from within target vessel 321 and graft vessel 335 and ultimately from the body. The transected end of the graft vessel is then closed, this may be accomplished by tying off with a suture or closing it with other means such as clips, glues or similar devices.

Figure 17:
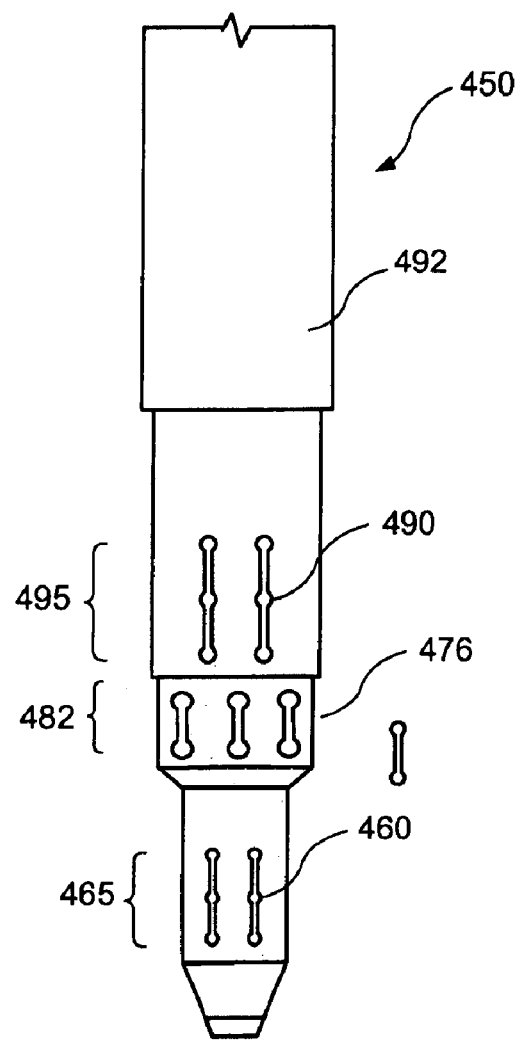
FIG. 17 is an exemplary embodiment of a subject engagement member having three expandable deployment members.

As mentioned above, the subject devices may include more than one or expandable members. FIG. 17, shows an exemplary alternative embodiment of the anastomotic connector delivery and deployment assembly in accordance with the present invention. As shown in FIG. 17, assembly 450 includes an outer retaining member 492, first engagement member 460 that include first expandable member 465, second engagement member 476 that includes second expandable member 482 and third engagement member 490 that include third expandable member 495. In many embodiments, each expandable member is coupled, respectively, to an actuating member; however in certain embodiments one or more expandable members may be coupled to the same actuator. As shown in FIG. 17, each expandable member is disposed adjacent to one another. Additionally, each expandable member may be independently actuated by applying force to each respective actuating member.

Figure 18A:
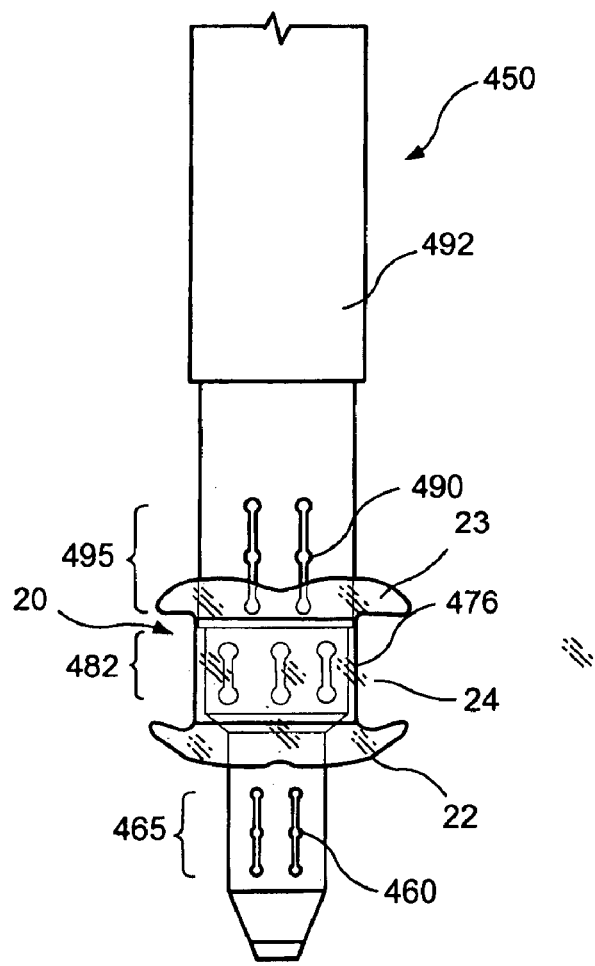
FIGS. 18A-18C illustrate various steps of a method of the present invention of forming a side-to-side anastomotic connection using the device of FIG. 17.
Figure 18B:
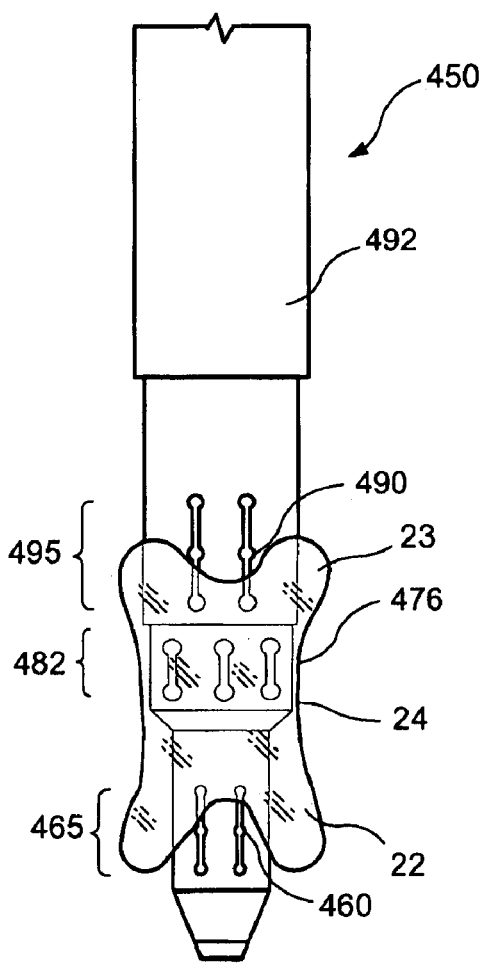
Figure 18C:
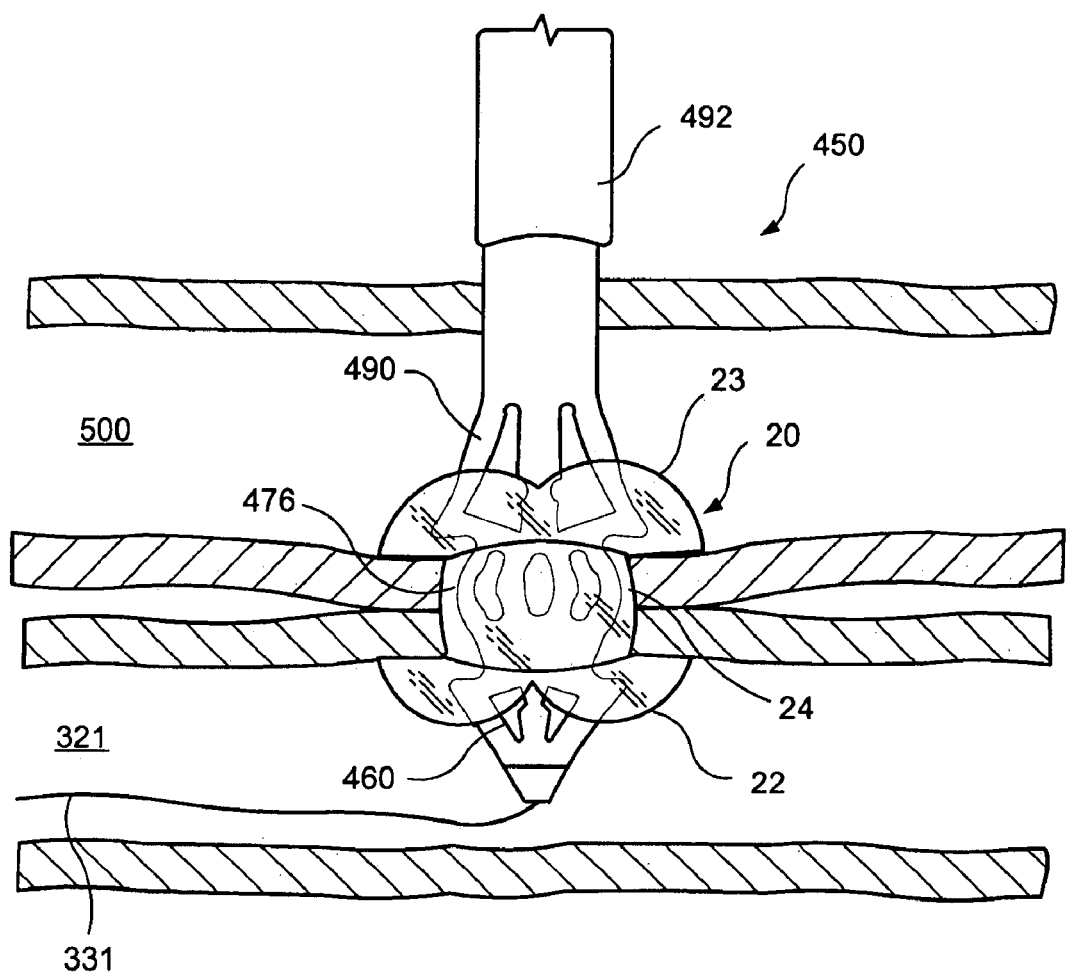

FIGS. 18A through 18C illustrate the steps for delivering and implanting a side-to-side anastomotic connector to join a graft vessel with a target vessel using assembly 450. Accordingly, to use assembly 450, anastomotic connector 20 is operatively loaded on assembly 450 in a manner analogous to that described above with respect to assembly 350. That is, prior to delivering an anastomotic connector to the target site using assembly 450, anastomotic delivery and deployment assembly 450 is provided that includes expandable members 465, 482 and 495, shown in an unexpanded or low profile state in FIG. 18A. Anastomotic connector device 20 having distal flange member 22 and proximal flange member 23 and fluid channel 24 is slid over unexpanded expandable members 465, 482 and 495, such that the expandable members are positioned through fluid channel 24 of anastomotic connector device 20, as shown in FIG. 18A, such that first expandable member 465 is disposed adjacent to a first or distal flange 12 of anastomotic connector 20, the second expandable member 482 is disposed adjacent to flow channel 24 of anastomosis connector 20, and the third expandable member 495 is disposed adjacent a second or proximal flange 23.

Once operatively positioned about expandable members 465, 482 and 495, first and second flanges 22 and 23, respectively, of anastomotic connector device 20 are then folded or bent about the diameter of first engagement member 460, second engagement member 476 and third engagement member 490, as shown in FIG. 18B. Flanges 22 and 23 are configured to be folded or bent along the axis of the expandable members, wherein when folded along the axis, the anastomotic device provides a low profile along the axis of the delivery device. Retaining member 492 is then translated distally over folded connector device 20 and anastomotic connector device is delivered and deployed in a manner analogous to that described above and which need not be fully reiterated herein, but will be briefly described below.

The assembly 450 with the loaded anastomotic connector 20 is inserted into a patient's vasculature to deploy anastomotic device 20. The distal end of the delivery device 450 is inserted into a target vessel 321 over a guidewire 331, and the first expandable member 465 is deployed by proximally retracting sheath 492 a distance to expose flange 22 and expanding first expandable member 465. At the same time or following the deployment of distal flange 22, fluid opening 24 is exposed and expanded by proximally retracting sheath 492 a distance and expanding second expandable member 482, disposed within flow channel 24, thereby ensuring proper fluid flow between the vessels. Finally, proximal flange 23 is deployed by further proximally retracting sheath 492 to expose flange 23 and expanding third expandable member 496. The assembly is then returned to its unexpanded or low profile state and removed from the body, as described above. In such a manner, the anastomotic connector is fully deployed to join the target vessel and graft vessel together such that the proximal and distal flanges are engaged in a sealing relationship with the internal vessel walls where they are held against the internal vessel walls by the blood pressure in the vessels and the flow channel 24 disposed between the first and second flanges is deployed and expanded in a generally cylindrical manner and without any restrictions to ensure patency of the anastomosis.

Accordingly, a graded expansion process, i.e., expansion of the expandable members in a series of expansion steps, may, although not always, be employed to deploy the anastomotic connector. That is, the anastomotic connector is deployed by serially expanding the expandable member(s) such that a first expansion deploys the distal flange and, once the distal flange is deployed and stabilized, a second expansion expands the fluid channel. A third expansion then deploys the proximal flange. After this third inflation such that both flanges are deployed and stabilized by the expandable member(s), a fourth expansion may be employed to fully expand the expandable member(s) if not already fully expanded and fully expand the fluid channel.

Proximal and/or distal flange deployment and expansion may be accomplished at least partially if not completely by expanding the fluid channel, where such fluid channel expansion causes one or both flanges to expand to an optimum configuration and position at the target site.

In certain embodiments, multiple expansion/relaxation (un-expansion) cycles may be employed such that at one or more instances during the delivery and deployment of an anastomotic connector, the expansion members may be relaxed or un-expanded and re-expanded one or more times. Such multiple expansion/relaxation cycles may be employed during the deployment of the distal flange and/or the expansion of the fluid channel and/or the deployment of the proximal flange. Such multiple expansions may serve, in certain situations, to further stabilize the connector device, seal the flange(s) against the internal walls of the vessels, ensure full expansion of the fluid channel, and/or assist in further positioning the connector device if required.

FIG. 18C shows assembly 450 fully expanded and connector 20 deployed, thereby joining the graft vessel 500 and target vessel 321 together with the fluid channel of the connector therebetween.

End-to-Side Anastomosis

FIGS. 19A-19G illustrate the steps for delivering and implanting an end-to-side anastomotic connector to join a graft vessel with a target vessel using the subject expandable deployment devices and systems. Reference numerals that are identical to those used in connection with FIGS. 16A-16G, 17 and 18C represent the same or analogous elements or features in FIGS. 19A-19H. For purposes or illustrating an example of an end-to-side anastomotic method of the present invention, primarily the anastomotic connector of FIG. 3 and the assembly of FIGS. 11A and 11B are used having a single expandable member; however, such example is not intended to be limiting as any suitable connector and configuration and number of expandable member(s), within the scope of the accompanying claims, may be used to carry out the subject methods.

Figure 19A:
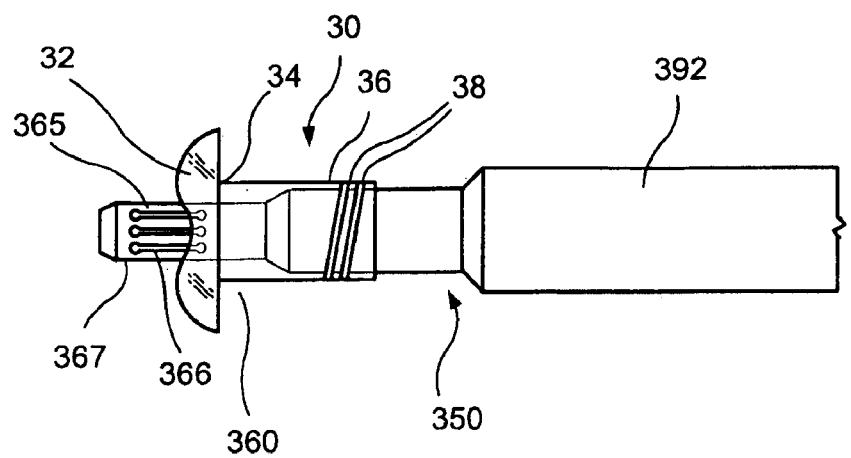
FIGS. 19A-19G illustrate various steps of a method of the present invention of forming an end-to-side anastomotic connection using the subject expandable deployment member devices and systems.

Prior to delivering an anastomotic connector to the target site, the connector must first be properly loaded onto engagement member 360 of assembly 350. As shown in FIG. 19A, delivery and deployment assembly 350 is provided and has a single anastomotic connector engagement member 360 having expandable deployment member 365, shown in an unexpanded or low profile state. Anastomotic connector device 30 having distal flange member 32 and tubular member 36 in an original state is slid over unexpanded engagement member 360 which is positioned through tubular member 36.

Figure 19B:
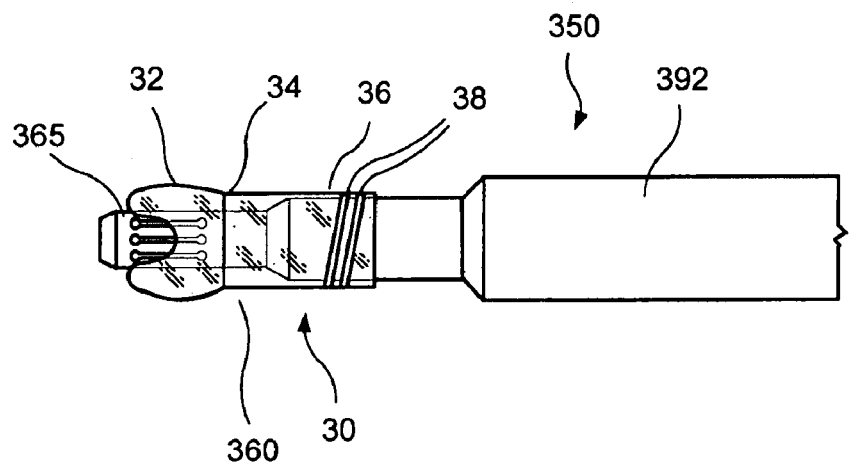

Once operatively positioned about expandable member 365, flange 32 of anastomotic connector device 30 is then folded or bent about the diameter of engagement member 360, as shown in FIG. 19B. Flange 32 is configured to be folded or bent along the axis of the expandable member, wherein when folded along the axis, the anastomotic device provides a low profile along the axis of the delivery device.

Figure 19C:
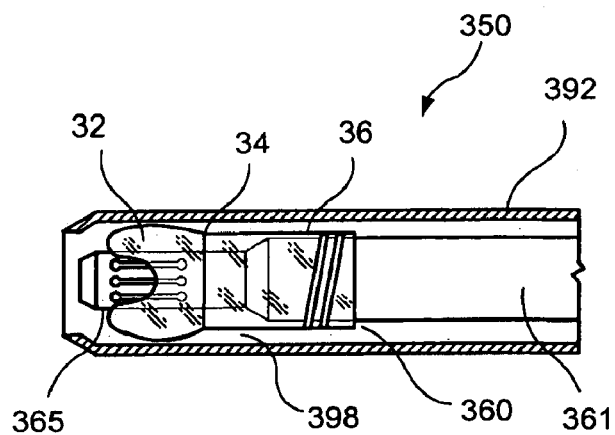

Next, retaining member 392 is translated proximally over anastomotic connector device 20 such that retaining member 392 is disposed about anastomotic device 30, as shown in the cross-sectional view of assembly 350 in FIG. 19C. Retaining member 392 thus provides a continuous coverage surface radially disposed about the diameter of the anastomotic device. Additionally as shown in FIG. 19C, the sheath forms a cavity 398 adjacent to the distal end of the assembly wherein anastomotic connector device 20 is configured to be retained within the cavity during delivery to a target site. The dimensions of the cavity are such that the cavity retains flange 32 in an optimally folded, bent or constrained configuration for delivery and deployment.

Either prior to, during or after the connector loading procedure just described, access is made at the target vessel. As discussed above with respect to the method of forming a side-to-side anastomosis connection, such may be accomplished using any convenient protocol, e.g., by a small incision, i.e., an arteriotomy, made in the target vessel or by the Seldinger technique or a modification thereof.

Figure 19D:
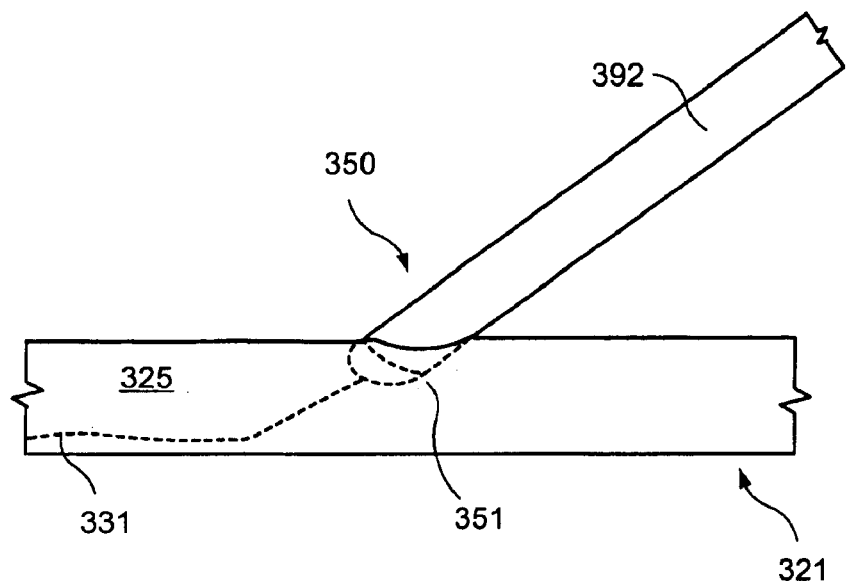

Once the access site has been established and a guidewire 331 is operatively positioned at the access site, assembly 350 having anastomotic connector 30 operatively loaded thereon is then delivered over guidewire 331 to the access site within target vessel 321. The delivery assembly is advanced distally a selected distance to dispose distal end 351 of assembly 350 into lumen 325 of target vessel 321, as shown in FIG. 19D.

Figure 19E:
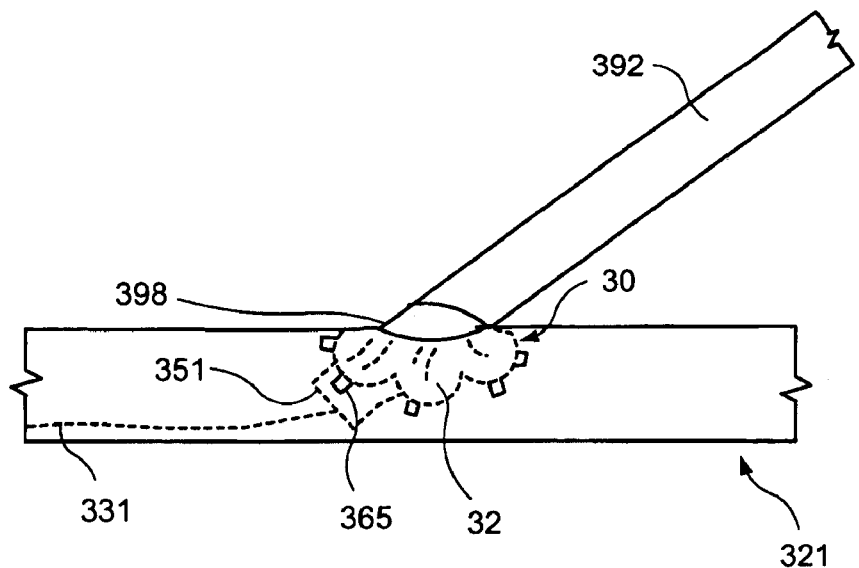
Figure 19F:
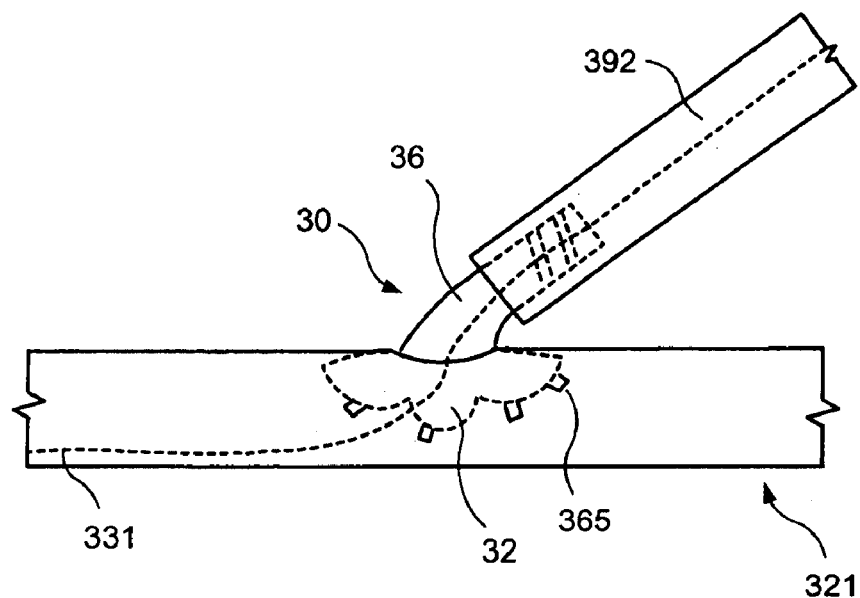

Next, retaining member 392 is retracted a distance proximally, thereby exposing a portion of chamber 398 such that flange 32 of anastomotic connector 30 loaded within chamber 398 is allowed to deploy within the target vessel such that flange member 32 expands from its constrained, compressed or folded condition to engage the inner wall of target vessel 321. As shown in FIG. 19E, expandable member 365 is deployed by moving the actuator of expandable member 365 proximally, thereby expanding expandable member 365. As shown, expandable member 365 is configured to deploy flange member 32 of anastomotic device 30 in vessel 321 such that expandable member 365 urges or pushes distal flange member 32 up against the inner wall surface of target vessel 321, such that the expanded expandable member 365 applies a force against flange 32 of the anastomotic device 30 to fully "seat" the flange member against the inner wall of the vessel, wherein blood pressure present within the target vessel retains the flange member against the inner wall of the target vessel. In an expanded state, expandable member 365 applies a stabilizing force to connector 30 and helps to retain connector 30 in a substantially fixed position relative to the vessel. In this manner, the position of flange 32 is maintained upon deployment and expansion of tubular member 36, and removal of components of the system, for example upon proximally retracting retaining member 392.

After flange 32 has been deployed, tubular member 36 is deployed. As such, the distal end of retaining member 392 is advanced proximally to expose and expand tubular member 32. It will be apparent that a second expansion member may be employed to assist in the expansion of the tubular member. Accordingly, a graded inflation process, i.e., expansion of the expandable member(s) in a series of expansion steps, may, although not always, be employed to fully deploy the anastomotic connector, as described above.

Flange deployment and expansion may be accomplished at least partially if not completely by expanding the tubular member, where such tubular member expansion causes the flange to expand to an optimum configuration and position at the target site.

In certain embodiments, multiple expansion/relaxation (un-expansion) cycles may be employed such that at one or more instances during the delivery and deployment of an anastomotic connector, the expansion member(s) may be un-expanded and re-expanded one or more times. Such multiple expansion/unexpansion cycles may be employed during the deployment of the distal flange and/or the expansion of the tubular member. Such multiple expansions may serve, in certain situations, to further stabilize the connector device, seal the flange against the internal wall of the vessel, ensure full expansion of the tubular member, and/or assist in further positioning the connector device if required.

Figure 19G:
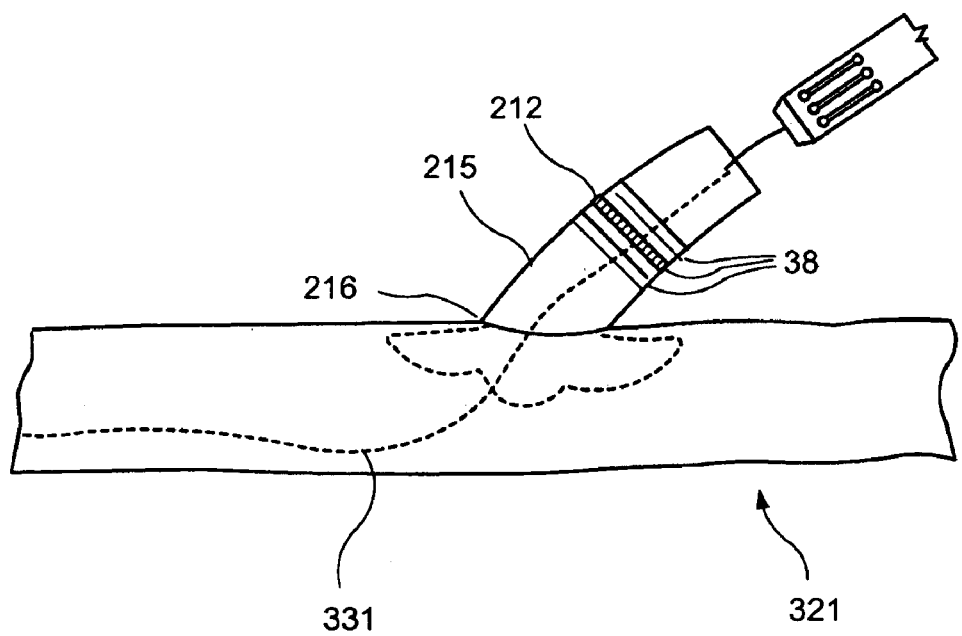

At this point, as shown in FIG. 19G, engagement member 360 is caused to collapse into an unexpanded state and assembly 350 is retrieved over guidewire 321 followed by retrieval of guidewire 331 from within the body. The internal vessel pressure within target vessel 321 causes flange 32 to seal against the adjacent vessel wall surface, thereby preventing the escape of fluid, e.g., blood, from the vessel opening.

Finally, as shown in FIG. 19G, a graft vessel 215 is provided and its transected distal end 216 is slid over tubular member 204. After optimally positioning the edges of distal end 216 of the graft vessel 215 with those of target vessel 321 (preferably, the endothelial linings of the vessels are in intimal contact with each other so as to promote natural tissue bonding between them), graft vessel 215 is secured to tubular member 36 by means of parallel securement rings 38 and cooperating outer securement ring 212. Other securement means such as suture loops or the like may be used instead. The proximal end of graft vessel 215 may then be anastomosed to a source of blood, e.g., the aorta, to complete the bypass procedure.

In certain embodiments, graft vessel 215 may be provided on the outside of retaining member 392 such that its transected end 216 is slid over retaining member 392 (not shown). Accordingly, after the connector device has been deployed and prior to removal of assembly 350 from the body, the edges of distal end 216 of the graft vessel 215 are optimally positioned with those of target vessel 321 (preferably, the endothelial linings of the vessels are in intimal contact with each other so as to promote natural tissue bonding between them). Expandable member 365 is relaxed or unexpanded and the delivery and deployment assembly 350 is retrieved over guidewire 331, followed by retrieval of guidewire 331 from within the body. Graft vessel 215 is secured to tubular member 36 by means of parallel securement rings 210 and cooperating outer securement ring 212, in the manner described above. Other securement means such as suture loops or the like may be used instead. The proximal end of graft vessel 215 may then be anastomosed to a source of blood, e.g., the aorta, to complete the bypass procedure.

Devices and Systems Having at Least One Expandable Deployment Member and at Least One Inflatable Deployment Member As described above, the subject invention also includes anastomotic connector delivery and deployment devices and systems that include at least one inflatable deployment member and at least one expandable deployment member, where a variety of such configurations may be employed.

In using the subject devices and systems having at least one inflatable deployment member and at least one expandable deployment member, the deployment members function as described above. For example, in regards to an end-to-side anastomosis, a distal deployment member, whether inflatable or expandable, may serve to deploy a distal flange and stabilize the device and a proximal deployment member, whether inflatable or expandable, may serve to deploy a proximal flange, stabilize the device and expand a fluid channel. In those embodiments having a middle deployment member, such may serve to expand a fluid channel and stabilize the device. For example in regards to an end-to-side anastomosis, a distal deployment member, whether inflatable or expandable, may serve to deploy a distal flange and stabilize the device and a proximal deployment member, whether inflatable or expandable, may serve to expand the tubular member and stabilize the device.

Figure 20A:
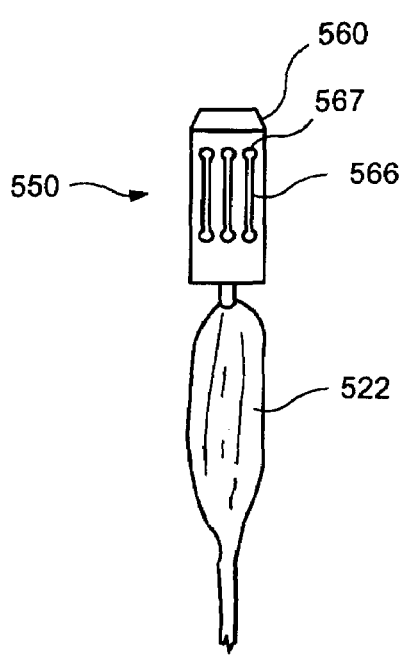
FIG. 20A shows an exemplary embodiment of a subject anastomotic connector delivery and deployment assembly having an inflatable deployment member and an expandable deployment member.
Figure 20B:
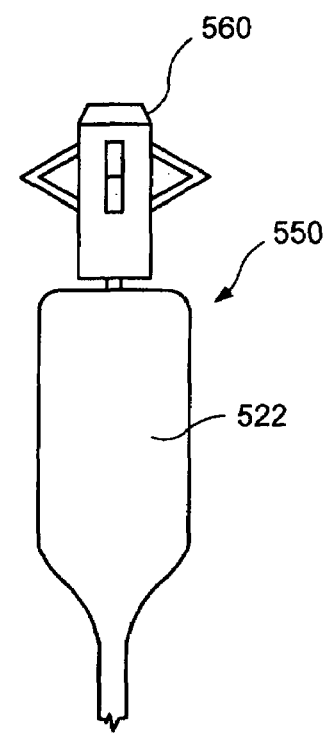
FIG. 20B shows the anastomotic connector delivery and deployment assembly of FIG. 20A in an expanded configuration.

Accordingly, FIGS. 20A and 20B show an exemplary embodiment of an anastomotic connector delivery and deployment assembly 550 having a proximal deployment member 522 configured as an inflatable deployment member and a distal deployment member 560 configured as an expandable deployment member, where the order may be reversed. As shown, deployment members 522 and 560 are arranged serially with respect to each other. Specifically, FIG. 20A shows inflatable member 522 in a deflated state and expandable member 560, having slits 566 and apertures 567, in an unexpanded or low profile state. FIG. 20B shows inflatable member 522 inflated and expandable member 560 expanded.

Figure 21A:
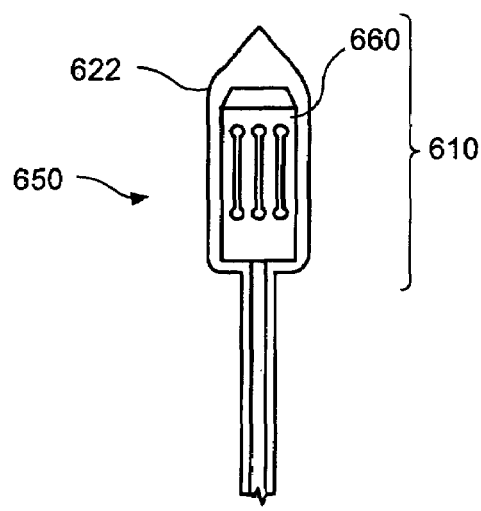
FIG. 21A shows an exemplary embodiment of a subject anastomotic connector delivery and deployment assembly having an expandable deployment member disposed within an inflatable deployment member.
Figure 21B:
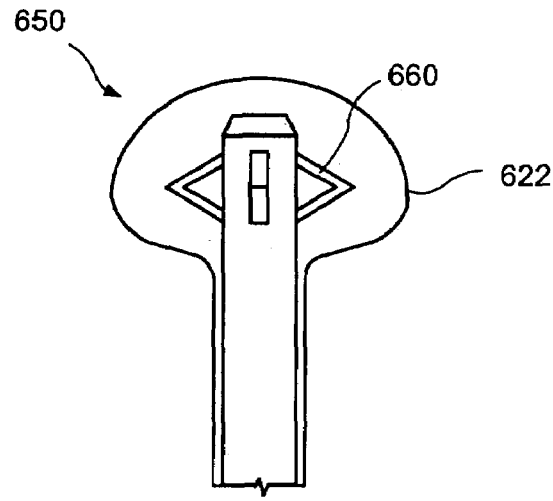
FIG. 21B shows the anastomotic connector delivery and deployment assembly of FIG. 21A in an expanded configuration.

In certain embodiments, one or more deployment members may be configured as an expandable member disposed within an inflatable member. FIGS. 21A and 21B show an exemplary embodiment of an anastomotic connector delivery and deployment assembly 650 having deployment member 610 that includes an expandable deployment member 660 disposed within an inflatable deployment member 622. FIG. 21A shows inflatable member 622 in a deflated state and expandable member 660 in an unexpanded state and FIG. 21B shows inflatable member 622 in an inflated state and expandable member 660 in an expanded state. In this particular embodiment, engagement member 600 has a single deployment member 610, however, it will be apparent that such a configuration may be employed with any embodiments described herein, e.g., a proximal and/or middle and/or distal deployment member may be configured as such, for example serially oriented or side-by-side relative to any other deployment member described herein.

Figure 22:
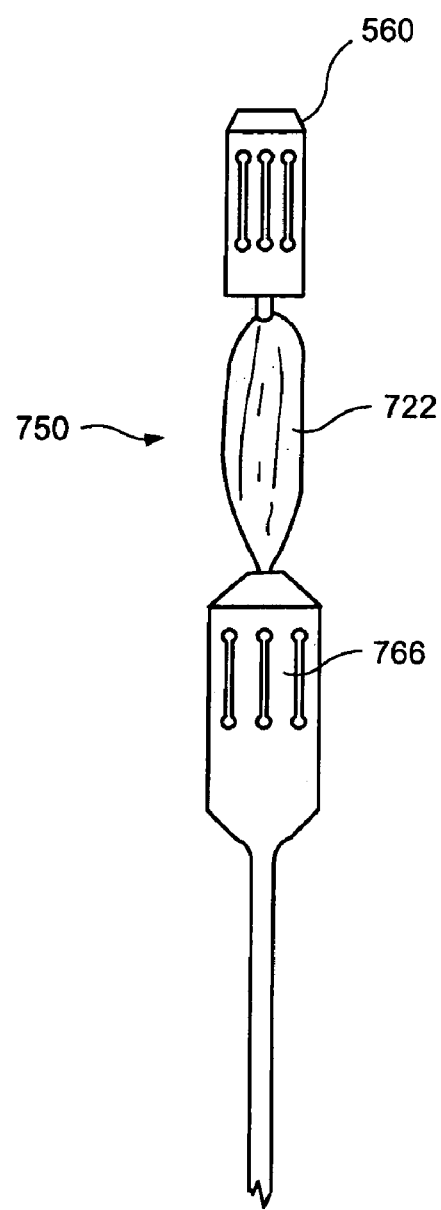
FIG. 22 shows an exemplary embodiment of a subject anastomotic connector delivery and deployment assembly having distal expandable deployment member, a middle inflatable deployment member and a proximal expandable deployment member.

As mentioned above, the subject invention may include more than one inflatable member and/or more than one expandable member. For example, three or more deployment members may be employed, for example serially arranged with respect to each other. FIG. 22 shows an exemplary embodiment of a subject anastomotic connector delivery and deployment member 750 having three deployment members arranged in a series. FIG. 22 shows assembly 750 having a first or distal expandable member 760, a second or middle inflatable member 722 and a third or proximal expandable member 766; however any of the deployment members may be of any suitable form, e.g., the distal and/or proximal member may be an inflatable member and/or the middle member may be an expandable member, or one or more of the deployment members may be an expandable member disposed within an inflatable member as described above, etc.

Kits

Also provided are kits that include at least one anastomosis system of the present invention, where in many embodiments the kits may include one or more systems having varying dimensions, e.g., varying inflatable or expandable member sizes and shapes, so as to provide the physician convenience and security of having a device with the correct size for a particular patient. The kits may further include other tools such as one or more proximators or sizing devices for determining the appropriate size of the components of the system to be used, and the like, which devices find use in performing an anastomosis. The kit may further include one or more anastomotic connectors to be implanted having the same or different sizes, shapes and configurations from each other. The subject kits may also include securing or reinforcement means, e.g., biocompatible glues/adhesives, hemostatic rings, clips, etc.

In addition, the subject kits typically include instructions for using the subject systems in methods according to the subject invention. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the Internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above description that the subject invention provides important new devices and procedures for delivering and implanting anastomotic connectors which overcome a number of disadvantages currently encountered in the field of anastomosis. The subject anastomosis systems are easy to use and can provide for vessel joinder with out the use of sutures, staples, glues, etc. Moreover, the subject systems are versatile and can be used in a variety of approaches and applications with a variety of differently configured connectors. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

What is claimed is:

1. A system for delivering an anastomotic connector to interconnect vessels, comprising:
    an elongated connector engagement member having a connector deployment mechanism at a distal end thereof, the connector deployment mechanism including an expandable member which, in a pre-deployment position is receivable within the anastomotic connector;
    a connector retaining member axially receiving said elongated connector engagement member therein and comprising a slit at a distal end thereof for holding at least a portion of the anastomotic connector therein;
    and a cuff engageable with the distal end of said retaining member and configured for receiving at least a portion of said anastomotic connector.

2. The system of claim 1, further comprising a sheath axially receiving said retaining member, wherein said sheath and said retaining member are axially translatable relative to each other to selectively maintain said anastomotic connector from an insertion configuration to a deployed configuration.

3. The system of claim 2, wherein said cuff is adapted for configuring the anastomotic connector into the insertion configuration and for loading the anastomotic connector into said sheath.

4. The system of claim 3, wherein said cuff comprises a split sleeve configuration.

5. The system of claim 3, wherein said cuff further comprises an opening for accommodating a portion of the anastomotic connector therein.

6. The system of claim 1, wherein said expandable member comprises at least one inflatable member.

7. The system of claim 6 wherein said at least one inflatable member is selectively inflatable and deflatable.

8. The system of claim 1, wherein said connector deployment mechanism comprises two expandable members.

9. A system for creating an anastomotic connection between a target vessel and a graft vessel, comprising:
    an anastomotic connector comprising at least one flexible member and a tubular flow channel, a flexibility of the flexible member being selected to enable the flexible member to conform to a shape of an inner surface of the target vessel and to be held, under normal physiological conditions, by an internal fluid pressure within the target vessel in sealing contact with an inner surface thereof; and
    a plurality of deployment members axially positioned within said tubular flow channel, wherein at least a portion of a first one of the deployment members is expandable to deploy the flexible member within a target vessel and a second one of the deployment members includes an expandable basket positioned within said tubular flow channel when said flexible member is deployed within said target vessel.

10. The system of claim 9, wherein the first deployment member includes an inflatable balloon.

11. A method of forming an anastomotic connection between two vessels, said method comprising:
    providing, in a deployed configuration, an anastomotic connector comprising a proximal flexible member, a distal flexible member and a tubular flow channel extending therebetween;
    inserting a first expandable member within the anastomotic connector;
    compressing the anastomotic connector to an insertion configuration;
    positioning the compressed anastomotic connector so that the distal flexible member is received within a first vessel;
    expanding the first expandable member to return the distal flexible member to the deployed configuration;
    collapsing the first expandable member;
    positioning the compressed anastomotic connector so that the proximal flexible member is received within a second vessel; and
    expanding the first expandable member within the second vessel to return the proximal flexible member to the deployed configuration.

12. The method of claim 11, wherein the first expandable member is a balloon which is expanded by providing an inflation fluid thereto.

13. The method of claim 11 further comprising expanding said tubular flow channel.

* * * * *